(12) United States Patent
Stoeckius

(10) Patent No.: US 11,702,698 B2
(45) Date of Patent: *Jul. 18, 2023

(54) ENHANCING SPECIFICITY OF ANALYTE BINDING

(71) Applicant: 10x Genomics, Inc., Pleasanton, CA (US)

(72) Inventor: Marlon Stoeckius, Pleasanton, CA (US)

(73) Assignee: 10x Genomics, Inc., Pleasanton, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/573,126

(22) Filed: Jan. 11, 2022

(65) Prior Publication Data

US 2022/0127672 A1    Apr. 28, 2022

Related U.S. Application Data

(63) Continuation of application No. PCT/US2020/059472, filed on Nov. 6, 2020.

(60) Provisional application No. 63/040,292, filed on Jun. 17, 2020, provisional application No. 62/933,299, filed on Nov. 8, 2019.

(51) Int. Cl.
*C12Q 1/6841* (2018.01)
*C12Q 1/6874* (2018.01)
*C12Q 1/6876* (2018.01)

(52) U.S. Cl.
CPC ......... *C12Q 1/6876* (2013.01); *C12Q 1/6841* (2013.01); *C12Q 1/6874* (2013.01); *C12Q 2521/327* (2013.01); *C12Q 2521/501* (2013.01); *C12Q 2523/109* (2013.01); *C12Q 2525/161* (2013.01); *C12Q 2537/163* (2013.01)

(58) Field of Classification Search
CPC ............ C12Q 1/6874; C12Q 2521/327; C12Q 2521/501; C12Q 2523/109; C12Q 2525/161; C12Q 2537/163
See application file for complete search history.

(56) References Cited

U.S. PATENT DOCUMENTS

| | | |
|---|---|---|
| 4,683,195 A | 7/1987 | Mullis |
| 4,683,202 A | 7/1987 | Mullis |
| 4,800,159 A | 1/1989 | Mullis |
| 4,883,867 A | 11/1989 | Lee |
| 4,965,188 A | 10/1990 | Mullis |
| 4,988,617 A | 1/1991 | Landegren et al. |
| 5,002,882 A | 3/1991 | Lunnen |
| 5,130,238 A | 7/1992 | Malek |
| 5,308,751 A | 5/1994 | Ohkawa |
| 5,321,130 A | 6/1994 | Yue |
| 5,410,030 A | 4/1995 | Yue |
| 5,436,134 A | 7/1995 | Haugland |
| 5,455,166 A | 10/1995 | Walker |
| 5,494,810 A | 2/1996 | Barany et al. |
| 5,503,980 A | 4/1996 | Cantor |
| 5,512,439 A | 4/1996 | Hornes |
| 5,512,462 A | 4/1996 | Cheng |
| 5,582,977 A | 12/1996 | Yue |
| 5,599,675 A | 2/1997 | Brenner |
| 5,641,658 A | 6/1997 | Adams |
| 5,648,245 A | 7/1997 | Fire et al. |
| 5,658,751 A | 8/1997 | Yue |
| 5,695,940 A | 12/1997 | Drmanac et al. |
| 5,750,341 A | 5/1998 | Macevicz |
| 5,763,175 A | 6/1998 | Brenner |
| 5,830,711 A | 11/1998 | Barany et al. |
| 5,837,832 A | 11/1998 | Chee et al. |
| 5,854,033 A | 12/1998 | Lizardi |
| 5,863,753 A | 1/1999 | Haugland |
| 5,871,921 A | 2/1999 | Landegren et al. |
| 5,912,148 A | 6/1999 | Eggerding |
| 5,925,545 A | 7/1999 | Reznikoff et al. |
| 5,958,775 A | 9/1999 | Wickstrrom |
| 5,965,443 A | 10/1999 | Reznikoff et al. |
| 6,013,440 A | 1/2000 | Lipshutz |
| 6,027,889 A | 2/2000 | Barany et al. |
| 6,054,274 A | 4/2000 | Sampson et al. |
| 6,060,240 A | 5/2000 | Kamb et al. |
| 6,130,073 A | 10/2000 | Eggerding |
| 6,143,496 A | 11/2000 | Brown |
| 6,153,389 A | 11/2000 | Haarer |
| 6,159,736 A | 12/2000 | Reznikoff et al. |
| 6,165,714 A | 12/2000 | Lane et al. |
| 6,210,891 B1 | 4/2001 | Nyren |

(Continued)

FOREIGN PATENT DOCUMENTS

| | | |
|---|---|---|
| AU | 2003200718 | 10/2006 |
| CN | 1273609 | 11/2000 |

(Continued)

OTHER PUBLICATIONS

U.S. Appl. No. 60/416,118, filed Oct. 3, 2002, Fan et al.

(Continued)

*Primary Examiner* — Angela M. Bertagna

(74) *Attorney, Agent, or Firm* — Fish & Richardson P.C.

(57) ABSTRACT

Methods for enhancing specificity of an analyte binding moiety or probe oligonucleotide to an analyte are provided herein. For example, methods provided herein include blocking a capture binding domain, thereby preventing hybridization to the capture domain of the capture probe affixed to a substrate. Further methods include releasing the block from the capture binding domain, thereby allowing the capture binding domain to specifically bind to the capture domain of the capture probe on the substrate.

25 Claims, 11 Drawing Sheets

Specification includes a Sequence Listing.

(56) References Cited

U.S. PATENT DOCUMENTS

| | | |
|---|---|---|
| 6,210,894 B1 | 4/2001 | Brennan |
| 6,214,587 B1 | 4/2001 | Dattagupta |
| 6,251,639 B1 | 6/2001 | Kurn |
| 6,258,568 B1 | 7/2001 | Nyren |
| 6,266,459 B1 | 7/2001 | Walt |
| 6,268,148 B1 | 7/2001 | Barany et al. |
| 6,274,320 B1 | 8/2001 | Rothberg |
| 6,291,180 B1 | 9/2001 | Chu |
| 6,291,187 B1 | 9/2001 | Kingsmore et al. |
| 6,300,063 B1 | 10/2001 | Lipshutz et al. |
| 6,309,824 B1 | 10/2001 | Drmanac |
| 6,323,009 B1 | 11/2001 | Lasken et al. |
| 6,344,316 B1 | 2/2002 | Lockhart |
| 6,344,329 B1 | 2/2002 | Lizardi et al. |
| 6,355,431 B1 | 3/2002 | Chee |
| 6,368,801 B1 | 4/2002 | Faruqi |
| 6,401,267 B1 | 6/2002 | Drmanac |
| 6,404,907 B1 | 6/2002 | Gilchrist |
| 6,432,360 B1 | 8/2002 | Church et al. |
| 6,503,713 B1 | 1/2003 | Rana |
| 6,506,561 B1 | 1/2003 | Cheval et al. |
| 6,534,266 B1 | 3/2003 | Singer |
| 6,544,732 B1 | 4/2003 | Chee |
| 6,573,043 B1 | 6/2003 | Cohen et al. |
| 6,579,695 B1 | 6/2003 | Lambalot |
| 6,620,584 B1 | 9/2003 | Chee |
| 6,632,641 B1 | 10/2003 | Brennan |
| 6,737,236 B1 | 5/2004 | Pieken et al. |
| 6,770,441 B2 | 8/2004 | Dickinson |
| 6,773,886 B2 | 8/2004 | Kaufman |
| 6,787,308 B2 | 9/2004 | Balasubramanian |
| 6,797,470 B2 | 9/2004 | Barany et al. |
| 6,800,453 B2 | 10/2004 | Labaer |
| 6,812,005 B2 | 11/2004 | Fan et al. |
| 6,828,100 B1 | 12/2004 | Ronaghi |
| 6,833,246 B2 | 12/2004 | Balasubramanian |
| 6,852,487 B1 | 2/2005 | Barany et al. |
| 6,859,570 B2 | 2/2005 | Walt |
| 6,864,052 B1 | 3/2005 | Drmanac |
| 6,867,028 B2 | 3/2005 | Janulaitis |
| 6,872,816 B1 | 3/2005 | Hall et al. |
| 6,875,572 B2 | 4/2005 | Prudent et al. |
| 6,890,741 B2 | 5/2005 | Fan et al. |
| 6,897,023 B2 | 5/2005 | Fu |
| 6,913,881 B1 | 7/2005 | Aizenstein et al. |
| 6,942,968 B1 | 9/2005 | Dickinson et al. |
| 7,011,944 B2 | 3/2006 | Prudent et al. |
| 7,057,026 B2 | 6/2006 | Barnes |
| 7,083,980 B2 | 8/2006 | Reznikoff et al. |
| 7,115,400 B1 | 10/2006 | Adessi |
| 7,118,883 B2 | 10/2006 | Inoue |
| 7,166,431 B2 | 1/2007 | Chee et al. |
| 7,192,735 B2 | 3/2007 | Lambalot |
| 7,211,414 B2 | 5/2007 | Hardin |
| 7,255,994 B2 | 8/2007 | Lao |
| 7,258,976 B2 | 8/2007 | Mitsuhashi |
| 7,282,328 B2 | 10/2007 | Kong et al. |
| 7,297,518 B2 | 11/2007 | Quake |
| 7,329,492 B2 | 2/2008 | Hardin |
| 7,358,047 B2 | 4/2008 | Hafner et al. |
| 7,361,488 B2 | 4/2008 | Fan et al. |
| 7,378,242 B2 | 5/2008 | Hurt |
| 7,393,665 B2 | 7/2008 | Brenner |
| 7,405,281 B2 | 7/2008 | Xu |
| 7,407,757 B2 | 8/2008 | Brenner |
| 7,473,767 B2 | 1/2009 | Dimitrov |
| 7,499,806 B2 | 3/2009 | Kermani et al. |
| 7,537,897 B2 | 5/2009 | Brenner |
| 7,563,576 B2 | 7/2009 | Chee |
| 7,579,153 B2 | 8/2009 | Brenner |
| 7,582,420 B2 | 9/2009 | Oliphant et al. |
| 7,601,498 B2 | 10/2009 | Mao |
| 7,608,434 B2 | 10/2009 | Reznikoff et al. |
| 7,611,869 B2 | 11/2009 | Fan |
| 7,635,566 B2 | 12/2009 | Brenner |
| 7,666,612 B2 | 2/2010 | Johnsson |
| 7,674,752 B2 | 3/2010 | He |
| 7,709,198 B2 | 5/2010 | Luo et al. |
| 7,776,547 B2 | 8/2010 | Roth |
| 7,776,567 B2 | 8/2010 | Mao |
| 7,803,943 B2 | 9/2010 | Mao |
| 7,888,009 B2 | 2/2011 | Barany et al. |
| 7,892,747 B2 | 2/2011 | Barany et al. |
| 7,910,304 B2 | 3/2011 | Drmanac |
| 7,914,981 B2 | 3/2011 | Barany et al. |
| 7,955,794 B2 | 6/2011 | Shen et al. |
| 7,960,119 B2 | 6/2011 | Chee |
| 7,985,565 B2 | 7/2011 | Mayer et al. |
| 8,003,354 B2 | 8/2011 | Shen et al. |
| 8,076,063 B2 | 12/2011 | Fan |
| 8,092,784 B2 | 1/2012 | Mao |
| 8,148,068 B2 | 4/2012 | Brenner |
| 8,206,917 B2 | 6/2012 | Chee |
| 8,268,554 B2 | 9/2012 | Schallmeiner |
| 8,288,103 B2 | 10/2012 | Oliphant |
| 8,288,122 B2 | 10/2012 | O'Leary et al. |
| 8,383,338 B2 | 2/2013 | Kitzman |
| 8,431,691 B2 | 4/2013 | McKernan et al. |
| 8,460,865 B2 | 6/2013 | Chee |
| 8,481,257 B2 | 7/2013 | Van Eijk |
| 8,481,258 B2 | 7/2013 | Church et al. |
| 8,481,292 B2 | 7/2013 | Casbon |
| 8,481,698 B2 | 7/2013 | Lieberman et al. |
| 8,507,204 B2 | 8/2013 | Pierce et al. |
| 8,519,115 B2 | 8/2013 | Webster et al. |
| 8,551,710 B2 | 10/2013 | Bernitz et al. |
| 8,568,979 B2 | 10/2013 | Stuelpnagel et al. |
| 8,586,310 B2 | 11/2013 | Mitra |
| 8,597,891 B2 | 12/2013 | Barany et al. |
| 8,603,743 B2 | 12/2013 | Liu et al. |
| 8,604,182 B2 | 12/2013 | Luo et al. |
| 8,614,073 B2 | 12/2013 | Van Eijk |
| 8,624,016 B2 | 1/2014 | Barany et al. |
| 8,685,889 B2 | 4/2014 | Van Eijk |
| 8,741,564 B2 | 6/2014 | Seligmann |
| 8,741,606 B2 | 6/2014 | Casbon |
| 8,771,950 B2 | 7/2014 | Church et al. |
| 8,785,353 B2 | 7/2014 | Van Eijk |
| 8,790,873 B2 | 7/2014 | Namsaraev et al. |
| 8,809,238 B2 | 8/2014 | Livak et al. |
| 8,815,512 B2 | 8/2014 | Van Eijk |
| 8,835,358 B2 | 9/2014 | Fodor |
| 8,865,410 B2 | 10/2014 | Shendure |
| 8,906,626 B2 | 12/2014 | Oliphant et al. |
| 8,911,945 B2 | 12/2014 | Van Eijk |
| 8,936,912 B2 | 1/2015 | Mitra |
| 8,951,726 B2 | 2/2015 | Luo et al. |
| 8,951,728 B2 | 2/2015 | Rasmussen |
| 8,986,926 B2 | 3/2015 | Ferree et al. |
| 9,005,891 B2 | 4/2015 | Sinicropi et al. |
| 9,005,935 B2 | 4/2015 | Belyaev |
| 9,023,768 B2 | 5/2015 | Van Eijk |
| 9,062,348 B1 | 6/2015 | Van Eijk |
| 9,080,210 B2 | 7/2015 | Van Eijk |
| 9,194,001 B2 | 11/2015 | Brenner |
| 9,201,063 B2 | 12/2015 | Sood et al. |
| 9,273,349 B2 | 3/2016 | Nguyen et al. |
| 9,290,808 B2 | 3/2016 | Fodor |
| 9,290,809 B2 | 3/2016 | Fodor |
| 9,328,383 B2 | 5/2016 | Van Eijk |
| 9,334,536 B2 | 5/2016 | Van Eijk |
| 9,371,563 B2 | 6/2016 | Geiss et al. |
| 9,371,598 B2 | 6/2016 | Chee |
| 9,376,716 B2 | 6/2016 | Van Eijk |
| 9,376,717 B2 | 6/2016 | Gao et al. |
| 9,376,719 B2 | 6/2016 | Eijk |
| 9,416,409 B2 | 8/2016 | Hayden |
| 9,447,459 B2 | 9/2016 | Van Eijk |
| 9,453,256 B2 | 9/2016 | Van Eijk |
| 9,493,820 B2 | 11/2016 | Van Eijk |
| 9,506,061 B2 | 11/2016 | Brown et al. |
| 9,512,422 B2 | 12/2016 | Barnard et al. |
| 9,574,230 B2 | 2/2017 | Van Eijk |
| 9,593,365 B2 | 3/2017 | Frisen et al. |

(56) References Cited

U.S. PATENT DOCUMENTS

| | | |
|---|---|---|
| 9,598,728 B2 | 3/2017 | Barany et al. |
| 9,624,538 B2 | 4/2017 | Church et al. |
| 9,644,204 B2 | 5/2017 | Hindson et al. |
| 9,657,335 B2 | 5/2017 | Van Eijk |
| 9,670,542 B2 | 6/2017 | Van Eijk |
| 9,694,361 B2 | 7/2017 | Bharadwaj |
| 9,702,004 B2 | 7/2017 | Van Eijk |
| 9,714,446 B2 | 7/2017 | Webster et al. |
| 9,714,937 B2 | 7/2017 | Dunaway |
| 9,727,810 B2 | 8/2017 | Fodor et al. |
| 9,745,627 B2 | 8/2017 | Van Eijk |
| 9,777,324 B2 | 10/2017 | Van Eijk |
| 9,783,841 B2 | 10/2017 | Nolan et al. |
| 9,790,476 B2 | 10/2017 | Gloeckner et al. |
| 9,816,134 B2 | 11/2017 | Namsaraev |
| 9,834,814 B2 | 12/2017 | Peter et al. |
| 9,850,536 B2 | 12/2017 | Oliphant et al. |
| 9,856,521 B2 | 1/2018 | Stevens et al. |
| 9,868,979 B2 | 1/2018 | Chee et al. |
| 9,879,313 B2 | 1/2018 | Chee et al. |
| 9,896,721 B2 | 2/2018 | Van Eijk |
| 9,898,576 B2 | 2/2018 | Van Eijk |
| 9,898,577 B2 | 2/2018 | Van Eijk |
| 9,902,991 B2 | 2/2018 | Sinicropi et al. |
| 9,909,167 B2 | 3/2018 | Samusik et al. |
| 9,938,566 B2 | 4/2018 | Shepard et al. |
| 9,957,550 B2 | 5/2018 | Yeakley et al. |
| 10,002,316 B2 | 6/2018 | Fodor et al. |
| 10,023,907 B2 | 7/2018 | Van Eijk |
| 10,030,261 B2 | 7/2018 | Frisen et al. |
| 10,035,992 B2 | 7/2018 | Gloeckner et al. |
| 10,041,949 B2 | 8/2018 | Bendall et al. |
| 10,059,989 B2 | 8/2018 | Giresi et al. |
| 10,059,990 B2 | 8/2018 | Boyden et al. |
| 10,095,832 B2 | 10/2018 | Van Eijk |
| 10,144,966 B2 | 12/2018 | Cantor |
| 10,208,982 B2 | 2/2019 | Bannish et al. |
| 10,227,639 B2 | 3/2019 | Levner et al. |
| 10,273,541 B2 | 4/2019 | Hindson et al. |
| 10,357,771 B2 | 7/2019 | Bharadwaj |
| 10,370,698 B2 | 8/2019 | Nolan et al. |
| 10,415,080 B2 | 9/2019 | Dunaway et al. |
| 10,465,235 B2 | 11/2019 | Gullberg et al. |
| 10,472,669 B2 | 11/2019 | Chee |
| 10,480,022 B2 | 11/2019 | Chee |
| 10,480,029 B2 | 11/2019 | Bent et al. |
| 10,494,667 B2 | 12/2019 | Chee |
| 10,495,554 B2 | 12/2019 | Deisseroth et al. |
| 10,501,777 B2 | 12/2019 | Beechem et al. |
| 10,501,791 B2 | 12/2019 | Church et al. |
| 10,510,435 B2 | 12/2019 | Cai et al. |
| 10,544,403 B2 | 1/2020 | Gloeckner et al. |
| 10,550,429 B2 | 2/2020 | Harada et al. |
| 10,590,244 B2 | 3/2020 | Delaney et al. |
| 10,633,648 B2 | 4/2020 | Seelig et al. |
| 10,640,816 B2 | 5/2020 | Beechem et al. |
| 10,640,826 B2 | 5/2020 | Church et al. |
| 10,669,569 B2 | 6/2020 | Gullberg et al. |
| 10,724,078 B2 | 7/2020 | Van Driel et al. |
| 10,725,027 B2 | 7/2020 | Bell |
| 10,774,372 B2 | 9/2020 | Chee et al. |
| 10,774,374 B2 | 9/2020 | Frisen et al. |
| 10,787,701 B2 | 9/2020 | Chee |
| 10,815,519 B2 | 10/2020 | Husain et al. |
| 10,829,803 B2 | 11/2020 | Terbrueggen et al. |
| 10,844,426 B2 | 11/2020 | Daugharthy et al. |
| 10,858,698 B2 | 12/2020 | Church et al. |
| 10,858,702 B2 | 12/2020 | Lucero et al. |
| 10,913,975 B2 | 2/2021 | So et al. |
| 10,914,730 B2 | 2/2021 | Chee et al. |
| 10,927,403 B2 | 2/2021 | Chee et al. |
| 10,961,566 B2 | 3/2021 | Chee |
| 11,008,607 B2 | 5/2021 | Chee |
| 11,046,996 B1 | 6/2021 | Chee et al. |
| 11,067,567 B2 | 7/2021 | Chee |
| 11,104,936 B2 | 8/2021 | Zhang et al. |
| 11,118,216 B2 | 9/2021 | Koshinsky et al. |
| 11,156,603 B2 | 10/2021 | Chee |
| 11,162,132 B2 | 11/2021 | Frisen et al. |
| 11,208,684 B2 | 12/2021 | Chee |
| 11,286,515 B2 | 3/2022 | Chee |
| 11,293,917 B2 | 4/2022 | Chee |
| 11,299,774 B2 | 4/2022 | Frisen et al. |
| 11,313,856 B2 | 4/2022 | Chee |
| 11,332,790 B2 | 5/2022 | Chell et al. |
| 11,352,659 B2 | 6/2022 | Frisen et al. |
| 11,352,667 B2 | 6/2022 | Hauling et al. |
| 11,359,228 B2 | 6/2022 | Chee et al. |
| 11,365,442 B2 | 6/2022 | Chee |
| 11,371,086 B2 | 6/2022 | Chee |
| 11,384,386 B2 | 7/2022 | Chee |
| 11,390,912 B2 | 7/2022 | Frisen et al. |
| 11,401,545 B2 | 8/2022 | Chee |
| 11,407,992 B2 | 8/2022 | Dadhwal |
| 11,408,029 B2 | 8/2022 | Katiraee et al. |
| 11,434,524 B2 | 9/2022 | Ramachandran Iyer et al. |
| 11,479,809 B2 | 10/2022 | Frisen et al. |
| 11,479,810 B1 | 10/2022 | Chee |
| 11,492,612 B1 | 11/2022 | Dadhwal |
| 11,505,828 B2 | 11/2022 | Chell et al. |
| 11,512,308 B2 | 11/2022 | Gallant et al. |
| 11,519,022 B2 | 12/2022 | Chee |
| 11,519,033 B2 | 12/2022 | Schnall-Levin et al. |
| 11,535,887 B2 | 12/2022 | Gallant et al. |
| 11,542,543 B2 | 1/2023 | Chee |
| 11,549,138 B2 | 1/2023 | Chee |
| 11,560,587 B2 | 1/2023 | Chee |
| 11,560,592 B2 | 1/2023 | Chew et al. |
| 11,560,593 B2 | 1/2023 | Chell et al. |
| 11,592,447 B2 | 2/2023 | Uytingco et al. |
| 11,608,498 B2 | 3/2023 | Gallant et al. |
| 11,608,520 B2 | 3/2023 | Galonska et al. |
| 11,613,773 B2 | 3/2023 | Frisen et al. |
| 11,618,897 B2 | 4/2023 | Kim et al. |
| 11,618,918 B2 | 4/2023 | Chee et al. |
| 11,624,063 B2 | 4/2023 | Dadhwal |
| 11,624,086 B2 | 4/2023 | Uytingco et al. |
| 11,634,756 B2 | 4/2023 | Chee |
| 2001/0055764 A1 | 12/2001 | Empendocles et al. |
| 2002/0040275 A1 | 4/2002 | Cravatt |
| 2002/0051986 A1 | 5/2002 | Baez et al. |
| 2002/0055100 A1 | 5/2002 | Kawashima |
| 2002/0058250 A1 | 5/2002 | Firth |
| 2002/0086441 A1 | 7/2002 | Baranov et al. |
| 2002/0164611 A1 | 11/2002 | Bamdad |
| 2003/0017451 A1 | 1/2003 | Wang et al. |
| 2003/0022207 A1 | 1/2003 | Balasubramanian |
| 2003/0064398 A1 | 4/2003 | Barnes |
| 2003/0138879 A1 | 7/2003 | Lambalot |
| 2003/0148335 A1 | 8/2003 | Shen et al. |
| 2003/0162216 A1 | 8/2003 | Gold |
| 2003/0165948 A1 | 9/2003 | Alsmadi et al. |
| 2003/0224419 A1 | 12/2003 | Corcoran |
| 2003/0232348 A1 | 12/2003 | Jones et al. |
| 2003/0232382 A1 | 12/2003 | Brennan |
| 2003/0235854 A1 | 12/2003 | Chan et al. |
| 2004/0033499 A1 | 2/2004 | Ilsley et al. |
| 2004/0067492 A1 | 4/2004 | Peng et al. |
| 2004/0082059 A1 | 4/2004 | Webb et al. |
| 2004/0096853 A1 | 5/2004 | Mayer |
| 2004/0106110 A1 | 6/2004 | Balasubramanian |
| 2004/0235103 A1 | 11/2004 | Reznikoff et al. |
| 2004/0248325 A1 | 12/2004 | Bukusoglu et al. |
| 2004/0259105 A1 | 12/2004 | Fan et al. |
| 2005/0003431 A1 | 1/2005 | Wucherpfennig |
| 2005/0014203 A1 | 1/2005 | Darfler et al. |
| 2005/0037393 A1 | 2/2005 | Gunderson et al. |
| 2005/0048580 A1 | 3/2005 | Labaer |
| 2005/0064460 A1 | 3/2005 | Holliger et al. |
| 2005/0095627 A1 | 5/2005 | Kolman et al. |
| 2005/0100900 A1 | 5/2005 | Kawashima et al. |
| 2005/0130173 A1 | 6/2005 | Leamon et al. |
| 2005/0136414 A1 | 6/2005 | Gunderson et al. |
| 2005/0164292 A1 | 7/2005 | Farooqui |

(56) References Cited

U.S. PATENT DOCUMENTS

| | | |
|---|---|---|
| 2005/0191656 A1 | 9/2005 | Drmanac et al. |
| 2005/0191698 A1 | 9/2005 | Chee et al. |
| 2005/0202433 A1 | 9/2005 | Van Beuningen |
| 2005/0227271 A1 | 10/2005 | Kwon |
| 2005/0260653 A1 | 11/2005 | LaBaer |
| 2005/0266417 A1 | 12/2005 | Barany et al. |
| 2006/0046313 A1 | 3/2006 | Roth |
| 2006/0084078 A1 | 4/2006 | Zhao |
| 2006/0105352 A1 | 5/2006 | Qiao et al. |
| 2006/0154286 A1 | 7/2006 | Kong et al. |
| 2006/0188901 A1 | 8/2006 | Barnes et al. |
| 2006/0199183 A1 | 9/2006 | Valat et al. |
| 2006/0211001 A1 | 9/2006 | Yu et al. |
| 2006/0216775 A1 | 9/2006 | Burkart et al. |
| 2006/0240439 A1 | 10/2006 | Smith et al. |
| 2006/0263789 A1 | 11/2006 | Kincaid |
| 2006/0275782 A1 | 12/2006 | Gunderson et al. |
| 2006/0281109 A1 | 12/2006 | Barr Ost et al. |
| 2007/0020640 A1 | 1/2007 | McCloskey et al. |
| 2007/0020669 A1 | 1/2007 | Ericsson |
| 2007/0026430 A1 | 2/2007 | Andersen et al. |
| 2007/0054288 A1 | 3/2007 | Su et al. |
| 2007/0087360 A1 | 4/2007 | Boyd |
| 2007/0099208 A1 | 5/2007 | Drmanac et al. |
| 2007/0128624 A1 | 6/2007 | Gormley et al. |
| 2007/0128656 A1 | 6/2007 | Agrawal |
| 2007/0134723 A1 | 6/2007 | Kozlov et al. |
| 2007/0161020 A1 | 7/2007 | Luo et al. |
| 2007/0161029 A1 | 7/2007 | Li et al. |
| 2007/0166705 A1 | 7/2007 | Milton et al. |
| 2007/0172873 A1 | 7/2007 | Brenner et al. |
| 2007/0207482 A1 | 9/2007 | Church et al. |
| 2007/0254305 A1 | 11/2007 | Paik et al. |
| 2007/0269805 A1 | 11/2007 | Hogers |
| 2008/0003586 A1 | 1/2008 | Hyde et al. |
| 2008/0009420 A1 | 1/2008 | Schroth et al. |
| 2008/0108082 A1 | 5/2008 | Rank et al. |
| 2008/0108804 A1 | 5/2008 | Hayashizaki et al. |
| 2008/0132429 A1 | 6/2008 | Perov et al. |
| 2008/0160580 A1 | 7/2008 | Adessi et al. |
| 2008/0220434 A1 | 9/2008 | Thomas |
| 2008/0261204 A1 | 10/2008 | Lexow |
| 2008/0286795 A1 | 11/2008 | Kawashima et al. |
| 2008/0293046 A1 | 11/2008 | Allawi et al. |
| 2009/0005252 A1 | 1/2009 | Drmanac et al. |
| 2009/0006002 A1 | 1/2009 | Honisch et al. |
| 2009/0018024 A1 | 1/2009 | Church et al. |
| 2009/0026082 A1 | 1/2009 | Rothberg et al. |
| 2009/0036323 A1 | 2/2009 | van Eijk et al. |
| 2009/0082212 A1 | 3/2009 | Williams |
| 2009/0099041 A1 | 4/2009 | Church et al. |
| 2009/0105959 A1 | 4/2009 | Braverman et al. |
| 2009/0117573 A1 | 5/2009 | Fu et al. |
| 2009/0127589 A1 | 5/2009 | Rothberg et al. |
| 2009/0155781 A1 | 6/2009 | Drmanac et al. |
| 2009/0170713 A1 | 7/2009 | van Eijk et al. |
| 2009/0202998 A1 | 8/2009 | Schlumpberger et al. |
| 2009/0233802 A1 | 9/2009 | Bignell et al. |
| 2009/0253581 A1 | 10/2009 | van Eijk et al. |
| 2009/0283407 A1 | 11/2009 | Van Eijk |
| 2009/0291854 A1 | 11/2009 | Weisinger-Mayr et al. |
| 2009/0312193 A1 | 12/2009 | Kim et al. |
| 2010/0035249 A1 | 2/2010 | Hayashizaki et al. |
| 2010/0069263 A1 | 3/2010 | Shendure et al. |
| 2010/0105052 A1 | 4/2010 | Drmanac et al. |
| 2010/0120097 A1 | 5/2010 | Matz et al. |
| 2010/0120098 A1 | 5/2010 | Grunenwald et al. |
| 2010/0129874 A1 | 5/2010 | Mitra et al. |
| 2010/0145037 A1 | 6/2010 | Brive et al. |
| 2010/0173384 A1 | 7/2010 | Johnsson et al. |
| 2010/0184618 A1 | 7/2010 | Namsaraev et al. |
| 2010/0210475 A1 | 8/2010 | Lee et al. |
| 2010/0227329 A1 | 9/2010 | Cuppens |
| 2010/0273219 A1 | 10/2010 | May et al. |
| 2011/0028685 A1 | 2/2011 | Purkayastha et al. |
| 2011/0033854 A1 | 2/2011 | Drmanac et al. |
| 2011/0045462 A1 | 2/2011 | Fu et al. |
| 2011/0059436 A1 | 3/2011 | Hardin et al. |
| 2011/0111409 A1 | 5/2011 | Sinicropi et al. |
| 2011/0152111 A1 | 6/2011 | Illumina |
| 2011/0245101 A1 | 10/2011 | Chee et al. |
| 2011/0245111 A1 | 10/2011 | Chee |
| 2011/0287435 A1 | 11/2011 | Grunenwald et al. |
| 2012/0021930 A1 | 1/2012 | Schoen et al. |
| 2012/0046175 A1 | 2/2012 | Rodesch et al. |
| 2012/0046178 A1 | 2/2012 | Van Den Boom et al. |
| 2012/0065081 A1 | 3/2012 | Chee |
| 2012/0135871 A1 | 5/2012 | van Eijk et al. |
| 2012/0202698 A1 | 8/2012 | van Eijk et al. |
| 2012/0202704 A1 | 8/2012 | Fan et al. |
| 2012/0220479 A1 | 8/2012 | Ericsson et al. |
| 2012/0245053 A1 | 9/2012 | Shirai et al. |
| 2012/0252702 A1 | 10/2012 | Muratani et al. |
| 2012/0258871 A1 | 10/2012 | Kozlov et al. |
| 2012/0289414 A1 | 11/2012 | Mitra et al. |
| 2012/0301925 A1 | 11/2012 | Belyaev |
| 2013/0005594 A1 | 1/2013 | Terbrueggen et al. |
| 2013/0005600 A1 | 1/2013 | Olek |
| 2013/0035239 A1 | 2/2013 | Kong et al. |
| 2013/0065768 A1 | 3/2013 | Zheng et al. |
| 2013/0079232 A1 | 3/2013 | Kain et al. |
| 2013/0244884 A1 | 9/2013 | Jacobson et al. |
| 2013/0261019 A1 | 10/2013 | Lin et al. |
| 2013/0302801 A1 | 11/2013 | Asbury et al. |
| 2013/0338042 A1 | 12/2013 | Shen et al. |
| 2014/0066318 A1 | 3/2014 | Frisen et al. |
| 2014/0121118 A1 | 5/2014 | Warner |
| 2014/0270435 A1 | 9/2014 | Dunn |
| 2014/0274731 A1 | 9/2014 | Raymond et al. |
| 2014/0323330 A1 | 10/2014 | Glezer et al. |
| 2014/0342921 A1 | 11/2014 | Weiner |
| 2015/0148239 A1 | 5/2015 | Jon |
| 2015/0292988 A1 | 10/2015 | Bharadwaj et al. |
| 2015/0344942 A1 | 12/2015 | Frisen et al. |
| 2016/0019337 A1 | 1/2016 | Roberts et al. |
| 2016/0024576 A1 | 1/2016 | Chee |
| 2016/0108458 A1 | 4/2016 | Frei et al. |
| 2016/0122817 A1 | 5/2016 | Jarosz et al. |
| 2016/0138091 A1 | 5/2016 | Chee et al. |
| 2016/0145677 A1 | 5/2016 | Chee et al. |
| 2016/0194692 A1 | 7/2016 | Gore et al. |
| 2016/0253584 A1 | 9/2016 | Fodor et al. |
| 2016/0289740 A1 | 10/2016 | Fu et al. |
| 2016/0298180 A1 | 10/2016 | Chee |
| 2016/0305856 A1 | 10/2016 | Boyden et al. |
| 2016/0333403 A1 | 11/2016 | Chee |
| 2016/0376642 A1 | 12/2016 | Landegren et al. |
| 2017/0009278 A1 | 1/2017 | Söderberg et al. |
| 2017/0016053 A1 | 1/2017 | Beechem et al. |
| 2017/0058339 A1 | 3/2017 | Chee |
| 2017/0058340 A1 | 3/2017 | Chee |
| 2017/0058345 A1 | 3/2017 | Chee |
| 2017/0088881 A1 | 3/2017 | Chee |
| 2017/0283860 A1 | 4/2017 | Kool et al. |
| 2017/0166962 A1 | 6/2017 | van Eijk et al. |
| 2017/0220733 A1 | 8/2017 | Zhuang et al. |
| 2017/0233722 A1 | 8/2017 | Seelig et al. |
| 2017/0335297 A1 | 11/2017 | Ha et al. |
| 2017/0335410 A1 | 11/2017 | Driscoll et al. |
| 2017/0349940 A1 | 12/2017 | Morin et al. |
| 2018/0057873 A1 | 3/2018 | Zhou et al. |
| 2018/0094316 A1 | 4/2018 | Oliphant et al. |
| 2018/0112261 A1 | 4/2018 | Van Driel et al. |
| 2018/0163265 A1 | 6/2018 | Zhang et al. |
| 2018/0179591 A1 | 6/2018 | van Eijk |
| 2018/0201925 A1 | 7/2018 | Steemers et al. |
| 2018/0201980 A1 | 7/2018 | Chee et al. |
| 2018/0208967 A1 | 7/2018 | Larman et al. |
| 2018/0216161 A1 | 8/2018 | Chen et al. |
| 2018/0216162 A1 | 8/2018 | Belhocine et al. |
| 2018/0237864 A1 | 8/2018 | Imler et al. |
| 2018/0245142 A1 | 8/2018 | So et al. |
| 2018/0247017 A1 | 8/2018 | van Eijk et al. |
| 2018/0291439 A1 | 10/2018 | van Eijk et al. |

(56) References Cited

U.S. PATENT DOCUMENTS

| | | |
|---|---|---|
| 2018/0305681 A1 | 10/2018 | Jovanovich et al. |
| 2018/0312822 A1 | 11/2018 | Lee et al. |
| 2018/0320226 A1 | 11/2018 | Church et al. |
| 2019/0055594 A1 | 2/2019 | Samusik et al. |
| 2019/0064173 A1 | 2/2019 | Bharadwaj et al. |
| 2019/0119735 A1 | 4/2019 | Deisseroth et al. |
| 2019/0135774 A1 | 5/2019 | Orbai |
| 2019/0145982 A1 | 5/2019 | Chee et al. |
| 2019/0161796 A1 | 5/2019 | Hauling et al. |
| 2019/0177777 A1 | 6/2019 | Chee |
| 2019/0177778 A1 | 6/2019 | Chee |
| 2019/0177789 A1 | 6/2019 | Hindson et al. |
| 2019/0177800 A1 | 6/2019 | Boutet et al. |
| 2019/0203275 A1 | 7/2019 | Frisen et al. |
| 2019/0218276 A1 | 7/2019 | Regev et al. |
| 2019/0218608 A1 | 7/2019 | Daugharthy et al. |
| 2019/0233878 A1 | 8/2019 | Delaney et al. |
| 2019/0233880 A1 | 8/2019 | Mir |
| 2019/0249226 A1 | 8/2019 | Bent et al. |
| 2019/0262831 A1 | 8/2019 | West et al. |
| 2019/0264268 A1 | 8/2019 | Frisen et al. |
| 2019/0271028 A1 | 9/2019 | Khafizov et al. |
| 2019/0271030 A1 | 9/2019 | Chee |
| 2019/0271031 A1 | 9/2019 | Chee |
| 2019/0300943 A1 | 10/2019 | Chee et al. |
| 2019/0300944 A1 | 10/2019 | Chee et al. |
| 2019/0300945 A1 | 10/2019 | Chee et al. |
| 2019/0309353 A1 | 10/2019 | Chee |
| 2019/0309354 A1 | 10/2019 | Chee |
| 2019/0309355 A1 | 10/2019 | Chee |
| 2019/0323071 A1 | 10/2019 | Chee |
| 2019/0323088 A1 | 10/2019 | Boutet et al. |
| 2019/0338353 A1 | 11/2019 | Belgrader et al. |
| 2019/0360043 A1 | 11/2019 | Pham et al. |
| 2019/0367969 A1 | 12/2019 | Belhocine et al. |
| 2019/0367982 A1 | 12/2019 | Belhocine et al. |
| 2019/0367997 A1 | 12/2019 | Bent et al. |
| 2020/0002763 A1 | 1/2020 | Belgrader et al. |
| 2020/0010891 A1 | 1/2020 | Beechem et al. |
| 2020/0024641 A1 | 1/2020 | Nolan et al. |
| 2020/0047010 A1 | 2/2020 | Lee et al. |
| 2020/0048690 A1 | 2/2020 | Chee |
| 2020/0063191 A1 | 2/2020 | Kennedy-Darling et al. |
| 2020/0063195 A1 | 2/2020 | Chee |
| 2020/0063196 A1 | 2/2020 | Chee |
| 2020/0071751 A1 | 3/2020 | Daugharthy et al. |
| 2020/0080136 A1 | 3/2020 | Zhang et al. |
| 2020/0109443 A1 | 4/2020 | Chee |
| 2020/0123597 A1 | 4/2020 | Daniel |
| 2020/0140920 A1 | 5/2020 | Pierce et al. |
| 2020/0199565 A1 | 6/2020 | Chen et al. |
| 2020/0199572 A1 | 6/2020 | Kuersten et al. |
| 2020/0224244 A1 | 7/2020 | Nilsson et al. |
| 2020/0239874 A1 | 7/2020 | Mikkelsen |
| 2020/0256867 A1 | 8/2020 | Hennek et al. |
| 2020/0277663 A1 | 9/2020 | Iyer |
| 2020/0277664 A1 | 9/2020 | Frenz |
| 2020/0283852 A1 | 9/2020 | Oliphant et al. |
| 2020/0299757 A1 | 9/2020 | Chee et al. |
| 2020/0325531 A1 | 10/2020 | Chee |
| 2020/0362398 A1 | 11/2020 | Kishi et al. |
| 2020/0370095 A1 | 11/2020 | Farmer et al. |
| 2020/0399687 A1 | 12/2020 | Frisen et al. |
| 2020/0407781 A1 | 12/2020 | Schnall-Levin |
| 2021/0010068 A1 | 1/2021 | Chee et al. |
| 2021/0010070 A1 | 1/2021 | Schnall-Levin et al. |
| 2021/0017587 A1 | 1/2021 | Cai et al. |
| 2021/0095331 A1 | 4/2021 | Fan et al. |
| 2021/0115504 A1 | 4/2021 | Cai et al. |
| 2021/0123040 A1 | 4/2021 | Macosko et al. |
| 2021/0140982 A1 | 5/2021 | Uytingco et al. |
| 2021/0150707 A1 | 5/2021 | Weisenfeld et al. |
| 2021/0155982 A1 | 5/2021 | Yin et al. |
| 2021/0158522 A1 | 5/2021 | Weisenfeld et al. |
| 2021/0172007 A1 | 6/2021 | Chee et al. |
| 2021/0189475 A1 | 6/2021 | Tentori et al. |
| 2021/0190770 A1 | 6/2021 | Delaney et al. |
| 2021/0198741 A1 | 7/2021 | Williams |
| 2021/0199660 A1 | 7/2021 | Williams et al. |
| 2021/0207202 A1 | 7/2021 | Chee |
| 2021/0214785 A1 | 7/2021 | Stoeckius |
| 2021/0222235 A1 | 7/2021 | Chee |
| 2021/0222241 A1 | 7/2021 | Bharadwaj |
| 2021/0222242 A1 | 7/2021 | Ramachandran Iyer |
| 2021/0222253 A1 | 7/2021 | Uytingco |
| 2021/0223227 A1 | 7/2021 | Stoeckius |
| 2021/0230584 A1 | 7/2021 | Mikkelsen et al. |
| 2021/0230681 A1 | 7/2021 | Patterson et al. |
| 2021/0230692 A1 | 7/2021 | Daugharthy et al. |
| 2021/0237022 A1 | 8/2021 | Bava |
| 2021/0238664 A1 | 8/2021 | Bava et al. |
| 2021/0238675 A1 | 8/2021 | Bava |
| 2021/0238680 A1 | 8/2021 | Bava |
| 2021/0247316 A1 | 8/2021 | Bava |
| 2021/0255175 A1 | 8/2021 | Chee et al. |
| 2021/0262018 A1 | 8/2021 | Bava et al. |
| 2021/0262019 A1 | 8/2021 | Alvarado Martinez et al. |
| 2021/0269864 A1 | 9/2021 | Chee |
| 2021/0270822 A1 | 9/2021 | Chee |
| 2021/0285036 A1 | 9/2021 | Yin et al. |
| 2021/0285046 A1 | 9/2021 | Chell et al. |
| 2021/0292748 A1 | 9/2021 | Frisen et al. |
| 2021/0292822 A1 | 9/2021 | Frisen et al. |
| 2021/0317510 A1 | 10/2021 | Chee et al. |
| 2021/0317524 A1 | 10/2021 | Lucero et al. |
| 2021/0324457 A1 | 10/2021 | Ramachandran Iyer et al. |
| 2021/0332424 A1 | 10/2021 | Schnall-Levin |
| 2021/0332425 A1 | 10/2021 | Pfeiffer et al. |
| 2021/0348221 A1 | 11/2021 | Chell et al. |
| 2022/0002791 A1 | 1/2022 | Frisen et al. |
| 2022/0003755 A1 | 1/2022 | Chee |
| 2022/0010367 A1 | 1/2022 | Ramachandran Iyer et al. |
| 2022/0017951 A1 | 1/2022 | Ramachandran Iyer et al. |
| 2022/0025446 A1 | 1/2022 | Shah |
| 2022/0025447 A1 | 1/2022 | Tentori et al. |
| 2022/0033888 A1 | 2/2022 | Schnall-Levin et al. |
| 2022/0049293 A1 | 2/2022 | Frenz et al. |
| 2022/0049294 A1 | 2/2022 | Uytingco et al. |
| 2022/0064630 A1 | 3/2022 | Bent et al. |
| 2022/0081728 A1 | 3/2022 | Williams |
| 2022/0090058 A1 | 3/2022 | Frisen et al. |
| 2022/0090175 A1 | 3/2022 | Uytingco et al. |
| 2022/0090181 A1 | 3/2022 | Gallant |
| 2022/0098576 A1 | 3/2022 | Dadhwal |
| 2022/0098661 A1 | 3/2022 | Chew et al. |
| 2022/0106632 A1 | 4/2022 | Galonska et al. |
| 2022/0106633 A1 | 4/2022 | Engblom et al. |
| 2022/0112486 A1 | 4/2022 | Ramachandran Iyer et al. |
| 2022/0112545 A1 | 4/2022 | Chee |
| 2022/0119869 A1 | 4/2022 | Ramachandran Iyer et al. |
| 2022/0127659 A1 | 4/2022 | Frisen et al. |
| 2022/0127666 A1 | 4/2022 | Katiraee et al. |
| 2022/0145361 A1 | 5/2022 | Frenz et al. |
| 2022/0154255 A1 | 5/2022 | Chee et al. |
| 2022/0170083 A1 | 6/2022 | Khaled et al. |
| 2022/0195422 A1 | 6/2022 | Gallant et al. |
| 2022/0195505 A1 | 6/2022 | Frisen et al. |
| 2022/0196644 A1 | 6/2022 | Chee |
| 2022/0213526 A1 | 7/2022 | Frisen et al. |
| 2022/0241780 A1 | 8/2022 | Tentori et al. |
| 2022/0267844 A1 | 8/2022 | Ramachandran Iyer et al. |
| 2022/0282329 A1 | 9/2022 | Chell et al. |
| 2022/0290217 A1 | 9/2022 | Frenz et al. |
| 2022/0290219 A1 | 9/2022 | Chee |
| 2022/0298560 A1 | 9/2022 | Frisen et al. |
| 2022/0325325 A1 | 10/2022 | Chee et al. |
| 2022/0326251 A1 | 10/2022 | Uytingco et al. |
| 2022/0333171 A1 | 10/2022 | Chee |
| 2022/0333192 A1 | 10/2022 | Uytingco |
| 2022/0333195 A1 | 10/2022 | Schnall-Levin et al. |
| 2022/0334031 A1 | 10/2022 | Delaney et al. |
| 2022/0348905 A1 | 11/2022 | Dadhwal |
| 2022/0348992 A1 | 11/2022 | Stoeckius et al. |
| 2022/0356464 A1 | 11/2022 | Kim et al. |

(56) References Cited

U.S. PATENT DOCUMENTS

| | | |
|---|---|---|
| 2022/0364163 A1 | 11/2022 | Stahl et al. |
| 2022/0389491 A1 | 12/2022 | Chee |
| 2022/0389504 A1 | 12/2022 | Chew et al. |
| 2022/0403455 A1 | 12/2022 | Ramachandran Iyer et al. |
| 2022/0404245 A1 | 12/2022 | Chell et al. |
| 2023/0002812 A1 | 1/2023 | Stoeckius et al. |
| 2023/0014008 A1 | 1/2023 | Shastry |
| 2023/0033960 A1 | 2/2023 | Gallant et al. |
| 2023/0034039 A1 | 2/2023 | Shahjamali |
| 2023/0034216 A1 | 2/2023 | Bava |
| 2023/0040363 A1 | 2/2023 | Chee |
| 2023/0042088 A1 | 2/2023 | Chee |
| 2023/0042817 A1 | 2/2023 | Mignardi |
| 2023/0047782 A1 | 2/2023 | Tentori et al. |
| 2023/0056549 A1 | 2/2023 | Dadhwal |
| 2023/0064372 A1 | 3/2023 | Chell et al. |
| 2023/0069046 A1 | 3/2023 | Chew et al. |
| 2023/0077364 A1 | 3/2023 | Patterson et al. |
| 2023/0080543 A1 | 3/2023 | Katiraee et al. |
| 2023/0081381 A1 | 3/2023 | Chew et al. |
| 2023/0100497 A1 | 3/2023 | Frisen et al. |
| 2023/0107023 A1 | 4/2023 | Chee |
| 2023/0111225 A1 | 4/2023 | Chew et al. |
| 2023/0113230 A1 | 4/2023 | Kim et al. |

FOREIGN PATENT DOCUMENTS

| | | |
|---|---|---|
| CN | 1537953 | 10/2004 |
| CN | 1680604 | 10/2005 |
| CN | 1749752 | 3/2006 |
| CN | 1898398 | 1/2007 |
| CN | 101142325 | 3/2008 |
| CN | 101221182 | 7/2008 |
| CN | 101522915 | 9/2009 |
| CN | 108949924 | 12/2018 |
| EP | 1782737 | 5/2007 |
| EP | 1910562 | 4/2008 |
| EP | 1923471 | 5/2008 |
| EP | 2002017 | 12/2008 |
| EP | 2292788 | 3/2011 |
| EP | 2302070 | 3/2011 |
| EP | 2881465 | 6/2015 |
| EP | 3013984 | 5/2016 |
| EP | 3511423 | 7/2019 |
| EP | 3541956 | 9/2019 |
| GB | 2520765 | 6/2015 |
| JP | 2007-014297 | 1/2007 |
| JP | 2007-074967 | 3/2007 |
| JP | 2009-036694 | 2/2009 |
| WO | WO 1989/010977 | 11/1989 |
| WO | WO 1991/006678 | 5/1991 |
| WO | WO 1993/004199 | 3/1993 |
| WO | WO 1995/023875 | 9/1995 |
| WO | WO 1995/025116 | 9/1995 |
| WO | WO 1995/035505 | 12/1995 |
| WO | WO 1997/031256 | 8/1997 |
| WO | WO 2000/17390 | 3/2000 |
| WO | WO 2001/06012 | 1/2001 |
| WO | WO 2001/009363 | 2/2001 |
| WO | WO 2001/012862 | 2/2001 |
| WO | WO 2001/042796 | 6/2001 |
| WO | WO 2001/046402 | 6/2001 |
| WO | WO 2001/059161 | 8/2001 |
| WO | WO 2001/090415 | 11/2001 |
| WO | WO 2001/096608 | 12/2001 |
| WO | WO 2002/040874 | 5/2002 |
| WO | WO 2002/059355 | 8/2002 |
| WO | WO 2002/059364 | 8/2002 |
| WO | WO 2002/077283 | 10/2002 |
| WO | WO 2003/002979 | 1/2003 |
| WO | WO 2003/008538 | 1/2003 |
| WO | WO 2003/010176 | 2/2003 |
| WO | WO 2003/102233 | 12/2003 |
| WO | WO 2004/015080 | 2/2004 |
| WO | WO 2004/067759 | 8/2004 |
| WO | WO 2004/081225 | 9/2004 |
| WO | WO 2005/007814 | 1/2005 |
| WO | WO 2005/010145 | 2/2005 |
| WO | WO 2005/026387 | 3/2005 |
| WO | WO 2005/042759 | 5/2005 |
| WO | WO 2005/113804 | 12/2005 |
| WO | WO 2006/020515 | 2/2006 |
| WO | WO 2006/124771 | 11/2006 |
| WO | WO 2007/041689 | 4/2007 |
| WO | WO 2007/060599 | 5/2007 |
| WO | WO 2007/073171 | 6/2007 |
| WO | WO 2007/076726 | 7/2007 |
| WO | WO 2007/139766 | 12/2007 |
| WO | WO 2007/145612 | 12/2007 |
| WO | WO 2008/069906 | 6/2008 |
| WO | WO 2009/032167 | 3/2009 |
| WO | WO 2009/152928 | 12/2009 |
| WO | WO 2010/019826 | 2/2010 |
| WO | WO 2010/027870 | 3/2010 |
| WO | WO 2010/126614 | 11/2010 |
| WO | WO 2011/008502 | 1/2011 |
| WO | WO 2011/062933 | 5/2011 |
| WO | WO 2011/068088 | 6/2011 |
| WO | WO 2011/094669 | 8/2011 |
| WO | WO 2011/127099 | 10/2011 |
| WO | WO 2012/049316 | 4/2012 |
| WO | WO 2012/071428 | 5/2012 |
| WO | WO 2012/129242 | 9/2012 |
| WO | WO 2012/140224 | 10/2012 |
| WO | WO 2012/159089 | 11/2012 |
| WO | WO 2013/131962 | 9/2013 |
| WO | WO 2013/150082 | 10/2013 |
| WO | WO 2014/130576 | 8/2014 |
| WO | WO 2014/152397 | 9/2014 |
| WO | WO 2015/031691 | 3/2015 |
| WO | WO 2015/069374 | 5/2015 |
| WO | WO 2016/077763 | 5/2016 |
| WO | WO 2017/143155 | 8/2017 |
| WO | WO 2017/184984 | 10/2017 |
| WO | WO 2017/192633 | 11/2017 |
| WO | WO 2017/222453 | 12/2017 |
| WO | WO 2018/022809 | 2/2018 |
| WO | WO 2018/023068 | 2/2018 |
| WO | WO 2018/026873 | 2/2018 |
| WO | WO 2018/045181 | 3/2018 |
| WO | WO 2018/045186 | 3/2018 |
| WO | WO 2018/057999 | 3/2018 |
| WO | WO 2018/064640 | 4/2018 |
| WO | WO 2018/075436 | 4/2018 |
| WO | WO 2018/085599 | 5/2018 |
| WO | WO 2018/091676 | 5/2018 |
| WO | WO 2018/107054 | 6/2018 |
| WO | WO 2018/136856 | 7/2018 |
| WO | WO 2018/144582 | 8/2018 |
| WO | WO 2018/209398 | 11/2018 |
| WO | WO 2019/023214 | 1/2019 |
| WO | WO 2019/032760 | 2/2019 |
| WO | WO 2019/068880 | 4/2019 |
| WO | WO 2019/075091 | 4/2019 |
| WO | WO 2019/113457 | 6/2019 |
| WO | WO 2019/126313 | 6/2019 |
| WO | WO 2019/140201 | 7/2019 |
| WO | WO 2019/165318 | 8/2019 |
| WO | WO 2019/213254 | 11/2019 |
| WO | WO 2019/213294 | 11/2019 |
| WO | WO 2019/241290 | 12/2019 |
| WO | WO 2020/028194 | 2/2020 |
| WO | WO 2020/047002 | 3/2020 |
| WO | WO 2020/047005 | 3/2020 |
| WO | WO 2020/047010 | 3/2020 |
| WO | WO 2020/056381 | 3/2020 |
| WO | WO 2020/076979 | 4/2020 |
| WO | WO 2020/099640 | 5/2020 |
| WO | WO 2020/112604 | 6/2020 |
| WO | WO 2020/117914 | 6/2020 |
| WO | WO 2020/123301 | 6/2020 |
| WO | WO 2020/123305 | 6/2020 |
| WO | WO 2020/123309 | 6/2020 |
| WO | WO 2020/123311 | 6/2020 |

(56) References Cited

FOREIGN PATENT DOCUMENTS

| | | |
|---|---|---|
| WO | WO 2020/123316 | 6/2020 |
| WO | WO 2020/123317 | 6/2020 |
| WO | WO 2020/123318 | 6/2020 |
| WO | WO 2020/123319 | 6/2020 |
| WO | WO 2020/123320 | 7/2020 |
| WO | WO 2020/160044 | 8/2020 |
| WO | WO 2020/167862 | 8/2020 |
| WO | WO 2020/176788 | 9/2020 |
| WO | WO 2020/176882 | 9/2020 |
| WO | WO 2020/190509 | 9/2020 |
| WO | WO 2020/198071 | 10/2020 |
| WO | WO 2020/206285 | 10/2020 |
| WO | WO 2020/219901 | 10/2020 |
| WO | WO 2020/240025 | 12/2020 |
| WO | WO 2020/243579 | 12/2020 |
| WO | WO 2020/254519 | 12/2020 |
| WO | WO 2021/041974 | 3/2021 |
| WO | WO 2021/067246 | 4/2021 |
| WO | WO 2021/067514 | 4/2021 |
| WO | WO 2021/091611 | 5/2021 |
| WO | WO 2021/097255 | 5/2021 |
| WO | WO 2021/102003 | 5/2021 |
| WO | WO 2021/102005 | 5/2021 |
| WO | WO 2021/102039 | 5/2021 |
| WO | WO 2021/119320 | 6/2021 |
| WO | WO 2021/133842 | 7/2021 |
| WO | WO 2021/133845 | 7/2021 |
| WO | WO 2021/133849 | 7/2021 |
| WO | WO 2021/142233 | 7/2021 |
| WO | WO 2021/168261 | 8/2021 |
| WO | WO 2021/168278 | 8/2021 |
| WO | WO 2021/216708 | 10/2021 |
| WO | WO 2021/225900 | 11/2021 |
| WO | WO 2021/236625 | 11/2021 |
| WO | WO 2021/236929 | 11/2021 |
| WO | WO 2021/237056 | 11/2021 |
| WO | WO 2021/237087 | 11/2021 |
| WO | WO 2021/242834 | 12/2021 |
| WO | WO 2021/247543 | 12/2021 |
| WO | WO 2021/247568 | 12/2021 |
| WO | WO 2021/252499 | 12/2021 |
| WO | WO 2021/252576 | 12/2021 |
| WO | WO 2021/252591 | 12/2021 |
| WO | WO 2021/252747 | 12/2021 |
| WO | WO 2021/263111 | 12/2021 |
| WO | WO 2022/025965 | 2/2022 |
| WO | WO 2022/060798 | 3/2022 |
| WO | WO 2022/060953 | 3/2022 |
| WO | WO 2022/061152 | 3/2022 |
| WO | WO 2022/087273 | 4/2022 |
| WO | WO 2022/099037 | 5/2022 |
| WO | WO 2022/109181 | 5/2022 |
| WO | WO 2022/140028 | 6/2022 |
| WO | WO 2022/147005 | 7/2022 |
| WO | WO 2022/147296 | 7/2022 |
| WO | WO 2022/164615 | 8/2022 |
| WO | WO 2022/178267 | 8/2022 |
| WO | WO 2022/198068 | 9/2022 |
| WO | WO 2022/221425 | 10/2022 |
| WO | WO 2022/226057 | 10/2022 |
| WO | WO 2022/236054 | 11/2022 |
| WO | WO 2022/256503 | 12/2022 |
| WO | WO 2022/271820 | 12/2022 |
| WO | WO 2023/287765 | 1/2023 |
| WO | WO 2023/018799 | 2/2023 |
| WO | WO 2023/034489 | 3/2023 |

OTHER PUBLICATIONS

U.S. Appl. No. 61/267,363, filed Dec. 7, 2009, Fan et al.
[No Author Listed], "Chromium Next GEM Single Cell 3' Reagent Kits v3.1—User Guide," 10x Genomics, Document No. CG000204, Nov. 2019, 58 pages.
[No Author Listed], "Chromium Next GEM Single Cell 3' Reagent Kits v3.1 (Dual Index)—User Guide," 10x Genomics, Mar. 2021, Document No. CG000315, 61 pages.
[No Author Listed], "HuSNP Mapping Assay User's Manual," Affymetrix Part No. 90094 (Affymetrix, Santa Clara, Calif.), GeneChip, 2000, 104 pages.
[No Author Listed], "Microarray technologies have excellent possibilities in genomics-related researches," Science Tools From Amersham Pharmacia Biotech, 1998, 3(4): 8 pages (with English Translation).
[No Author Listed], "Proseek® Multiplex 96×96 User Manual," Olink Proteomics, Olink Bioscience, Uppsala, Sweden, 2017, 20 pages.
10xGenomics.com, [online], "Visium Spatial Gene Expression Reagent Kits—Tissue Optimization," Oct. 2020, retrieved on Dec. 28, 2021, retrieved from URL<https://assets.ctfassets.net/an68im79xiti/5UJrN0cH17rEk0UXwdl9It/e54d99fb08a8fl500aba503005a04a56/CG000238_VisiumSpatialTissueOptimizationUserGuide_RevD.pdf>, 43 pages.
10xGenomics.com, [online], "Visium Spatial Gene Expression Reagent Kits—User Guide," Jun. 2020, retrieved on May 25, 2021, retrieved from URL<https://assets.ctfassets.net/an68im79xiti/3GGIfH3RWpdlbFVha1pexR/8baa08d9007157592b65b2cdc7130990/CG000239_VisiumSpatialGeneExpression_UserGuide_RevD.pdf>, 69 pages.
10xGenomics.com, [online], "Visium Spatial Gene Expression Reagent Kits—User Guide," Oct. 2020, retrieved on Dec. 28, 2021, retrieved from URL<https://assets.ctfassets.net/an68im79xiti/3GGIfH3RWpd1bFVha1pexR/8baa08d9007157592b65b2cdc7130990/CG000239_VisiumSpatialGeneExpression_UserGuide_RevD.pdf>, 70 pages.
10xGenomics.com, [online],"Visium Spatial Gene Expression Reagent Kits—Tissue Optimization—User Guide," Jul. 2020, retrieved on May 25, 2021, retrieved from URL<https://assets.ctfassets.net/an68im79xiti/5UJrN0cH17rEk0UXwd19It/e54d99fb08a8f1500aba503005a04a56/CG000238_VisiumSpatialTissueOptimizationUserGuide_RevD.pdf>, 42 pages.
Adessi et al., "Solid phase DNA amplification: characterisation of primer attachment and amplification mechanisms," Nucl. Acids Res., 2000, 28(20):E87, 8 pages.
Adiconis et al., "Comparative analysis of RNA sequencing methods for degraded or low-input samples," Nat Methods, Jul. 2013, 10(7):623-9.
Affymetrix, "GeneChip Human Genome U133 Set," retrieved from the Internet: on the World Wide Web at affymetrix.com/support/technical/datasheets/hgu133_datasheet.pdf, retrieved on Feb. 26, 2003, 2 pages.
Affymetrix, "Human Genome U95Av2," Internet Citation, retrieved from the internet: on the World Wide Web affymetrix.com, retrieved on Oct. 2, 2002, 1 page.
Alam, "Proximity Ligation Assay (PLA)," Curr Protoc Immunol., Nov. 2018, 123(1):e58, 8 pages.
Albretsen et al., "Applications of magnetic beads with covalently attached oligonucleotides in hybridization: Isolation and detection of specific measles virus mRNA from a crude cell lysate," Anal. Biochem., 1990, 189(1):40-50.
Allawi et al., "Thermodynamics and NMR of Internal G·T Mismatches in DNA," Biochemistry, 1996, 36(34):10581-10594.
Andresen et al., "Helicase-dependent amplification: use in OnChip amplification and potential for point-of-care diagnostics," Expert Rev Mol Diagn., Oct. 2009, 9(7):645-650.
Aran et al., "xCell: digitally portraying the tissue cellular heterogeneity landscape," Genome Biol., Nov. 2017, 18(1):220, 14 pages.
Archer et al., "Selective and flexible depletion of problematic sequences from RNA-seq libraries at the cDNA stage," BMC Genomics, May 2014, 15(1):401, 9 pages.
Armani et al., "2D-PCR: a method of mapping DNA in tissue sections," Lab Chip, 2009, 9(24):3526-34.
Atkinson et al., "An Updated Protocol for High Throughput Plant Tissue Sectioning," Front Plant Sci, 2017, 8:1721, 8 pages.
Atkinson, "Overview of Translation: Lecture Manuscript," U of Texas, 2000, DD, pp. 6.1-6.8.
Bains et al., "A novel method for nucleic acid sequence determination," Journal of Theoretical Biology, 1988, 135(3), 303-7.

(56) References Cited

OTHER PUBLICATIONS

Barnes, "PCR amplification of up to 35-kb DNA with high fidelity and high yield from lambda bacteriophage templates," Proc. Natl. Acad. Sci USA, 1994, 91(6):2216-2220.
Bartosovic et al., "Single-cell CUT&Tag profiles histone modifications and transcription factors in complex tissues," Nat Biotechnol., Jul. 2021, 39(7):825-835, Abstract.
Baugh et al., "Quantitative analysis of mRNA amplification by in vitro transcription," Nucleic Acids Res., 2001, 29(5):e29, 9 pages.
Beattie et al., "Advances in genosensor research," Clin Chem., May 1995, 41(5):700-6.
Beechem et al., "High-Plex Spatially Resolved RNA and Protein Detection Using Digital Spatial Profiling: A Technology Designed for Immuno-oncology Biomarker Discovery and Translational Research," Methods Mol Biol, 2020, Chapter 25, 2055:563-583.
Bell, "A simple way to treat PCR products prior to sequencing using ExoSAP-IT," Biotechniques, 2008, 44(6):834, 1 page.
Bentley et al., "Accurate whole human genome sequencing using reversible terminator chemistry," Nature, 2008, 456(7218):53-59.
Birney et al., "Identification and analysis of functional elements in 1% of the human genome by the ENCODE pilot project," Nature, 2007, 447(7146):799-816.
Blanchard et al., "High-density oligonucleotide arrays," Biosensors & Bioelectronics, 1996, 11(6-7):687-690.
Blanco et al., "A practical approach to FRET-based PNA fluorescence in situ hybridization," Methods, Dec. 2010, 52(4):343-51.
Blokzijl et al., "Profiling protein expression and interactions: proximity ligation as a tool for personalized medicine," J Intern. Med., 2010, 268(3):232-245.
Blow, "Tissue Issues," Nature, 2007, 448(7156):959-962.
Brandon et al., "Mitochondrial mutations in cancer," Oncogene, 2006, 25(34):4647-4662.
Brenner et al., "Gene expression analysis by massively parallel signature sequencing (MPSS) on microbead arrays," Nat. Biotech., 2000, 18(6):630-634.
Brenner et al., "In vitro cloning of complex mixtures of DNA on microbeads: physical separation of differentially expressed cDNAs," Proc. Natl. Acad. Sci. USA, 2000, 97(4):1665-1670.
Brow, "35—The Cleavase I enzyme for mutation and polymorphism scanning," PCR Applications Protocols for Functional Genomics, 1999, pp. 537-550.
Brown et al., "Retroviral integration: structure of the initial covalent product and its precursor, and a role for the viral IN protein," Proc Natl Acad Sci USA, Apr. 1989, 86(8):2525-9.
Buenrostro et al., "Transposition of native chromatin for multimodal regulatory analysis and personal epigenomics," Nat Methods, Dec. 2013, 10(12):1213-1218.
Bullard et al., "Direct comparison of nick-joining activity of the nucleic acid ligases from bacteriophage T4," Biochem. J. 2006, 398(1):435-144.
Burgess, "A space fortranscriptomics," Nature Reviews Genetics, 2016, 17(8):436-7.
Burgess, "Finding structure in gene expression," Nature Reviews Genetics, 2018, 19(5):249, 1 page.
Burton et al., "Coverslip Mounted-Immersion Cycled in Situ RT-PCR for the Localization of mRNA in Tissue Sections," Biotechniques, 1998, 24(1):92-100.
Cha et al., "Specificity, efficiency, and fidelity of PCR," Genome Res., 1993, 3(3):S18-29.
Chandra et al., "Cell-free synthesis-based protein microarrays and their applications," Proteomics, 2009, 5(6):717-30.
Chatteijee et al., "Mitochondrial DNA mutations in human cancer. Oncogene," 2006, 25(34):4663-4674.
Chen et al., "DNA hybridization detection in a microfluidic Channel using two fluorescently labelled nucleic acid probes," Biosensors and Bioelectronics, 2008, 23(12):1878-1882.
Chen et al., "Expansion microscopy," Science, 2015, 347(6221):543-548.
Chen et al., "Nanoscale imaging of RNA with expansion microscopy," Nat Methods, Aug. 2016, 13(8):679-84.
Chen et al., "RNA imaging. Spatially resolved, highly multiplexed RNA profiling in single cells," Science, Apr. 2015, 348(6233):aaa6090, 21 pages.
Chen et al., "Spatial Transcriptomics and In Situ Sequencing to Study Alzheimer's Disease," Cell, Aug. 2020, 182(4):976-991.
Chen et al., "Spatially resolved, highly multiplexed RNA profiling in single cells," Science, 2015, 348(6233):aaa6090, 21 pages.
Chen et al., "μCB-seq: microfluidic cell barcoding and sequencing for high-resolution imaging and sequencing of single cells," Lab Chip, Nov. 2020, 20(21):3899-3913.
Chrisey et al., "Covalent attachment of synthetic DNA to self-assembled monolayer films," Nucleic Acids Res., Aug. 1996, 24(15):3031-9.
Constantine et al., "Use of genechip high-density oligonucleotide arrays for gene expression monitoring," Life Sceience News, Amersham Life Science, 1998, pp. 11-14.
Corces et al., "An improved ATAC-seq protocol reduces background and enables interrogation of frozen tissues," Nat. Methods, 2017, 14(10):959-962.
Credle et al., "Multiplexed analysis of fixed tissue RNA using Ligation in situ Hybridization," Nucleic Acids Research, 2017, 45(14):e128, 9 pages.
Crosetto et al., "Spatially resolved transcriptomics and beyond," Nature Review Genetics, 2015, 16(1):57-66.
Cujec et al., "Selection of v-abl tyrosine kinase substrate sequences from randomized peptide and cellular proteomic libraries using mRNA display," Chemistry and Biology, 2002, 9(2):253-264.
Czarnik, "Encoding methods for combinatorial chemistry," Curr Opin Chem Biol., Jun. 1997, 1(1):60-6.
Dahl et al., "Circle-to-circle amplification for precise and sensitive DNA analysis," Proc. Natl. Acad. Sci., 2004, 101(13):4548-4553.
Darmanis et al., "ProteinSeq: High-Performance Proteomic Analyses by Proximity, Ligation and Next Generation Sequencing," PLos One, 2011, 6(9):e25583, 10 pages.
Daubendiek et al., "Rolling-Circle RNA Synthesis: Circular Oligonucleotides as Efficient Substrates for T7 RNA Polymerase," J. Am. Chem. Soc., 1995, 117(29):7818-7819.
Davies et al., "How best to identify chromosomal interactions: a comparison of approaches," Nat. Methods, 2017, 14(2):125-134.
Deamer et al., "Characterization of nucleic acids by nanopore analysis," Acc Chem Res., Oct. 2002, 35(10):817-25.
Dean et al., "Comprehensive human genome amplification using multiple displacement amplification," Proc Natl. Acad. Sci. USA, 2002, 99(8):5261-66.
Deng et al., "Spatial Epigenome Sequencing at Tissue Scale and Cellular Level," BioRxiv, Mar. 2021, 40 pages.
Dressman et al., "Transforming single DNA molecules into fluorescent magnetic particles for detection and enumeration of genetic variations," Proc. Natl. Acad. Sci. USA, 2003, 100(15):8817-8822.
Drmanac et al., "CoolMPS™: Advanced massively parallel sequencing using antibodies specific to each natural nucleobase," BioRxiv, 2020, 19 pages.
Druley et al., "Quantification of rare allelic variants from pooled genomic DNA," Nat. Methods, 2009, 6(4):263-65.
Duncan et al., "Affinity chromatography of a sequence-specific DNA binding protein using Teflon-linked oligonucleotides," Anal. Biochem., 1988, 169(1):104-108.
Eberwine, "Amplification of mRNA populations using aRNA generated from immobilized oligo(dT)-T7 primed cDNA," BioTechniques, 1996, 20(4):584-91.
Eguiluz et al., "Multitissue array review: a chronological description of tissue array techniques, applications and procedures," Pathology Research and Practice, 2006, 202(8):561-568.
Eldridge et al., "An in vitro selection strategy for conferring protease resistance to ligand binding peptides," Protein Eng Des Sel., 2009, 22(11):691-698.
Ellington et al., "Antibody-based protein multiplex platforms: technical and operational challenges," Clin Chem, 2010, 56(2):186-193.
Eng et al., "Profiling the transcriptome with RNA SPOTs," Nat Methods., 2017, 14(12):1153-1155.
Fire et al., "Rolling replication of short DNA circles," Proc. Natl. Acad. Sci., 1995, 92(10):4641-4645.

(56) References Cited

OTHER PUBLICATIONS

Flanigon et al., "Multiplex protein detection with DNA readout via mass spectrometry," N. Biotechnol., 2013, 30(2):153-158.
Fluidigm, "Equivalence of Imaging Mass Cytometry and Immunofluorescence on FFPE Tissue Sections," White Paper, 2017, 12 pages.
Fodor et al., "Light-directed, spatially addressable parallel chemical synthesis," Science, 1995, 251(4995):767-773.
Forster et al., "A human gut bacterial genome and culture collection for improved metagenomic analyses," Nature Biotechnology, 2019, 37(2):186-192.
Frese et al., "Formylglycine aldehyde Tag—protein engineering through a novel post-translational modification," ChemBioChem., 2009, 10(3):425-27.
Fu et al., "Counting individual DNA molecules by the stochastic attachment of diverse labels," PNAS, 2011, 108(22):9026-9031.
Fu et al., "Repeat subtraction-mediated sequence capture from a complex genome," Plant J., Jun. 2010, 62(5):898-909.
Fu et al., "Continuous Polony Gels for Tissue Mapping with High Resolution and RNA Capture Efficiency," bioRxiv, 2021, 20 pages.
Fullwood et al., "Next-generation DNA sequencing of paired-end tags (PET) for transcriptome and genome analyses," Genome Res., 2009, 19(4):521-532.
Ganguli et al., "Pixelated spatial gene expression analysis from tissue," Nat Commun., Jan. 2018, 9(1):202, 9 pages.
Gao et al., "Q&A: Expansion microscopy", BMC Biology, 15:50, 9 pages, 2017.
Gene@arrays[online], BeadArray Technology, available on or before Feb. 14, 2015, via Internet Archive: Wayback Machine URL <https://web.archive.org/web/20150214084616/http://genearrays.com/services/microarrays/illumina/beadarray-technology/>, [retrieved on Jan. 30, 2020], 3 pages.
Gill et al., "Nucleic acid isothermal amplification technologies: a review," Nucleosides Nucleotides Nucleic Acids, Mar. 2008, 27(3):224-43.
Glass et al., "SIMPLE: a sequential immunoperoxidase labeling and erasing method," J. Histochem. Cytochem., Oct. 2009, 57(10):899-905.
Gloor, "Gene targeting in *Drosophila*," Methods Mol Biol., 2004, 260:97-114.
Gnanapragasam, "Unlocking the molecular archive: the emerging use of formalin-fixed paraffin-embedded tissue for biomarker research in urological cancer," BJU International, 2009, 105(2):274-278.
Goldkorn et al., "A simple and efficient enzymatic method for covalent attachment of DNA to cellulose. Application for hybridization-restriction analysis and for in vitro synthesis of DNA probes," Nucleic Acids Res., 1986, 14(22):9171-9191.
Goryshin et al., "Tn5 in vitro transposition," J Biol Chem., Mar. 1998, 273(13):7367-74.
Govan et al., "Optochemical control of RNA interference in mammalian cells," Nucleic Acids Research, Dec. 2013, 41(22):10518-10528.
Gracia Villacampa et al., "Genome-wide Spatial Expression Profiling in FFPE Tissues," bioRxiv, 2020, p. 38 pages.
Grokhovsky, "Specificity of DNA cleavage by ultrasound," Molecular Biology, 2006, 40(2):276-283.
Gu et al., "Protein tag-mediated conjugation of oligonucleotides to recombinant affinity binders for proximity ligation," N Biotechnol., 2013, 30(2):144-152.
Gunderson et al., "Decoding randomly ordered DNA arrays," Genome Research, 2004, 14(5):870-877.
Guo et al., "Direct fluorescence analysis of genetic polymorphisms by hybridization with oligonucleotide arrays on glass supports," Nucleic Acids Res., Dec. 1994, 22(24):5456-65.
Gupta et al., "Single-cell isoform RNA sequencing characterizes isoforms in thousands of cerebellar cells," Nature Biotechnol., Oct. 2018, 36:1197-1202.
Habib et al., "Div-Seq: Single-nucleus RNA-Seq reveals dynamics of rare adult newborn neurons," Science, Aug. 2016, 353(6302):925-8.
Habib et al., "Massively parallel single-nucleus RNA-seq with DroNc-seq," Nat Methods, Oct. 2017, 14(10):955-958.
Hahnke et al., "Striptease on glass: validation of an improved stripping procedure for in situ microarrays," J Biotechnol., Jan. 2007, 128(1):1-13.
Hardenbol et al., "Highly multiplexed molecular inversion probe genotyping: over 10,000 targeted SNPs genotyped in a single tube assay," Genome Res., Feb. 2005, 15(2):269-75.
Hardenbol et al., "Multiplexed genotyping with sequence-tagged molecular inversion probes," Nature Biotechnol., Jun. 2003, 21(6):673-678.
Hayes et al., "Electrophoresis of proteins and nucleic acids: I-Theory," BMJ, Sep. 1989, 299(6703):843-6.
He et al., "In situ synthesis of protein arrays," Current Opinion in Biotechnology, 2008, 19(1):4-9.
He et al., "Printing protein arrays from DNA arrays," Nature Methods, 2008, 5(2):175-77.
He, "Cell-free protein synthesis: applications in proteomics and biotechnology," New Biotechnology, 2008, 25(2-3):126-132.
Healy, "Nanopore-based single-molecule DNA analysis," Nanomedicine (Lond), Aug. 2007, 2(4):459-81.
Hejatko et al., "In situ hybridization technique for mRNA detection in whole mount *Arabidopsis* samples," Nature Protocols, 2006, 1(4):1939-1946.
Hiatt et al., "Parallel, tag-directed assembly of locally derived short sequence reads," Nature Methods, 2010, 7(2):119-25.
Ho et al., "Bacteriophage T4 RNA ligase 2 (gp24.1) exemplifies a family of RNA ligases found in all phylogenetic domains," PNAS, Oct. 2002, 99(20):12709-14.
Hu et al., "Dissecting Cell-Type Composition and Activity-Dependent Transcriptional State in Mammalian Brains by Massively Parallel Single-Nucleus RNA-Seq," Mol Cell., Dec. 2017, 68(5):1006-1015.
Hu et al., "High reproducibility using sodium hydroxide-stripped long oligonucleotide DNA microarrays," Biotechniques, Jan. 2005, 38(1):121-4.
Hycultbiotech.com, [online], "Immunohistochemistry, Paraffin" Apr. 2010, retrieved on Apr. 16, 2020, retrieved from URL<https://www.hycultbiotech.com/media/wysiwyg/Protocol_Immunohistochemistry_Paraffin_2.pdf>, 3 pages.
Ichikawa et al., "In vitro transposition of transposon Tn3," J Biol. Chem., Nov. 1990, 265(31):18829-32, Abstract.
Jamur et al., "Permeabilization of cell membranes.," Method Mol. Biol., 2010, 588:63-66.
Jemt et al., "An automated approach to prepare tissue-derived spatially barcoded RNA-sequencing libraries," Scientific Reports, 2016, 6:37137, 10 pages.
Kap et al., "Histological assessment of PAXgene tissue fixation and stabilization reagents," PLoS One, 2011, 6:e27704, 10 pages.
Kapteyn et al., "Incorporation of non-natural nucleotides into template-switching oligonucleotides reduces background and improves cDNA synthesis from very small RNA samples," BMC Genomics, Jul. 2010, 11:413, 9 pages.
Karmakar et al., "Organocatalytic removal of formaldehyde adducts from RNA and DNA bases," Nature Chemistry, Aug. 3, 2015, 7(9):752-758.
Kaya-Okur et al., "CUT&Tag for efficient epigenomic profiling of small samples and single cells," Apr. 2019, 10(1):1930, 10 pages.
Kennedy-Darling et al., "Measuring the Formaldehyde Protein-DNA Cross-Link Reversal Rate," Analytical Chemistry, 2014, 86(12):5678-5681.
Kent et al., "Polymerase θ is a robust terminal transferase that oscillates between three different mechanisms during end-joining" Elife, Jun. 2016, 5:e13740, 25 pages.
Kirby et al., "Cryptic plasmids of *Mycobacterium avium*: Tn552 to the rescue," Mol Microbiol., Jan. 2002, 43(1):173-86.
Kleckner et al., "Tn10 and IS10 transposition and chromosome rearrangements: mechanism and regulation in vivo and in vitro," Curr Top Microbiol Immunol., 1996, 204:49-82.
Korbel et al., "Paired-end mapping reveals extensive structural variation in the human genome," Science, 2007, 318(5849):420-426.

(56) References Cited

OTHER PUBLICATIONS

Kozlov et al., "A highly scalable peptide-based assay system for proteomics," PLoS One, 2012, 7(6):e37441, 10 pages.
Kozlov et al., "A method for rapid protease substrate evaluation and optimization," Comb Chem High Throughput Screen, 2006, 9(6):481-87.
Kristensen et al., "High-Throughput Methods for Detection of Genetic Variation," BioTechniques, Feb. 2001, 30(2):318-332.
Kurz et al., "cDNA—protein fusions: covalent protein—gene conjugates for the in vitro selection of peptides and proteins," ChemBioChem., 2001, 2(9):666-72.
Kwok, "High-throughput genotyping assay approaches," Pharmocogenomics, Feb. 2000, 1(1):95-100.
Lacar et al., "Nuclear RNA-seq of single neurons reveals molecular signatures of activation," Nat Commun., Apr. 2016, 7:11022, 12 pages.
Lage et al., "Whole genome analysis of genetic alterations in small DNA samples using hyperbranched strand displacement amplification and array-CGH," Genome Research, 2003, 13(2):294-307.
Lake et al., "Neuronal subtypes and diversity revealed by single-nucleus RNA sequencing of the human brain," Science, Jun. 2016, 352(6293):1586-90.
Lampe et al., "A purified mariner transposase is sufficient to mediate transposition in vitro," EMBO J., Oct. 1996, 15(19):5470-9.
Landegren et al., "Reading bits of genetic information: methods for single-nucleotide polymorphism analysis," Genome Res., Aug. 1998, 8(8):769-76.
Langdale et al., "A rapid method of gene detection using DNA bound to Sephacryl," Gene, 1985, 36(3):201-210.
Larman et al., "Sensitive, multiplex and direct quantification of RNA sequences using a modified RASL assay," Nucleic Acids Research, 2014, 42(14):9146-9157.
Lee et al., "Fluorescent in situ sequencing (FISSEQ) of RNA for gene expression profiling in intact cells and tissues," Nature Protocols, 2015, 10(3):442-458.
Lee et al., "Highly multiplexed subcellular RNA sequencing in situ", Science, 343(6177):1360-1363, 2014.
Lee et al., "Improving the efficiency of genomic loci capture using oligonucleotide arrays for high throughput resequencing," BMC Genomics, Dec. 2009, 10:646, 12 pages.
Leriche et al., "Cleavable linkers in chemical biology," Bioorganic & Medicinal Chemistry, 2012, 20:571-582.
Li et al., "A photocleavable fluorescent nucleotide for DNA sequencing and analysis," Proc. Natl. Acad. Sci., 2003, 100(2):414-419.
Li et al., "An activity-dependent proximity ligation platform for spatially resolved quantification of active enzymes in single cells," Nat Commun, Nov. 2017, 8(1):1775, 12 pages.
Li et al., "RASL-seq for Massively Parallel and Quantitative Analysis of Gene Expression," Curr Protoc Mol Biol., Apr. 2012, 4(13):1-10.
Li et al., "Review: a comprehensive summary of a decade development of the recombinase polymerase amplification," Analyst, Dec. 2018, 144(1):31-67.
Lin et al., "Highly multiplexed imaging of single cells using a high-throughput cyclic immunofluorescence method," Nat Commun., Sep. 2015, 6:8390, 7 pages.
Linnarsson, "Recent advances in DNA sequencing methods—general principles of sample preparation," Experimental Cell Research, 2010, 316(8):1339-1343.
Liu et al., "High-Spatial-Resolution Multi-Omics Atlas Sequencing of Mouse Embryos via Deterministic Barcoding in Tissue," BioRxiv, 2019, 55 pages.
Liu et al., "Optochemical control of deoxyoligonucleotide function via a nucleobase-caging approach," Acc. Chem. Res., Jan. 2014, 47(1):45-55.
Lizardi et al., "Mutation detection and single-molecule counting using isothermal rolling-circle amplification," Nat. Genet., 1998, 19(3):225-232.

Lovatt et al., "Transcriptome in vivo analysis (TIVA) of spatially defined single cells in live tissue," Nature Methods, 2013, 11(2):190-196.
Lund et al., "Assessment of methods for covalent binding of nucleic acids to magnetic beads, Dynabeads, and the characteristics of the bound nucleic acids in hybridization reactions," Nucleic Acids Res., 1988, 16(22):10861-80.
Lundberg et al., "High-fidelity amplification using a thermostable DNA polymerase isolated from Pyrococcus furiosus," Gene, 1991, 108(1):1-6.
Lundberg et al., "Homogeneous antibody-based proximity extension assays provide sensitive and specific detection of low-abundant proteins in human blood," Nucleic Acids Res., 2011, 39(15):e102, 8 pages.
Lundberg et al., "Multiplexed homogeneous proximity ligation assays for high-throughput protein biomarker research in serological material," Mol Cell Proteomics, 2011, 10(4):M110.004978, 11 pages.
Lundin et al., "Increased throughput by parallelization of library preparation for massive sequencing," PLoS One, Apr. 2010, 5(4):e10029, 7 pages.
Lyck et al., "Immunohistochemical markers for quantitative studies of neurons and glia in human neocortex," J Histochem Cytochem, 2008, 56(3):201-21.
MacBeath et al., "Printing proteins as microarrays for high-throughput function determination," Science, Sep. 2000, 289(5485):1760-1763.
MacIntyre, "Unmasking antigens for immunohistochemistry.," Br J Biomed Sci., 2001, 58(3):190-6.
Marx, "Method of the Year: spatially resolved transcriptomics," Nature Methods, 2021, 18(1):9-14.
McCloskey et al., "Encoding PCR products with batch-stamps and barcodes," Biochem. Genet., 2007, 45(11-12):761-767.
Meers et al., "Improved CUT&RUN chromatin profiling tools," Elife, Jun. 2019, 8:e46314, 16 pages.
Merritt et al., "Multiplex digital spatial profiling of proteins and RNA in fixed tissue," Nat Biotechnol, May 2020, 38(5):586-599.
Metzker, "Sequencing technologies—the next generation," Nature Reviews Genetics, 2010, 11(1):31-46.
Miele et al., "Mapping cis- and trans-chromatin interaction networks using chromosome conformation capture (3C)," Methods Mol Biol., 2009, 464:105-21.
Miller et al., "Basic concepts of microarrays and potential applications in clinical microbiology," Clinical Microbiology Reviews, 2009, 22(4):611-633.
Mishra et al., "Three-dimensional genome architecture and emerging technologies: looping in disease," Genome Medicine, 2017, 9(1):87, 14 pages.
Mitra et al., "Digital genotyping and haplotyping with polymerase colonies," Proc. Natl. Acad. Sci. USA, May 2003, 100(10):5926-5931.
Mizusawa et al., "A bacteriophage lambda vector for cloning with BamHI and Sau3A," Gene, 1982, 20(3):317-322.
Morlan et al., "Selective depletion of rRNA enables whole transcriptome profiling of archival fixed tissue," PLoS One, Aug. 2012, 7(8):e42882, 8 pages.
Motea et al., "Terminal deoxynucleotidyl transferase: the story of a misguided DNA polymerase," Biochim Biophys Acta., May 2010, 1804(5):1151-66.
Nandakumar et al., "How an RNA Ligase Discriminates RNA versus DNA Damage," Molecular Cell, 2004, 16:211-221.
Ncbi.nlm.nih.gov, [online], "Molecular Inversion Probe Assay," available on or before Oct. 14, 2014, via Internet Archive: Wayback Machine URL<https://web.archive.org/web/20141014124037/https://www.ncbi.nlm.nih.gov/probe/docs/techmip/>, retrieved on Jun. 16, 2021, retrieved from URL<https://www.ncbi.nlm.nih.gov/probe/docs/techmip/>, 2 pages.
Ng et al., "Gene identification signature (GIS) analysis for transcriptome characterization and genome annotation," Nature Methods, 2005, 2(2):105-111.
Nichols et al., "RNA Ligases," Curr Protoc Mol Biol., Oct. 2008, 84(1):3.15.1-3.15.4.

(56) References Cited

OTHER PUBLICATIONS

Nikiforov et al., "The use of 96-well polystyrene plates for DNA hybridization-based assays: an evaluation of different approaches to oligonucleotide immobilization," Anal Biochem, May 1995, 227(1):201-9.
Niklas et al., "Selective permeabilization for the high-throughput measurement of compartmented enzyme activities in mammalian cells," Anal Biochem, Sep. 2011, 416(2):218-27.
Nowak et al., "Entering the Postgenome Era," Science, 1995, 270(5235):368-71.
Ohtsubo et al., "Bacterial insertion sequences," Curr Top Microbiol Immunol., 1996, 204:1-26.
Pandey et al., "Inhibition of terminal deoxynucleotidyl transferase by adenine dinucleotides. Unique inhibitory action of Ap5A," FEBS Lett., Mar. 1987, 213(1):204-8.
Park et al., "Single cell trapping in larger micro wells capable of supporting cell spreading and proliferation," Microfluid Nanofluid, 2010, 8:263-268.
PCT International Search Report and Written Opinion in International Appln. No. PCT/US2020/059472, dated May 17, 2021, 28 pages.
PCT Invitation to Pay Additional Fees in International Appln. No. PCT/US2020/059472, dated Feb. 15, 2021, 12 pages.
Pellestor et al., "The peptide nucleic acids (PNAs), powerful tools for molecular genetics and cytogenetics," Eur J Hum Genet, Sep. 2004, 12(9):694-700.
Pemov et al., "DNA analysis with multiplex microarray-enhanced PCR," Nucl. Acids Res., Jan. 2005, 33(2):e11, 9 pages.
Perler et al., "Intervening sequences in an Archaea DNA polymerase gen," Proc Natl Acad Sci USA, Jun. 1992, 89(12):5577-5581.
Petterson et al., "Generations of sequencing technologies," Genomics, 2009, 93(2):105-111.
Picelli et al., "Tn5 transposase and tagmentation procedures for massively scaled sequencing projects," Genome Res., Dec. 2014, 24(12):2033-40.
Pipenburg et al., "DNA detection using recombination proteins," PLoS Biol., Jul. 2006, 4(7):e204, 7 pages.
Plasterk, "The Tc1/mariner transposon family," Curr Top Microbiol Immunol., 1996, 204:125-43.
Plongthongkum et al., "Advances in the profiling of DNA modifications: cytosine methylation and beyond," Nature Reviews Genetics, Aug. 2014, 15(10):647-661.
Polsky-Cynkin et al., "Use of DNA immobilized on plastic and agarose supports to detect DNA by sandwich hybridization," Clin. Chem., 1985, 31(9):1438-1443.
U.S. Appl. No. 61/267,363, filed Dec. 7, 2009, 33 pages.
Raab et al., "Human tRNA genes function as chromatin insulators," EMBO J., Jan. 2012, 31(2):330-50.
Ranki et al., "Sandwich hybridization as a convenient method for the detection of nucleic acids in crude samples," Gene, 1983, 21(1-2):77-85.
Reinartz et al., "Massively parallel signature sequencing (MPSS) as a tool for in-depth quantitative gene expression profiling in all organisms," Brief Funct Genomic Proteomic, Feb. 2002, 1(1):95-104.
Reznikoff, "Tn5 as a model for understanding DNA transposition," Mol Microbiol., Mar. 2003, 47(5):1199-206.
Ristic et al., "Detection of Protein-Protein Interactions and Post-translational Modifications Using the Proximity Ligation Assay: Application to the Study of the SUMO Pathway," Methods Mol. Biol., 2016, 1449:279-90.
Rodriques et al., "Slide-seq: A scalable technology for measuring genome-wide expression at high spatial resolution," Science, 2019, 363(6434):1463-1467.
Ronaghi et al., "A sequencing method based on real-time pyrophosphate," Science, Jul. 1998, 281(5375):363-365.
Ronaghi et al., "Real-time DNA sequencing using detection of pyrophosphate release," Analytical Biochemistiy, Nov. 1996, 242(1):84-89.
Ronaghi, "Pyrosequencing sheds light on DNA sequencing," Genome Res, Jan. 2001, 11(1):3-11.
Roy et al., "Assessing long-distance RNA sequence connectivity via RNA-templated DNA-DNA ligation," eLife, 2015, 4:e03700, 21 pages.
Salmén et al., "Barcoded solid-phase RNA capture for Spatial Transcriptomics profiling in mammalian tissue sections," Nature Protocols, Oct. 2018, 13(11):2501-2534.
Saxonov et al.," 10x Genomics, Mastering Biology to Advance Human Health," PowerPoint, 10x, 2020, 41 pages.
Schena et al., "Quantitative monitoring of gene expression patterns with a complementary DNA microarray," Science, Oct. 1995, 270(5235):467-470.
Schweitzer et al., "Multiplexed protein profiling on microarrays by rolling-circle amplification," Nature Biotechnology, Apr. 2002, 20(4):359-365.
Shalon et al., "A DNA microarray system for analyzing complex DNA samples using two-color fluorescent probe hybridization," Genome Res., Jul. 1996, 6(7):639-45.
Shelbourne et al., "Fast copper-free click DNA ligation by the ring-strain promoted alkyne-azide cycloaddition reaction," Chem. Commun., 2011, 47(22):6257-6259.
Shendure et al., "Accurate multiplex polony sequencing of an evolved bacterial genome," Science, 2005, 309(5741):1728-1732.
Simonis et al., "Nuclear organization of active and inactive chromatin domains uncovered by chromosome conformation capture-on-chip (4C)," Nat Genet., Nov. 2006, 38(11):1348-54.
Skene et al., "An efficient targeted nuclease strategy for high-resolution mapping of DNA binding sites," Elife, Jan. 2017, 6:e21856, 35 pages.
Spitale et al., "Structural imprints in vivo decode RNA regulatory mechanisms," Nature, 2015, 519(7544):486-90.
Stahl et al., "Visualization and analysis of gene expression in tissue sections by spatial transcriptomics," Science, Jun. 2016, 353(6294):78-82.
Stahl et al., "Visualization and analysis of gene expression in tissue sections by spatial transcriptomics," Supplementary Materials, Science, Jul. 2016, 353(6294):78-82, 41 pages.
Stimpson et al., "Real-time detection of DNA hybridization and melting on oligonucleotide arrays by using optical wave guides," Proc Nad Acad Sci USA, Jul. 1995, 92(14):6379-83.
Stoddart et al., "Single-nucleotide discrimination in immobilized DNA oligonucleotides with a biological nanopore," PNAS USA., May 2009, 106(19):7702-7707.
Strell et al., "Placing RNA in context and space—methods for spatially resolved transcriptomics," The FEBS Journal, 2019, 286(8):1468-1481.
Stroh et al., "Quantum dots spectrally distinguish multiple species within the tumor milieu in vivo," Nat Med., Jun. 2005, 11(6):678-82.
Taylor et al., "Mitochondrial DNA mutations in human disease," Nature Reviews Genetics, May 2005, 6(5):389-402.
Tentori et al., "Detection of Isoforms Differing by a Single Charge Unit in Individual Cells," Chem. Int. Ed., 2016, 55(40):12431-5.
Tian et al., "Antigen peptide-based immunosensors for rapid detection of antibodies and antigens," Anal Chem, 2009, 81(13):5218-5225.
Tijssen et al., "Overview of principles of hybridization and the strategy of nucleic acid assays" in Techniques in Biochemistry and Molecular Biology—Hybridization with Nucleic Acid Probes, 1993, 24(Chapter 2), 65 pages.
Tolbert et al., "New methods for proteomic research: preparation of proteins with N-terminal cysteines for labeling and conjugation," Angewandte Chemie International Edition, Jun. 2002, 41(12):2171-4.
Trejo et al., "Extraction-free whole transcriptome gene expression analysis of FFPE sections and histology-directed subareas of tissue," PLoS One, Feb. 2019, 14(2):e0212031, 22 pages.
Twyman et al., "Techniques Patents for SNP Genotyping," Pharmacogenomics, Jan. 2003, 4(1):67-79.
U.S. Appl. No. 60/416,118 Fan et al., Multiplex Nucleic Acid Analysis Using Archived or Fixed Samples, filed Oct. 3, 2002, 22 pages.

(56) References Cited

OTHER PUBLICATIONS

Van Gelder et al., "Amplified RNA synthesized from limited quantities of heterogeneous cDNA," Proc. Natl. Acad. Sci. USA, 1990, 87(5):1663-1667.
Vandernoot et al., "cDNA normalization by hydroxyapatite chromatography to enrich transcriptome diversity in RNA-seq applications," Biotechniques, Dec. 2012, 53(6):373-80.
Vasiliskov et al., "Fabrication of microarray of gel-immobilized compounds on a chip by copolymerization," Biotechniques, Sep. 1999, 27(3):592-606.
Velculescu et al., "Serial analysis of gene expression," Science, Oct. 1995, 270(5235):484-7.
Vickovic et al., "High-definition spatial transcriptomics for in situ tissue profiling," Nat Methods, Oct. 2019, 16(10):987-990.
Vincent et al., "Helicase-dependent isothermal DNA amplification," EMBO Rep., Aug. 2004, 5(8):795-800.
Viollet et al., "T4 RNA ligase 2 truncated active site mutants: improved tools for RNA analysis," BMC Biotechnol., Jul. 2011, 11:72, 14 pages.
Vogelstein et al., "Digital PCR," Proceedings of the National Academy of Sciences, Aug. 1999, 96(16):9236-9241.
Waichman et al., "Functional immobilization and patterning of proteins by an enzymatic transfer reaction," Analytical chemistry, 2010, 82(4):1478-85.
Walker et al., "Strand displacement amplification—an isothermal, in vitro DNA amplification technique," Nucleic Acids Research, 1992, 20(7):1691-1696.
Wang et al., "Concentration gradient generation methods based on microfluidic systems," RSC Adv., 2017, 7:29966-29984.
Wang et al., "Imaging-based pooled CRISPR screening reveals regulators of lncRNA localization," Proc Natl Acad Sci USA, May 2019, 116(22):10842-10851.
Wang et al., "High-fidelity mRNA amplification for gene profiling," Nature Biotechnology, Apr. 2000, 18(4):457-459.
Wang, "RNA amplification for successful gene profiling analysis," J Transl Med., Jul. 2005, 3:28, 11 pages.
Weinreich et al., "Evidence that the cis Preference of the Tn5 Transposase is Caused by Nonproductive Multimerization," Genes and Development, Oct. 1994, 8(19):2363-2374.
Wiedmann et al., "Ligase chain reaction (LCR)—overview and applications," PCR Methods Appl., Feb. 1994, 3(4):S51-64.
Wilson et al., "New transposon delivery plasmids for insertional mutagenesis in Bacillus anthracis," J Microbiol Methods, Dec. 2007, 71(3):332-5.
Wolf et al., "Rapid hybridization kinetics of DNA attached to submicron latex particles," Nucleic Acids Res, 1987, 15(7):2911-2926.
Wong et al., "Direct Site-Selective Covalent Protein Immobilization Catalyzed by a Phosphopantetheinyl Transferase," J. Am. Chem Soc., 2008, 130(37):12456-64.
Worthington et al., "Cloning of random oligonucleotides to create single-insert plasmid libraries," Anal Biochem, 2001, 294(2):169-175.
Wu et al., "Detection DNA Point Mutation with Rolling-Circle Amplification Chip," IEEE, 2010 4th International Conference on Bioinformatics and Biomedical Engineering, Jun. 2010, 4 pages.
Yeakley et al., "Profiling alternative splicing on fiber-optic arrays," Nature biotechnology, 2002, 20:353-358.
Yeakley et al., "A trichostatin A expression signature identified by TempO-Seq targeted whole transcriptome profiling," PLoS One, May 2017, 12(5):e0178302, 22 pages.
Yershov et al., "DNA analysis and diagnostics on oligonucleotide microchips," Proc. Natl. Acad. Sci. USA, May 1996, 93(10):4913-4918.
Yin et al., "Genetically encoded short peptide tag for versatile protein labeling by Sfp phosphopantetheinyl transferase," PNAS, 2005, 102(44):15815-20.
Zhang et al., "Archaeal RNA ligase from thermoccocus kodakarensis for template dependent ligation," RNA Biol., Jan. 2017, 14(1):36-44.

Zhang et al., "Assembling DNA through Affinity Binding to Achieve Ultrasensitive Protein Detection," Angew Chem Int Ed Engl., 2013, 52(41):10698-705.
Zhang et al., "Binding-induced DNA assembly and its application to yoctomole detection of proteins," Anal Chem, 2012, 84(2):877-884.
Zhang et al., "Multiplex ligation-dependent probe amplification (MLPA) for ultrasensitive multiplexed microRNA detection using ribonucleotide-modified DNA probes†," Chem. Commun., 2013, 49:10013-10015.
Zheng et al., "Origins of human mitochondrial point mutations as DNA polymerase gamma-mediated errors," Mutat. Res., 2006, 599(1-2):11-20.
Zhou et al., "Genetically encoded short peptide tags for orthogonal protein labeling by Sfp and AcpS phosphopantetheinyl transferases," ACS Chemical Biol., 2007, 2(5):337-346.
Zhu et al., "Reverse transcriptase template switching: a SMART approach for full-length cDNA library construction," Biotechniques, Apr. 2001, 30(4):892-897.
10xGenomics.com, [online], "Visium Spatial Gene Expression Reagent Kits—Tissue Optimization," Nov. 2019, retrieved on Jan. 25, 2022, retrieved from URL<https://assets.ctfassets.net/an68im79xiti/4q03w6959AJFxffSw51ee9/6a2ac61cf6388a72564eeb96bc294967/CG000238_VisiumSpatialTissueOptimizationUserGuide_Rev_A.pdf> 46 pages.
Barnett et al., "ATAC-Me Captures Prolonged DNA Methylation of Dynamic Chromatin Accessibility Loci during Cell Fate Transitions," Mol Cell., Mar. 2020, 77(6):1350-1364.e6.
Cruz et al., "Methylation in cell-free DNA for early cancer detection," Ann Oncol., Jun. 2018, 29(6):1351-1353.
Hamaguchi et al., "Direct reverse transcription-PCR on oligo(dT)-immobilized polypropylene microplates after capturing total mRNA from crude cell lysates," Clin Chem., Nov. 1998, 44(11):2256-63.
Ke et al., "In situ sequencing for RNA analysis in preserved tissue and cells," Nat Methods., Sep. 2013, Supplementary Materials, 29 pages.
Miner et al., "Molecular barcodes detect redundancy and contamination in hairpin-bisulfite PCR," Nucleic Acids Res., Sep. 2004, 32(17):e135, 4 pages.
Wang et al., "Tagmentation-based whole-genome bisulfite sequencing," Nature Protocols, Oct. 2013, 8(10):2022-2032.
Illumina.com [online], "Ribo-Zero® rRNA Removal Kit Reference Guide," Aug. 2016, retrieved on Apr. 26, 2022, retrieved from URL <https://jp.support.illumina.com/content/dam/illumina-support/documents/documentation/chemistry_documentation/ribosomal-depletion/ribo-zero/ribo-zero-reference-guide-15066012-02.pdf>, 36 pages.
Niedringhaus et al., "Landscape of next-generation sequencing technologies," Anal Chem., Jun. 2011, 83(12):4327-41.
PCT International Preliminary' Report on Patentability in International Appln. No. PCT/US2020/059472, dated May 10, 2022, 17 pages.
Qiu et al., "Combination probes with intercalating anchors and proximal fluorophores for DNA and RNA detection," Nucleic Acids Research, Sep. 2016, 44(17):e138, 12 pages.
Schwers et al., "A high-sensitivity, medium-density, and target amplification-tree planar waveguide microarray system for gene expression analysis of formalin-fixed and paraffin-embedded tissue," Clin. Chem., Nov. 2009, 55(11):1995-2003.
Zhao et al., "Isothermal Amplification of Nucleic Acids," Chemical Review's, Nov. 2015, 115(22):12491-12545.
Asp et al., "Spatially Resolved Transcriptomes—Next Generation Tools for Tissue Exploration," Bioessays, Oct. 2020, 42(10):e1900221, 16 pages.
Balakrishnan et al., "Flap endonuclease 1," Annu Rev Biochem., Jun. 2013, 82:119-138.
Bergenstråhle et al., "Seamless integration of image and molecular analysis for spatial transcriptomics workflows," BMC Genomics, Jul. 2020, 21(1):482, 7 pages.
Berger et al., "Universal bases for hybridization, replication and chain termination," Nucleic Acid Res., Aug. 2000, 28(15):2911-2914.
Blair et al., "Microarray temperature optimization using hybridization kinetics." Methods Mol Biol., 2009, 529:171-96.

(56) References Cited

OTHER PUBLICATIONS

Bolotin et al., "MiXCR: software for comprehensive adaptive immunity profiling," Nat Methods., May 2015, 12(5):380-1.
Chen et al., "Parallel single nucleotide polymorphism genotyping by surface invasive cleavage with universal detection," Anal Chem., Apr. 2005, 77(8):2400-5.
Chester et al., "Dimethyl sulfoxide-mediated primer Tm reduction: a method for analyzing the role of renaturation temperature in the polymerase drain reaction," Anal Biochem, Mar. 1993, 209(2):284-90.
Ciaccio et al., "Systems analysis of EGF receptor signaling dynamics with microwestern arrays," Nat Methods, Feb. 2010, 7(2):148-55.
Gerard et al., "Excess dNTPs minimize RNA hydrolysis during reverse transcription," Biotechniques, Nov. 2002, 33(5):984, 986, 988, 990.
Hessner et al., "Genotyping of factor V G1691A (Leiden) without the use of PCR by invasive cleavage of oligonucleotide probes," Clin Chem., Aug. 2000. 46(8 Pt 1):1051-6.
Hoffman et al., "Formaldehyde crosslinking: a tool for the study of chromatin complexes," J Biol Chem., Oct. 2015, 290(44):26404-11.
Hughes et al., "Microfluidic Western blotting," PNAS, Dec. 2012, 109(52):21450-21455.
Jucá et al., "Effect of dimethyl sulfoxide on reverse transcriptase activity," Braz. J. Med. Biol. Res., Mar. 1995, 28(3):285-90.
Kalantari et al., "Deparaffinization of formalin-fixed paraffin-embedded tissue blocks using hot water instead of xylene," Anal Biochem., Aug. 2016, 507:71-3.
Krzywkowski et al., "Chimeric padlock and iLock probes for increased efficiency of targeted RNA detection," RNA, Jan. 2019, 25(1):82-89.
Krzywkowski et al., "Fidelity of RNA templated end-joining by chlorella virus DNA ligase and a novel iLock assay with improved direct RNA detection accuracy," Nucleic Acids Research, Oct. 2017, 45(18):e161, 9 pages.
Lyamichev et al., "Invader assay for SNP genotyping," Methods Mol Biol., 2003, 212:229-40.
Lyamichev et al., "Polymorphism identification and quantitative detection of genomic DNA by invasive cleavage of oligonucleotide probes," Nat Biotechnol., Mar. 1999, 17(3):292-6.
Nilsson et al., "RNA-templated DNA ligation for transcript analysis," Nucleic Acids Res., Jan. 2001, 29(2):578-81.
Olivier, "The Invader assay for SNP genotyping," Mutat. Res., Jun. 2005, 573(1-2):103-110.
Penno et al., "Stimulation of reverse transcriptase generated cDNAs with specific indels by template RNA structure: retrotransposon, dNTP balance, RT-reagent usage," Nucleic Acids Res., Sep. 2017, 45(17):10143-10155.
Perocchi et al., "Antisense artifacts in transcriptome microarray experiments are resolved by actinomycin D," Nucleic Acids Res., 2007, 35(19):e128, 7 pages.
Picelli et al., "Full-length RNA-seq from single cells using Smart-seq2," Nat Protoc., Jan. 2014, 9(1):171-81.
Schouten et al., "Relative quantification of 40 nucleic acid sequences by multiplex ligation-dependent probe amplification," Nucleic Acids Res., Jun. 2002, 30(12):e57, 13 pages.
Singh et al., "High-throughput targeted long-read single cell sequencing reveals the clonal and transcriptional landscape of lymphocytes," Nat Commun., Jul. 2019, 10(1):3120, 13 pages.
Sountoulidis et al., "SCRINSHOT, a spatial method for single-cell resolution mapping of cell states in tissue sections," PLoS Biol., Nov. 2020, 18(11):e3000675, 32 pages.
Spiess et al., "A highly efficient method for long-chain cDNA synthesis using trehalose and betaine," Anal. Biochem., Feb. 2002, 301(2):168-74.
Sutherland et al., "Utility of formaldehyde cross-linking and mass spectrometry in the study of protein-protein interactions," J. Mass Spectrom., Jun. 2008, 43(6):699-715.
Toubanaki et al., "Dry-reagent disposable biosensor for visual genotyping of single nucleotide polymorphisms by oligonucleotide ligation reaction: application to pharmacogenetic analysis," Hum Mutat., Aug. 2008, 29(8):1071-8.
Tu et al., "TCR sequencing paired with massively parallel 3' RNA-seq reveals clonotypic T cell signatures," Nature Immunology, Dec. 2019, 20(12):1692-1699.
Vázquez Bernat et al., "High-Quality Library Preparation for NGS-Based Immunoglobulin Germline Gene Inference and Repertoire Expression Analysis," Front Immunol., Apr. 2019, 10:660, 12 pages.
Wu et al., "RollFISH achieves robust quantification of single-molecule RNA biomarkers in paraffin-embedded tumor tissue samples," Commun Biol., Nov. 2018, 1:209, 8 pages.
Yasukawa et al., "Effects of organic solvents on the reverse transcription reaction catalyzed by reverse transcriptases from avian myeloblastosis virus and Moloney murine leukemia virus," Biosci Biotechnol Biochem., 2010, 74(9):1925-30.
U.S. Appl. No. 17/707,189, filed Mar. 29, 2022, Chell et al.
Amidzadeh et al., "Assessment of different permeabilization methods of minimizing damage to the adherent cells for detection of intracellular RNA by flow cytometry," Avicenna J Med Biotechnol., Jan. 2014, 6(1):38-46.
Boulé et al., "Terminal deoxynucleotidyl transferase indiscriminately incorporates ribonucleotides and deoxyribonucleotides," J Biol Chem., Aug. 2001, 276(33):31388-93.
Burgess, "Spatial transcriptomics coming of age," Nat Rev Genet., Jun. 2019, 20(6):317, 1 page.
Caliari et al., "A practical guide to hydrogels for cell culture," Nat Methods., Apr. 2016, 13(5):405-14.
Dalma-Weiszhausz et al., "The affymetrix GeneChip platform: an overview," Methods Enzymol., 2006, 410:3-28.
Evers et al., "The effect of formaldehyde fixation on RNA: optimization of formaldehyde adduct removal," J Mol Diagn,, May 2011, 13(3):282-8.
Gansauge et al., "Single-stranded DNA library preparation from highly degraded DNA using T4 DNA ligase," Nucleic Acids Res., Jun. 2017, 45(10):e79, 10 pages.
Hafner et al., "Identification of microRNAs and other small regulatory RNAs using cDNA library sequencing," Methods, Jan. 2008, 44(1):3-12.
Hanauer et al., "Separation of nanoparticles by gel electrophoresis according to size and shape," Nano Lett, Sep. 2007, 7(9):2881-5.
Ho et al., "Characterization of an ATP-Dependent DNA Ligase Encoded by Chlorella Virus PBCV-1," Journal of Virology, Mar. 1997, 71(3):1931-1937.
Hsuih et al., "Novel, Ligation-Dependent PCR Assay for Detection of Hepatitis C Virus in Serum," Journal of Clinical Microbiology, Mar. 1996, 34(3):501-507.
Jensen et al., "Zinc fixation preserves flow cytometry scatter and fluorescence parameters and allows simultaneous analysis of DNA content and synthesis, and intracellular and surface epitopes," Cytometry A., Aug. 2010, 77(8):798-804.
Kumar et al., "Template-directed oligonucleotide strand ligation, covalent intramolecular DNA circularization and catenation using click chemistiy," J Am Chem Soc., May 2007, 129(21):6859-64.
Lahiani et al., "Enabling Histopathological Annotations on Immunofluorescent Images through Virtualization of Hematoxylin and Eosin," J Pathol Inform., Feb. 2018, 9:1, 8 pages.
Lou et al., "A review of room temperature storage of biospecimen tissue and nucleic acids for anatomic pathology laboratories and biorepositories," Clin Biochem., Mar. 2014, 47(4-5):267-73.
Lykidis et al., "Novel zinc-based fixative for high quality DNA, RNA and protein analysis," Nucleic Acids Res., Jun. 2007, 35(12):e85, 10 pages.
Miller et al., "Chapter 11—Solid and Suspension Microarrays for Microbial Diagnostics," Methods in Microbiology, 2015, 42:395-431.
Miura et al., "Highly efficient single-stranded DNA ligation technique improves low-input wholegenome bisulfite sequencing by post-bisulfite adaptor tagging," Nucleic Acids Res., Sep. 2019, 47(15):e85, 10 pages.
Mulder et al., "CapTCR-seq: hybrid capture for T-cell receptor repertoire profiling," Blood Advances, Dec. 2018, 2(23):3506-3514.

(56) References Cited

OTHER PUBLICATIONS

Nadji et al., "Immunohistochemistry of tissue prepared by a molecular-friendly fixation and processing system," Appl Immunohistochem Mol Morphol., Sep. 2005, 13(3):277-82.
Nandakumar et al., "RNA Substrate Specificity and Structure-guided Mutational Analysis of Bacteriophage T4 RNA Ligase 2," Journal of Biological Chemistry, Jul. 2004, 279(30):31337-31347.
Ozsolak et al., "Digital transcriptome profiling from attomole-level RNA samples," Genome Res., Apr. 2010, 20(4):519-25.
Passow et al., "RNAlater and flash freezing storage methods nonrandomly influence observed gene expression in RNAseq experiments," bioRxiv, Jul. 2018, 28 pages.
Porreca et al., "Polony DNA sequencing," Curr Protoc Mol Biol., Nov. 2006, Chapter 7, Unit 7.8, pp. 7.8.1-7.8.22.
Slomovic et al., "Addition of poly (A) and poly(A)-rich tails during RNA degradation in the cytoplasm of human cells," Proc Natl Acad Sci USA, Apr. 2010, 107(16):7407-12.
Ulery et al., "Biomedical Applications of Biodegradable Polymers," J Polym Sci B Polym Phys., Jun. 2011, 49(12):832-864.
Vandenbroucke et al., "Quantification of splice variants using real-time PCR," Nucleic Acids Research, 2001, 29(13):e68, 7 pages.
Wang et al., "Optimization of Process Conditions for Infected Animal Tissues by Alkaline Hydrolysis Technology," Procedia Environmental Sciences, 2016, 31:366-374.
Wohnhaas et al., "DMSO cry opreservation is the method of choice to preserve cells for droplet-based single-cell RNA sequencing," Scientific Reports, Jul. 2019, 9(1):10699, 14 pages.
Zhang et al., "Genome-wide open chromatin regions and their effects on the regulation of silk protein genes in Bombyx mori," Sci Rep., Oct. 2017, 7(1):12919, 9 pages.
Arslan et al., "Engineering of a superhelicase through conformational control (Supplementary Materials)," Science, Apr. 17, 2015, 348(6232):344-347, 18 pages.
Arslan et al., "Engineering of a superhelicase through conformational control," Science, Apr. 17, 2015, 348(6232):344-347.
Baner et al., "Signal amplification of padlock probes by rolling circle replication," Nucleic Acids Res., 1998, 26(22):5073-5078.
Borm et al., "High throughput Human embryo spatial transcriptome mapping by surface transfer of tissue RNA," Abstracts Selected Talks, Single Cell Genomics mtg, (SCG2019), 2019, 1 pages (Abstract Only).
Chen et al., "Efficient in situ barcode sequencing using padlock probe-based BaristaSeq," Nucleic Acids Res., 2018, 46(4): e22, 11 pages.
Chen et al., "Large field of view-spatially resolved transcriptomics at nanoscale resolution," bioRxiv, Jan. 19, 2021, retrieved from URL <https://www.biorxiv.org/node/1751045.abstract>, 37 pages.
Codeluppi et al., "Spatial organization of the somatosensory cortex revealed by osmFISH," Nature Methods, Nov. 2018, 15:932-935.
Dean et al., "Rapid Amplification Of Plasmid And Phage DNA Using Phi29 DNA Polymerase And Multiply-Primed Rolling Circle Amplification," Genome Research, Jun. 2001, 11:1095-1099.
Ergin et al., "Proteomic Analysis of PAXgene-Fixed Tissues," J Proteome Res., 2010, 9(10):5188-96.
Faruqi et al., "High-throughput genotyping of single nucleotide polymorphisms with rolling circle amplification," BMC Genomics, Aug. 2001, 2:4, 10 pages.
Gao et al., "A highly homogeneous expansion microscopy polymer composed of tetrahedron-like monomers," bioRxiv, Oct. 22, 2019, 23 pages (Preprint).
Gilar et al., "Study of phosphorothioate-modified oligonucleotide resistance to 3'-exonuclease using capillary electrophoresis," J ChromatogrB Biomed Sci Appl., Aug. 28, 1998, 714(1):13-20.
Goransson et al., "A single molecule array for digital targeted molecular analyses," Nucleic Acids Res., Nov. 25, 2009, 37(1):e7, 9 pages.
Li et al., "A new GSH-responsive prodrug of 5-aminolevulinic acid for photodiagnosis and photodynamic therapy of tumors," European Journal of Medicinal Chemistry, Nov. 2019, 181:111583, 9 pages.
Mathieson et al., "A Critical Evaluation of the PAXgene Tissue Fixation System: Morphology, Immunohistochemistry, Molecular Biology, and Proteomics," Am J Clin Pathol., Jul. 8, 2016, 146(1):25-40.
Mohsen et al., "The Discovery of Rolling Circle Amplification and Rolling Circle Transcription," Acc Chem Res., Nov. 15, 2016, 49(11):2540-2550, 25 pages.
Schweitzer et al., "Immunoassays with rolling circle DNA amplification: A versatile platform for ultrasensitive antigen detection," Proc. Natl Acad. Sci. USA, May 22, 2000, 97:10113-119.
Xia et al., "Spatial transcriptome profiling by MERFISH reveals subcellular RNA compartmentalization and cell cycle-dependent gene expression", Proceedings of the National Academy of Sciences, Sep. 2019, 116(39):19490-19499.
Nallur et al., "Signal amplification by rolling circle amplification on DNA microarrays," Nucleic Acids Res., Dec. 1, 2001, 29(23):e118, 9 pages.
Raj et al., "Imaging individual mRNA molecules using multiple singly labeled probes," Nature Methods, Oct. 2008, 5(10):877-879, 9 pages.
Appella, "Non-natural nucleic acids for synthetic biology," Current Opinion in Chemical Biology, Dec. 2009, 13(5-6): 687-696.
Bunt et al., "FRET from single to multiplexed signaling events," Biophys Rev. Apr. 2017, 9(2):119-129.
Cho et al., "Seq-Scope: Submicrometer-resolution spatial transcriptomics for single cell and subcellular studies," Cell, Jun. 24, 2021, 184:3359-3572, 37 pages.
Eng et al., "Transcriptome-scale super-resolved imaging in tissues by RNA seqFISH+," Nature, Apr. 2019, 568(7751):235-239, 37 pages.
Goh et al., "Highly Specific Multiplexed RNA Imaging In Tissues With Split-FISH," Nat Methods, Jun. 15, 2020, 17(7):689-693, 21 pages.
Grünweller et al., "Locked Nucleic Acid Oligonucleotides," BioDrugs, Jul. 2007, 21(4): 235-243.
Gu et al., "Multiplex single-molecule interaction profiling of DNA-barcoded proteins," Nature, Sep. 21, 2014, 515:554-557.
Liu et al., "High-Spatial-Resolution Multi-Omics Sequencing via Deterministic Barcoding in Tissue," Cell, Nov. 13, 2020, 183(6):1665-1681, 36 pages.
Liu et al., "Spatial transcriptome sequencing of FFPE tissues at cellular level," bioRxiv 788992, Oct. 14, 2020, 39 pages.
Ma et al., "Isothermal amplification method for next-generation sequencing," PNAS, Aug. 12, 2013, 110(35):14320-14323.
Orenstein et al., "γPNA FRET Pair Miniprobes for Quantitative Fluorescent In Situ Hybridization to Telomeric DNA in Cells and Tissue," Molecules, Dec. 2, 2017, 22(12):2117, 15 pages.
Takei et al., "Integrated Spatial Genomics Reveals Global Architecture Of Single Nuclei," Nature, Jan. 27, 2021, 590(7845):344-350, 53 pages.
Vickovic et al., "SM-Omics: An automated Platform for High-Throughput Spatial Multi-Omics," bioRxiv, Oct. 2020, 40 pages.
Zahra et al., "Assessment of Different Permeabilization Methods of Minimizing Damage to the Adherent Cells for Detection of Intracellular RNA by Flow Cytometry," Avicenna Journal of Medical Biotechnology, Jan. 1, 2014, 6(1):38-46.
Goldmeyer et al., "Development of a novel one-tube isothermal reverse transcription thermophilic helicase-dependent amplification platform for rapid RNA detection," Journal of Molecular Diagnostics, American Society for Investigative Pathology and the Association for Molecular Pathology, Nov. 1, 2007, 9(5):639-644.

ENHANCING SPECIFICITY OF ANALYTE BINDING

CROSS-REFERENCE TO RELATED APPLICATIONS

Pursuant to 35 U.S.C. § 119(e), this application is a continuation of International Application PCT/US2020/059472, with an international filing date of Nov. 6, 2020, which claims priority to U.S. Provisional Patent Application No. 63/040,292, filed Jun. 17, 2020, and U.S. Provisional Patent Application No. 62/933,299, filed Nov. 8, 2019. The contents of each of these applications are incorporated herein by reference in their entireties.

SEQUENCE LISTING

This application contains a Sequence Listing that has been submitted electronically as an ASCII text file named 47706-0234001_SL_ST25.txt. The ASCII text file, created on Sep. 29, 2022, is 1,406 bytes in size. The material in the ASCII text file is hereby incorporated by reference in its entirety.

BACKGROUND

Cells within a tissue of a subject have differences in cell morphology and/or function due to varied analyte levels (e.g., gene and/or protein expression) within the different cells. The specific position of a cell within a tissue (e.g., the cell's position relative to neighboring cells or the cell's position relative to the tissue microenvironment) can affect, e.g., the cell's morphology, differentiation, fate, viability, proliferation, behavior, and signaling and cross-talk with other cells in the tissue.

Spatial heterogeneity has been previously studied using techniques that only provide data for a small handful of analytes in the context of an intact tissue or a portion of a tissue, or provide a lot of analyte data for single cells, but fail to provide information regarding the position of the single cell in a parent biological sample (e.g., tissue sample).

Increasing resolution of spatial heterogeneity can be achieved by increasing capture efficiency or by reducing background signal. This is usually achieved by relying on the affinity of the capture reagents and/or optimized reaction conditions, neither of which address methods with a second capture step, for example, when using antibody attached oligonucleotides to target an analyte. Therefore, there remains a need to develop strategies to enhance the specificity of binding to target analytes when a second capture step is involved.

SUMMARY

This disclosure features improvements to a spatial heterogeneity workflow that includes a step of reversibly blocking capture binding domains until a user prefers to expose it to a plurality of capture probes.

In one aspect, this disclosure features a method for identifying the location of an analyte in a biological sample comprising (a) contacting the biological sample with a substrate comprising a plurality of capture probes comprising a spatial barcode and a capture domain; (b) binding an analyte-binding moiety to the analyte, wherein the analyte-binding moiety is associated with an oligonucleotide comprising an analyte-binding-moiety barcode and a capture binding domain that hybridizes to the capture domain of the capture probe, wherein a portion of the capture binding domain is blocked; (c) releasing the blocking probe from the capture binding domain and hybridizing the capture binding domain to the capture domain; and (d) determining (i) all or a part of the sequence of the oligonucleotide bound to the capture domain, or a complement thereof, and (ii) all or a part of the sequence of the spatial barcode, or a complement thereof, and using the determined sequence of (i) and (ii) to identify a location of the analyte in the biological sample. In some instances, the method includes further determining the abundance of the analyte in the biological sample. In some instances, the capture binding domain is blocked using a blocking probe. In other instances, the capture binding domain is blocked using artificial nucleic acids such as plurality of caged nucleotides in the capture binding domain itself.

In some instances, also disclosed herein is a method for enhancing the binding of a capture binding domain to a capture domain of a capture probe comprising: (a) contacting a biological sample with a substrate comprising a plurality of capture probes comprising a spatial barcode and the capture domain; (b) binding an analyte-binding moiety to an analyte, wherein the analyte-binding moiety is associated with an oligonucleotide comprising an analyte-binding-moiety barcode and the capture binding domain, wherein a portion of the capture binding domain is blocked; and (c) releasing the blocking probe from the capture binding domain, thereby allowing the capture binding domain to hybridize to the capture domain; thereby enhancing the binding of the capture binding domain to the capture domain. In some instances, the capture binding domain is blocked using a blocking probe. In other instances, the capture binding domain is blocked using artificial nucleic acids such as plurality of caged nucleotides in the capture binding domain itself. In some instances, the method further includes determining (i) all or a part of the sequence of the oligonucleotide specifically bound to the capture domain, or a complement thereof, and (ii) all or a part of the sequence of the spatial barcode, or a complement thereof, and using the determined sequence of (i) and (ii) to identify a location of the analyte in the biological sample.

In one aspect, this disclosure features methods identifying the location and/or abundance of an analyte in a biological sample including: (a) contacting the biological sample with a substrate including a plurality of capture probes, wherein a capture probe of the plurality of capture probes includes a spatial barcode and a capture domain; (b) binding an analyte-binding moiety to the analyte, wherein the analyte-binding moiety is associated with an oligonucleotide including an analyte-binding-moiety barcode and a capture probe binding domain that hybridizes to the capture domain, wherein all or a portion of the capture probe binding domain is hybridized to a blocking probe; (c) releasing the blocking probe from the capture probe binding domain, thereby allowing the capture probe binding domain to hybridize to the capture domain; and (d) determining (i) all or a part of the sequence of the oligonucleotide specifically bound to the capture domain, or a complement thereof, and (ii) all or a part of the sequence of the spatial barcode, or a complement thereof, and using the determined sequence of (i) and (ii) to identify a location of the analyte in the biological sample.

In another aspect, this disclosure features methods for enhancing the specificity of binding of a capture probe binding domain to a capture domain including: (a) contacting a biological sample with a substrate including a plurality of capture probes, wherein a capture probe of the plurality of capture probes includes a spatial barcode and the capture domain; (b) binding an analyte-binding moiety to the analyte, wherein the analyte-binding moiety is associated with an oligonucleotide including an analyte-binding-moiety barcode and the capture probe binding domain that hybridizes to the capture domain, wherein all or a portion of the capture probe binding domain is hybridized to a blocking probe; and (c) releasing the blocking probe from the capture probe binding domain, thereby allowing the capture probe binding domain to hybridize to the capture domain; thereby enhancing the specificity of binding of the capture probe binding domain to the capture domain.

In another aspect, this disclosure features methods for enhancing the specificity of binding of an analyte-binding moiety to a target analyte in a biological sample where the method includes: (a) contacting the biological sample with a substrate, where the substrate includes a plurality of capture probes affixed to the substrate, where the capture probe includes a spatial barcode and the capture domain; (b) binding an analyte-binding moiety to a target analyte in the biological sample, where the analyte-binding moiety is associated with an oligonucleotide including a capture probe binding domain that hybridizes to a capture domain of a capture probe, where the capture probe binding domain is blocked and prevented from hybridizing to the capture domain of the capture probe affixed to the substrate; (c) releasing the block from the capture probe binding domain, thereby allowing the capture probe binding domain to specifically bind to the capture domain of the capture probe on the substrate, thereby enhancing the specificity of binding of an analyte-binding moiety to a target analyte in a biological sample. In some embodiments, the method further includes determining (i) all or a part of the sequence of the oligonucleotide specifically bound to the capture domain, or a complement thereof, and (ii) all or a part of the sequence of the spatial barcode, or a complement thereof, and using the determined sequence of (i) and (ii) to identify a location of the target analyte in the biological sample.

Also disclosed herein is a method for decreasing background binding on a substrate comprising: (a) contacting the biological sample with the substrate comprising a plurality of capture probes comprising a spatial barcode and a capture domain; (b) binding an analyte-binding moiety to the analyte, wherein the analyte-binding moiety is associated with an oligonucleotide comprising an analyte-binding-moiety barcode and a capture binding domain that hybridizes to the capture domain of the capture probe, wherein a portion of the capture binding domain is blocked; (c) releasing the blocking probe from the capture binding domain and hybridizing the capture binding domain to the capture domain; thereby decreasing background binding on a substrate. In some instances, the capture binding domain is blocked using a blocking probe. In other instances, the capture binding domain is blocked using artificial nucleic acids such as plurality of caged nucleotides in the capture binding domain itself.

In some embodiments, the analyte-binding moiety is a protein. In some embodiments, the protein is an antibody. In some embodiments, the antibody is a monoclonal antibody, recombinant antibody, synthetic antibody, a single domain antibody, a single-chain variable fragment (scFv), and or an antigen-binding fragment (Fab).

In some embodiments, the analyte-binding moiety is associated with the oligonucleotide via a linker. In some embodiments, the linker is a cleavable linker. In some embodiments, the cleavable linker is a photocleavable linker, UV-cleavable linker, or an enzyme-cleavable linker. In some embodiments, the cleavable linker is an enzyme cleavable linker.

In some embodiments, the method further includes releasing the oligonucleotide from the analyte-binding moiety. In some embodiments, the oligonucleotide includes a free 3' end.

In another aspect, the disclosure includes a method for identifying the location of an analyte in a biological sample comprising (a) contacting the biological sample with a substrate comprising a plurality of capture probes comprising a spatial barcode and a capture domain; (b) hybridizing a first probe oligonucleotide and a second probe oligonucleotide to the analyte, wherein the second probe oligonucleotide comprises a capture binding domain that hybridizes to the capture domain, wherein a portion of the capture probe domain is blocked; (c) ligating the first probe oligonucleotide and the second probe oligonucleotide, thereby creating the ligated probe, wherein the ligated probe is substantially complementary to the analyte; and (d) releasing: (i) the ligated probe from the analyte, and (ii) the blocking probe from the capture binding domain, thereby allowing the capture binding domain to bind to the capture domain of the capture probe on the substrate; and (e) determining (i) all or a part of the sequence of the ligated probe bound to the capture domain, or a complement thereof, and (ii) all or a part of the sequence of the spatial barcode, or a complement thereof, and using the determined sequence of (i) and (ii) to identify a location of the analyte in the biological sample. In some instances, the method includes further determining the abundance of the analyte in the biological sample. In some instances, the capture binding domain is blocked using a blocking probe. In other instances, the capture binding domain is blocked using artificial nucleic acids such as plurality of caged nucleotides in the capture binding domain itself.

In another aspect, the disclosure includes a method for enhancing the binding of a ligated probe to a capture domain comprising (a) contacting a biological sample with a substrate comprising a plurality of capture probes comprising a spatial barcode and the capture domain; (b) hybridizing a first probe oligonucleotide and a second probe oligonucleotide to an analyte, wherein the second probe oligonucleotide comprises a capture binding domain that hybridizes to the capture domain, wherein a portion of the capture binding domain is blocked; (c) ligating the first probe oligonucleotide and the second probe oligonucleotide, thereby creating the ligated probe, wherein the ligated probe is substantially complementary to the analyte; and (d) releasing: (i) the ligated probe from the analyte, and (ii) the blocking probe from the capture binding domain, thereby allowing the capture binding domain to bind to the capture domain of the capture probe on the substrate; thereby enhancing the binding of the ligated probed to the capture domain. In some instances, the method includes further determining the abundance of the analyte in the biological sample. In some instances, the capture binding domain is blocked using a blocking probe. In other instances, the capture binding domain is blocked using artificial nucleic acids such as plurality of caged nucleotides in the capture binding domain itself.

In some instances, the method further includes determining the abundance of the analyte in the biological sample. In some instances, the first probe oligonucleotide and the second probe oligonucleotide are substantially complementary to adjacent sequences of the analyte. In some instances, the method includes further determining (i) all or a part of the sequence of the ligated probe, or a complement thereof, and (ii) all or a part of the sequence of the spatial barcode, or a complement thereof, and using the determined sequence of (i) and (ii) to identify the location of the analyte in the biological sample.

In another aspect, this disclosure features methods for identifying the location and/or abundance of an analyte in a biological sample including: (a) contacting the biological sample with a substrate including a plurality of capture probes, wherein a capture probe of the plurality of capture probes includes a spatial barcode and a capture domain; (b) hybridizing a first probe oligonucleotide and a second probe oligonucleotide to the analyte, wherein: (i) the first probe oligonucleotide and the second probe oligonucleotide are substantially complementary to adjacent sequences of the analyte, and (ii) the second probe oligonucleotide includes a capture probe binding domain that hybridizes to the capture domain, wherein all or a portion of the capture probe binding domain is hybridized to a blocking probe, thereby preventing hybridization of the capture probe binding domain to the capture domain; (c) ligating the first probe oligonucleotide and the second probe oligonucleotide, thereby creating the ligated probe, wherein the ligated probe is substantially complementary to the analyte; and (d) releasing: (i) the ligated probe from the analyte, and (ii) the blocking probe from the capture probe binding domain, thereby allowing the capture probe binding domain to specifically bind to the capture domain of the capture probe on the substrate; thereby enhancing the specificity of binding of a polynucleotide to the analyte in a biological sample.

In another aspect, this disclosure features methods for enhancing the specificity of binding of a ligated probe to a capture domain including: (a) contacting a biological sample with a substrate including a plurality of capture probes, wherein a capture probe of the plurality of capture probes includes a spatial barcode and the capture domain; (b) hybridizing a first probe oligonucleotide and a second probe oligonucleotide to the analyte, wherein: (i) the first probe oligonucleotide and the second probe oligonucleotide are substantially complementary to adjacent sequences of the analyte, and (ii) the second probe oligonucleotide includes a capture probe binding domain that hybridizes to the capture domain, wherein all or a portion of the capture probe binding domain is hybridized to a blocking probe, thereby preventing hybridization of the capture probe binding domain to the capture domain; (c) ligating the first probe oligonucleotide and the second probe oligonucleotide, thereby creating the ligated probe, wherein the ligated probe is substantially complementary to the analyte; and (d) releasing: (i) the ligated probe from the analyte, and (ii) the blocking probe from the capture probe binding domain, thereby allowing the capture probe binding domain to specifically bind to the capture domain of the capture probe on the substrate; thereby enhancing the specificity of binding of a polynucleotide to the analyte in a biological sample.

In some instances, also disclosed is a method for decreasing background binding on a substrate comprising: (a) contacting a biological sample with a substrate comprising a plurality of capture probes comprising a spatial barcode and a capture domain; (b) hybridizing a first probe oligonucleotide and a second probe oligonucleotide to an analyte, wherein the second probe oligonucleotide comprises a capture binding domain that hybridizes to the capture domain, wherein a portion of the capture binding domain is hybridized to a blocking probe; (c) ligating the first probe oligonucleotide and the second probe oligonucleotide, thereby creating the ligated probe, wherein the ligated probe is substantially complementary to the analyte; and (d) releasing: (i) the ligated probe from the analyte, and (ii) the blocking probe from the capture binding domain, thereby allowing the capture binding domain to bind to the capture domain of the capture probe on the substrate; thereby decreasing background binding on a substrate. In some instances, the capture binding domain is blocked using a blocking probe. In other instances, the capture binding domain is blocked using artificial nucleic acids such as plurality of caged nucleotides in the capture binding domain itself. In some instances, the methods further comprise determining (i) all or a part of the sequence of the oligonucleotide specifically bound to the capture domain, or a complement thereof, and (ii) all or a part of the sequence of the spatial barcode, or a complement thereof, and using the determined sequence of (i) and (ii) to identify a location of the analyte in the biological sample.

In another aspect, this document features methods for enhancing the specificity of binding of a first analyte-binding moiety to a first target analyte and a second analyte binding moiety to a second target analyte in a biological sample where the method includes: (a) contacting the biological sample with a substrate, where the substrate includes a plurality of capture probe affixed to the substrate, where the capture probe includes a spatial barcode and a capture domain; (b) binding a first analyte-binding moiety to a first target analyte in the biological sample, where the first analyte-binding moiety is associated with a first oligonucleotide including: (i) a first barcode that identifies the first analyte-binding moiety; and (ii) a first bridge sequence; (c) binding a second analyte-binding moiety to a second target analyte in the biological sample, where the second analyte-binding moiety is bound to a second oligonucleotide including: (i) a capture probe binding domain that binds to a capture domain on a capture probe, (ii) a second barcode that identifies second analyte-binding moiety; and (iii) a second bridge sequence; where the capture probe binding domain is blocked and prevented from hybridizing to the capture domain of the capture probe affixed to the substrate; (d) contacting the biological sample with a third oligonucleotide; (e) hybridizing the third oligonucleotide to the first bridge sequence of the first oligonucleotide and the second bridge sequence of the second oligonucleotide; (f) ligating the first oligonucleotide and the second oligonucleotide, thereby creating a ligated probe; and (g) releasing the block from the capture probe binding domain, thereby allowing the capture probe binding domain of the second oligonucleotide to specifically bind to the capture domain of the capture probe on the substrate; thereby enhancing the specificity of binding of a first analyte-binding moiety to a first target analyte and a second analyte binding moiety to a second target analyte in a biological sample.

In some embodiments, in the methods disclosed herein, the first analyte-binding moiety is a first protein. In some embodiments, the first protein is a first antibody. In some embodiments, the first antibody is a monoclonal antibody, recombinant antibody, synthetic antibody, a single domain antibody, a single-chain variable fragment (scFv), and or an antigen-binding fragment (Fab). In some embodiments, the first analyte-binding moiety is associated with the first oligonucleotide via a first linker. In some embodiments, the first linker is a cleavable linker.

In some embodiments, the first cleavable linker is a photocleavable linker, UV-cleavable linker, or an enzyme-cleavable linker. In some embodiments, the first cleavable linker is an enzyme cleavable linker.

In some instances, the first probe oligonucleotide comprises at least two ribonucleic acid bases at the 3' end, and wherein the second probe oligonucleotide comprises a phosphorylated nucleotide at the 5' end. In some instances, the first probe oligonucleotide and the second probe oligonucleotide are DNA probes.

In some embodiments, the first oligonucleotide includes a free 3' end. In some embodiments, the first oligonucleotide includes from 5' to 3': a first barcode and a first bridge sequence. In some embodiments, the first oligonucleotide includes from 5' to 3': a primer sequence, a first barcode, and a first bridge sequence.

In some embodiments, the second analyte-binding moiety is a second protein. In some embodiments, the second protein is a second antibody. In some embodiments, the second antibody is a monoclonal antibody, recombinant antibody, synthetic antibody, a single domain antibody, a single-chain variable fragment (scFv), and or an antigen-binding fragment (Fab).

In some embodiments, the second analyte-binding moiety is associated with the second oligonucleotide via a second linker. In some embodiments, the second linker is a second cleavable linker. In some embodiments, the second cleavable linker is a photocleavable linker, UV-cleavable linker, or an enzyme-cleavable linker. In some embodiments, the second cleavable linker is an enzyme cleavable linker.

In some embodiments, the second oligonucleotide includes a free 5' end. In some embodiments, the second oligonucleotide includes a phosphorylated nucleotide at the 5' end. In some embodiments, the second oligonucleotide includes from 3' to 5': a capture probe binding domain, a second barcode, and a second bridge sequence.

In some embodiments, the first analyte and the second analyte are the same. In some embodiments, the first analyte and the second analyte are different.

In some embodiments, the third oligonucleotide includes a sequence that is partially complementary to the first bridge sequence. In some embodiments, the third oligonucleotide includes a sequence that is partially complementary to the second bridge sequence.

In some embodiments, the ligation step includes ligating (i) the first oligonucleotide and the second oligonucleotide using enzymatic or chemical ligation. In some embodiments, the enzymatic ligation utilizes a ligase. In some embodiments, the ligase is one or more of a T4 RNA ligase (Rnl2), a SplintR® ligase, a single stranded DNA ligase, or a T4 DNA ligase. In some embodiments, the ligase is a T4 RNA ligase 2 (Rnl2) ligase. In some embodiments, the method further includes releasing the ligated probe.

In some embodiments, the releasing includes removing the first oligonucleotide from the first analyte-binding moiety. In some embodiments, the releasing includes removing the second oligonucleotide from the second analyte-binding moiety.

In another aspect, this disclosure features methods for enhancing the specificity of binding of an oligonucleotide to a target analyte in a biological sample where the method includes: (a) contacting the biological sample with a substrate, where the substrate includes a plurality of capture probes affixed to the substrate, where the capture probe includes a spatial barcode and the capture domain; (b) binding a first probe oligonucleotide and a second probe oligonucleotide to a target analyte in the biological sample, where: the first probe oligonucleotide and the second probe oligonucleotide are substantially complementary to adjacent sequences of the analyte, the second probe oligonucleotide includes a capture probe binding domain that binds to a capture domain of a capture probe, where the capture probe binding domain is blocked and prevented from hybridizing to the capture domain of the capture probe affixed to the substrate; (c) ligating the first probe oligonucleotide and the second probe oligonucleotide, thereby creating a ligated probe that is substantially complementary to the analyte; (d) releasing: the ligated probe from the analyte, and the block from the capture probe binding domain, thereby allowing the capture probe binding domain to specifically bind to the capture domain of the capture probe on the substrate, thereby enhancing the specificity of binding of a polynucleotide to a target analyte in a biological sample.

In some embodiments, the method further includes determining (i) all or a part of the sequence of the ligated probe, or a complement thereof, and (ii) all or a part of the sequence of the spatial barcode, or a complement thereof, and using the determined sequence of (i) and (ii) to identify the location of the analyte in the biological sample.

In some embodiments, the first probe oligonucleotide includes at least two ribonucleic acid bases at the 3' end.

In some embodiments, the first and second probe oligonucleotides are DNA probes.

In some embodiments, the first probe oligonucleotide further includes a functional sequence. In some embodiments, the functional sequence is a primer sequence.

In some embodiments, the second probe oligonucleotide includes a phosphorylated nucleotide at the 5' end.

In some embodiments, the ligation step include ligating (i) the first probe oligonucleotide and the second probe oligonucleotide using enzymatic or chemical ligation. In some embodiments, the enzymatic ligation utilizes a ligase. In some embodiments, the ligase is one or more of a T4 RNA ligase (Rnl2), a SplintR® ligase, a single stranded DNA ligase, or a T4 DNA ligase. In some embodiments, the ligase is a T4 RNA ligase 2 (Rnl2) ligase.

In some instances, the blocking probe and the capture binding domain are two different (noncontiguous or separate) nucleotide sequences, wherein the capture binding domain comprises a first sequence substantially complementary to the capture domain. In some instances, the capture binding domain comprises a contiguous sequence comprising (i) a first sequence substantially complementary to the capture domain and (ii) the blocking probe.

In some embodiments, the capture probe binding domain includes a contiguous sequence including a first sequence substantially complementary to the capture domain of the capture probe and a second sequence substantially complementary to the first sequence, where the second sequence blocks first sequence of the capture probe binding domain from hybridizing to the capture domain of the capture probe. In some embodiments, the second sequence includes a sequence configured to hybridize to the first sequence capture probe binding domain. In some embodiments, the second sequence includes a sequence that is substantially complementary to the first sequence of the capture probe binding domain. In some embodiments, the second sequence includes a homopolymeric sequence that is substantially complementary to the first sequence of the capture probe binding domain. In some embodiments, the second sequence is configured to hybridize to a poly(A), poly(T) or a poly-rU sequence. In some embodiments, the second sequence includes a poly(U) sequence. In some embodiments, the first sequence includes a homopolymeric sequence. In some embodiments, first sequence includes a poly(A) sequence or a poly(T) sequence.

In some embodiments, the capture probe binding domain further includes a hairpin sequence. In some embodiments, the hairpin sequence is located 5' of the second sequence in the capture probe binding domain. In some embodiments, the capture probe binding domain includes from 5' to 3': a first sequence that is substantially complementary to the capture domain of the capture probe, a hairpin sequence, and a second sequence substantially complementary to the first sequence.

In some embodiments, the hairpin sequence include a sequence of about three nucleotides, about four nucleotides, about five nucleotides, about six nucleotides, about seven nucleotides, about eight nucleotides, about nine nucleotides or about 10 or more nucleotides.

In some embodiments, the hairpin sequence includes DNA, RNA, DNA-RNA hybrid, or modified nucleotides.

In some embodiments, the hairpin sequence includes a cleavable linker. In some embodiments, the cleavable linker is a photocleavable linker, UV-cleavable linker, or an enzyme-cleavable linker. In some embodiments, the enzyme that cleaves that enzymatic-cleavable domain is an endonuclease. In some embodiments, where the hairpin sequence includes a target sequence for a restriction endonuclease.

In some embodiments, releasing the second sequence from the first sequence includes contacting with a restriction endonuclease. In some embodiments, releasing the second sequence from the first sequence includes contacting the second sequence with an endoribonuclease.

In some embodiments, the endoribonuclease is one or more of RNase H, RNase A, RNase C, or RNase I. In some embodiments, the endoribonuclease is RNAseH. In some embodiments, the RNase H includes RNase H1, RNase H2, or RNase H1 and RNase H2.

In some embodiments, the hairpin sequence includes a homopolymeric sequence. In some embodiments, the hairpin sequence includes a poly(T) or poly(U) sequence. In some embodiments, hairpin sequence includes a poly(U) sequence.

In some embodiments, releasing the blocking domain (i.e., also called a second sequence herein) includes contacting the hairpin sequence with a Uracil-Specific Excision Reagent (USER) enzyme. In some embodiments, releasing the second sequence includes denaturing the second sequence.

In some embodiments, the hairpin sequence further includes a sequence that is capable of binding to a capture domain.

In some embodiments, the cleavage of the hairpin results in a single stranded sequence that is capable of binding to a capture probe binding domain on a spatial array.

In some embodiments, the capture probe binding domain includes a plurality of caged nucleotides, where a caged nucleotide of the plurality of caged nucleotides includes a caged moiety that blocks the capture probe binding domain from hybridizing to the capture domain of the capture probe. In some embodiments, releasing the caged moiety from the nucleotide includes activating the caged moiety, thereby by allowing the capture probe binding domain to specifically bind to the capture domain of the capture probe. In some embodiments, the activating the caged moiety includes photolysis of the caged moiety from the nucleotide. In some embodiments, the activating includes exposing the caged moiety to light pulses, where the light is at a wavelength of about less than 360 nm. In some embodiments, the light at the wavelength of about 360 nm is produced by a UV light. In some embodiments, the UV light originates from a fluorescence microscope, a UV laser, or a UV flashlamp.

Also disclosed herein is a method for identifying the location of an analyte in a biological sample comprising: (a) contacting the biological sample with a substrate comprising a plurality of capture probes comprising a spatial barcode and a capture domain; (b) binding an analyte-binding moiety to the analyte, wherein the analyte-binding moiety is associated with an oligonucleotide comprising an analyte-binding-moiety barcode and a capture binding domain that hybridizes to the capture domain of the capture probe, wherein the capture binding domain comprises a plurality of caged nucleotides, wherein a caged nucleotide of the plurality of caged nucleotides comprises a caged moiety that blocks the capture binding domain from hybridizing to the capture domain; (c) releasing the caged moiety from the capture binding domain and hybridizing the capture binding domain to the capture domain; and (d) determining (i) all or a part of the sequence of the oligonucleotide bound to the capture domain, or a complement thereof, and (ii) all or a part of the sequence of the spatial barcode, or a complement thereof, and using the determined sequence of (i) and (ii) to identify a location of the analyte in the biological sample.

In some instances, disclosed herein is a method for identifying the location of an analyte in a biological sample comprising: (a) contacting the biological sample with a substrate comprising a plurality of capture probes comprising a spatial barcode and a capture domain; (b) hybridizing a first probe oligonucleotide and a second probe oligonucleotide to the analyte, wherein the second probe oligonucleotide comprises a capture binding domain that hybridizes to the capture domain, wherein the capture binding domain comprises a plurality of caged nucleotides, wherein a caged nucleotide of the plurality of caged nucleotides comprises a caged moiety that blocks the capture binding domain from hybridizing to the capture domain; (c) ligating the first probe oligonucleotide and the second probe oligonucleotide, thereby creating the ligated probe, wherein the ligated probe is substantially complementary to the analyte; and (d) releasing: (i) the ligated probe from the analyte, and (ii) the caged moiety from the capture binding domain, thereby allowing the capture binding domain to bind to the capture domain of the capture probe on the substrate; and (e) determining (i) all or a part of the sequence of the ligated probe bound to the capture domain, or a complement thereof, and (ii) all or a part of the sequence of the spatial barcode, or a complement thereof, and using the determined sequence of (i) and (ii) to identify a location of the analyte in the biological sample. In some instances, the method further includes determining the abundance of the analyte in the biological sample. In some instances, the first probe oligonucleotide and the second probe oligonucleotide are substantially complementary to adjacent sequences of the analyte.

In some embodiments, the caged nucleotide includes a caged moiety selected from the group consisting of 6-nitropiperonyloxymethy (NPOM), 1-(ortho-nitrophenyl)-ethyl (NPE), 2-(ortho-nitrophenyl) propyl (NPP), diethylaminocoumarin (DEACM), and nitrodibenzofuran (NDBF). In some embodiments, the caged nucleotide includes a non-naturally-occurring nucleotide selected from the group consisting of 6-nitropiperonyloxymethy (NPOM)-caged guanosine, 6-nitropiperonyloxymethy (NPOM)-caged uridine, and 6-nitropiperonyloxymethy (NPOM)-caged thymidine.

In some embodiments, the capture probe binding domain includes one caged nucleotide, two caged nucleotides, three caged nucleotides, four caged nucleotides, five caged nucleotides, six caged nucleotides, seven caged nucleotides, eight caged nucleotides, nine caged nucleotides, or ten or more caged nucleotides.

In some embodiments, the capture probe binding domain includes a caged nucleotide at the 3' end. In some embodiments, the capture probe binding domain includes two caged nucleotides at the 3' end. In some embodiments, the capture probe binding domain includes at least three caged nucleotides at the 3' end. In some embodiments, the capture probe binding domain includes a caged nucleotide at the 5' end. In some embodiments, the capture probe binding domain includes two caged nucleotides at the 5' end. In some embodiments, the capture probe binding domain includes at least three caged nucleotides at the 5' end. In some embodiments, the capture probe binding domain includes a caged nucleotide at every odd position starting at the 3' end or starting at the 5' end. In some embodiments, the capture probe binding domain includes a sequence including at least 10%, at least, 20%, at least 30%, at least 40%, at least 50%, at least 60%, at least 70%, at least 80%, or at least 90% caged nucleotides.

In some embodiments, the analyte, the first analyte, or the second analyte is a protein. In some embodiments, the protein is an antibody. In some embodiments, the analyte is RNA. In some embodiments, the RNA is an mRNA.

In some instances, disclosed herein is a kit comprising: (a) a substrate comprising a plurality of capture probes comprising a spatial barcode and a capture domain; (b) a system comprising: (i) a plurality of an analyte binding moieties, wherein an analyte-binding moiety of the plurality is associated with an oligonucleotide comprising an analyte-binding-moiety barcode and the capture binding domain, or (ii) a plurality of first probe oligonucleotides and second probe oligonucleotides, wherein a first probe oligonucleotide and a second probe oligonucleotide each comprises sequences that are substantially complementary to an analyte, and wherein the second probe oligonucleotide comprises a capture binding domain; (c) a plurality of blocking probes; and (d) instructions for performing the method of any one of the preceding claims.

In some instances, also disclosed is a kit comprising: (a) a substrate comprising a plurality of capture probes comprising a spatial barcode and a capture domain; (b) a system comprising: (i) a plurality of an analyte binding moieties, wherein an analyte-binding moiety of the plurality is associated with an oligonucleotide comprising an analyte-binding-moiety barcode and the capture binding domain, wherein the capture binding domain comprises a plurality of caged nucleotides, wherein a caged nucleotide of the plurality of caged nucleotides comprises a caged moiety that blocks the capture binding domain from hybridizing to the capture domain, or (ii) a plurality of first probe oligonucleotides and second probe oligonucleotides, wherein a first probe oligonucleotide and a second probe oligonucleotide each comprises sequences that are substantially complementary to an analyte, and wherein the second probe oligonucleotide comprises a capture binding domain, wherein the capture binding domain comprises a plurality of caged nucleotides, wherein a caged nucleotide of the plurality of caged nucleotides comprises a caged moiety that blocks the capture binding domain from hybridizing to the capture domain; and (c) instructions for performing the method of any one of the preceding claims.

All publications, patents, patent applications, and information available on the internet and mentioned in this specification are herein incorporated by reference to the same extent as if each individual publication, patent, patent application, or item of information was specifically and individually indicated to be incorporated by reference. To the extent publications, patents, patent applications, and items of information incorporated by reference contradict the disclosure contained in the specification, the specification is intended to supersede and/or take precedence over any such contradictory material.

Where values are described in terms of ranges, it should be understood that the description includes the disclosure of all possible sub-ranges within such ranges, as well as specific numerical values that fall within such ranges irrespective of whether a specific numerical value or specific sub-range is expressly stated.

The term "each," when used in reference to a collection of items, is intended to identify an individual item in the collection but does not necessarily refer to every item in the collection, unless expressly stated otherwise, or unless the context of the usage clearly indicates otherwise.

Various embodiments of the features of this disclosure are described herein. However, it should be understood that such embodiments are provided merely by way of example, and numerous variations, changes, and substitutions can occur to those skilled in the art without departing from the scope of this disclosure. It should also be understood that various alternatives to the specific embodiments described herein are also within the scope of this disclosure.

DESCRIPTION OF DRAWINGS

The following drawings illustrate certain embodiments of the features and advantages of this disclosure. These embodiments are not intended to limit the scope of the appended claims in any manner. Like reference symbols in the drawings indicate like elements.

DETAILED DESCRIPTION

I. Introduction

Figure 1:
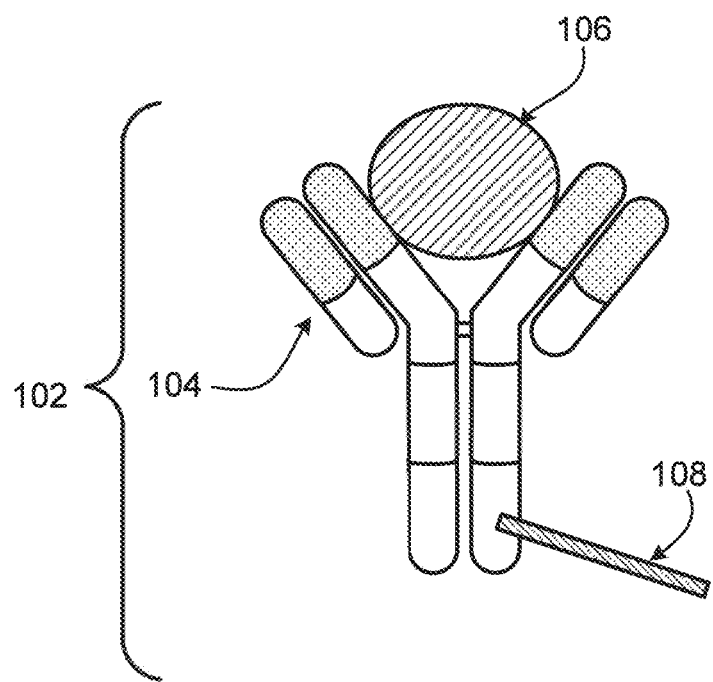
FIG. 1 is a schematic diagram of an exemplary analyte capture agent.

Spatial analysis methodologies can provide a vast amount of analyte level and/or expression data for a variety of multiple analytes within a sample at high spatial resolution, e.g., while retaining the native spatial context. Spatial analysis methods can include, e.g., the use of a capture probe including a spatial barcode (e.g., a nucleic acid sequence that provides information as to the position of the capture probe within a cell or a tissue sample (e.g., mammalian cell or a mammalian tissue sample) and a capture domain that is capable of binding to an analyte (e.g., a protein and/or nucleic acid) produced by and/or present in a cell.

Spatial analysis allows for the binding of analytes within a biological sample to capture domains. Oftentimes, both the analyte of interest and the capture domain of the capture probe are oligonucleotides. For example, an mRNA from a cell, a proxy of an mRNA, or another nucleic acid that can be used to identify the presence of the mRNA in a sample binds to a poly(T) sequence of a capture domain. By doing so, spatial analysis is able to determine where spatially that mRNA is being expressed in a sample and approximately how much of the mRNA is present at high resolution. Oftentimes there is background noise in such a system, for example background binding of the analyte, analyte proxy, or other analyte identifier to areas of the array, for example to capture domains that are not under the tissue but instead are on the array surface that is not covered by a tissue.

The disclosed methods provide solutions to the problem of background binding by inhibiting the interaction of the analytes with the capture domains and relieving that inhibition when analyte binding for spatial analysis is desired, thereby enhancing the specificity of the analytes binding in their spatial location.

Tissues and cells can be obtained from any source. For example, tissues and cells can be obtained from single-cell or multicellular organisms (e.g., a mammal). Tissues and cells obtained from a mammal, e.g., a human, often have varied analyte levels (e.g., gene and/or protein expression) which can result in differences in cell morphology and/or function. The position of a cell or a subset of cells (e.g., neighboring cells and/or non-neighboring cells) within a tissue can affect, e.g., the cell's fate, behavior, morphology, and signaling and cross-talk with other cells in the tissue. Information regarding the differences in analyte levels (gene and/or protein expression) within different cells in a tissue of a mammal can also help physicians select or administer a treatment that will be effective and can allow researchers to identify and elucidate differences in cell morphology and/or cell function in the single-cell or multicellular organisms (e.g., a mammal) based on the detected differences in analyte levels within different cells in the tissue. Differences in analyte levels within different cells in a tissue of a mammal can also provide information on how tissues (e.g., healthy and diseased tissues) function and/or develop.

Non-limiting aspects of spatial analysis methodologies are described in WO 2011/127099, WO 2014/210233, WO 2014/210225, WO 2016/162309, WO 2018/091676, WO 2012/140224, WO 2014/060483, WO 2020/176788 U.S. Pat. Nos. 10,002,316, 9,727,810, U.S. Patent Application Publication No. 2020/0277663, U.S. Patent Application Publication No. 2017/0016053, Rodrigues et al., Science 363(6434):1463-1467, 2019; WO 2018/045186, Lee et al., Nat. Protoc. 10(3):442-458, 2015; WO 2016/007839, WO 2018/045181, WO 2014/163886, Trejo et al., PLoS ONE 14(2):e0212031, 2019, U.S. Patent Application Publication No. 2018/0245142, Chen et al., Science 348(6233):aaa6090, 2015, Gao et al., BMC Biol. 15:50, 2017, WO 2017/144338, WO 2018/107054, WO 2017/222453, WO 2019/068880, WO 2011/094669, U.S. Pat. Nos. 7,709,198, 8,604,182, 8,951,726, 9,783,841, 10,041,949, WO 2016/057552, WO 2017/147483, WO 2018/022809, WO 2016/166128, WO 2017/027367, WO 2017/027368, WO 2018/136856, WO 2019/075091, U.S. Pat. No. 10,059,990, WO 2018/057999, WO 2015/161173, and Gupta et al., Nature Biotechnol. 36:1197-1202, 2018, each of which is incorporated by reference in its entirety, and can be used herein in any combination. Further non-limiting aspects of spatial analysis methodologies are described herein.

Some general terminology that may be used in this disclosure can be found WO 2020/176788 and/or U.S. Patent Application Publication No. 2020/0277663, each of which is incorporated by reference in its entirety. Typically, a "barcode" is a label, or identifier, that conveys or is capable of conveying information (about an analyte in a sample, a bead, and/or a capture probe. A barcode can be part of an analyte, or independent of an analyte. A barcode can be attached to an analyte. A particular barcode can be unique relative to other barcodes. For the purpose of this disclosure, an "analyte" can include any biological substance, structure, moiety, or component to be analyzed. The term "target" can similarly refer to an analyte of interest. Analytes can be broadly classified into one of two groups: nucleic acid analytes, and non-nucleic acid analytes. Examples of non-nucleic acid analytes include, but are not limited to, lipids, carbohydrates, peptides, proteins, glycoproteins (N-linked or O-linked), lipoproteins, phosphoproteins, specific phosphorylated or acetylated variants of proteins, amidation variants of proteins, hydroxylation variants of proteins, methylation variants of proteins, ubiquitylation variants of proteins, sulfation variants of proteins, viral coat proteins, extracellular and intracellular proteins, antibodies, and antigen binding fragments. In some embodiments, the analyte(s) can be localized to subcellular location(s), including, for example, organelles, e.g., mitochondria, Golgi apparatus, endoplasmic reticulum, chloroplasts, endocytic vesicles, exocytic vesicles, vacuoles, lysosomes, etc. In some embodiments, analyte(s) can be peptides or proteins, including without limitation antibodies and enzymes. Additional examples of analytes can be found in WO 2020/176788 and/or U.S. Patent Application Publication No. 2020/0277663, each of which is incorporated by reference in its entirety.

A "biological sample" is typically obtained from the subject for analysis using any of a variety of techniques including, but not limited to, biopsy, surgery, and laser capture microscopy (LCM), and generally includes cells and/or other biological material from the subject. In some embodiments, a biological sample can be a tissue section. In some embodiments, a biological sample can be a fixed and/or stained biological sample (e.g., a fixed and/or stained tissue section). In some embodiments biological sample can be a cell culture sample. In some embodiments, a biological sample can be nervous tissue, blood, serum, plasma, cerebrospinal fluid, or bone marrow aspirate. Biological samples are also described in WO 2020/176788 and/or U.S. Patent Application Publication No. 2020/0277663, each of which is incorporated by reference in its entirety.

In addition, spatial analysis methods can be performed on various types of samples, including tissues (e.g., tissue slices) or single cells (e.g., cultured cells). Exemplary methods and compositions relating to tissue or single-cell spatial analysis is found at least in WO 2020/176788 and/or U.S. Patent Application Publication No. 2020/0277663, each of which is incorporated by reference in its entirety. In some instances, one biological sample can be used for tissue and single cell analysis. For example, multiple serial slices (e.g., 10 µm in thickness) of a tissue can be cut. A first slice can be placed on an array and analyte capture as described herein can be performed. In some instances, a second slice of tissue can further undergo cellular dissociation, creating a sample with isolated cells that can be analyzed using spatial analysis methods. Briefly, in some instances, a tissue is minced into small pieces and treated with lysis buffer to homogenize the sample. The homogenous resultant can be filtered and centrifuged to collect a pellet of nuclei. The nuclei can be resuspended and used for single cell analysis methods described herein. Data captured from the second slice (i.e., the single nuclei data) could then be combined with the data from the first slice (i.e., the whole tissue data) to gain a higher cell type understanding and potentially deconvolve the cell type identity within each spot on the array. Additional methods of single cell isolation is found in Hu et al., Mol Cell. 2017 Dec. 7; 68(5):1006-1015.e7; Habib et al., Science, 2016 Aug. 26; 353(6302):925-8; Habib et al., Nat Methods, 2017 October; 14(10):955-958; Lake et al., Science, 2016 Jun. 24; 352(6293):1586-90; and Lacar et al., Nat Commun, 2016 Apr. 19; 7:11022; each of which is incorporated by reference in its entirety.

In another embodiment, two different samples are collected, whereby one sample is analyzed with intact tissue and a second tissue undergoes cell dissociation. Results from each biological sample can be compared to gain a higher cell type understanding and potentially deconvolve the cell type identity within each spot on the array. Array-based spatial analysis methods involve the transfer of one or more analytes from a biological sample to an array of features on a substrate, where each feature is associated with a unique spatial location on the array. Subsequent analysis of the transferred analytes includes determining the identity of the analytes and the spatial location of each analyte within the biological sample. The spatial location of each analyte within the biological sample is determined based on the feature to which each analyte is bound on the array, and the feature's relative spatial location within the array.

Figure 8:
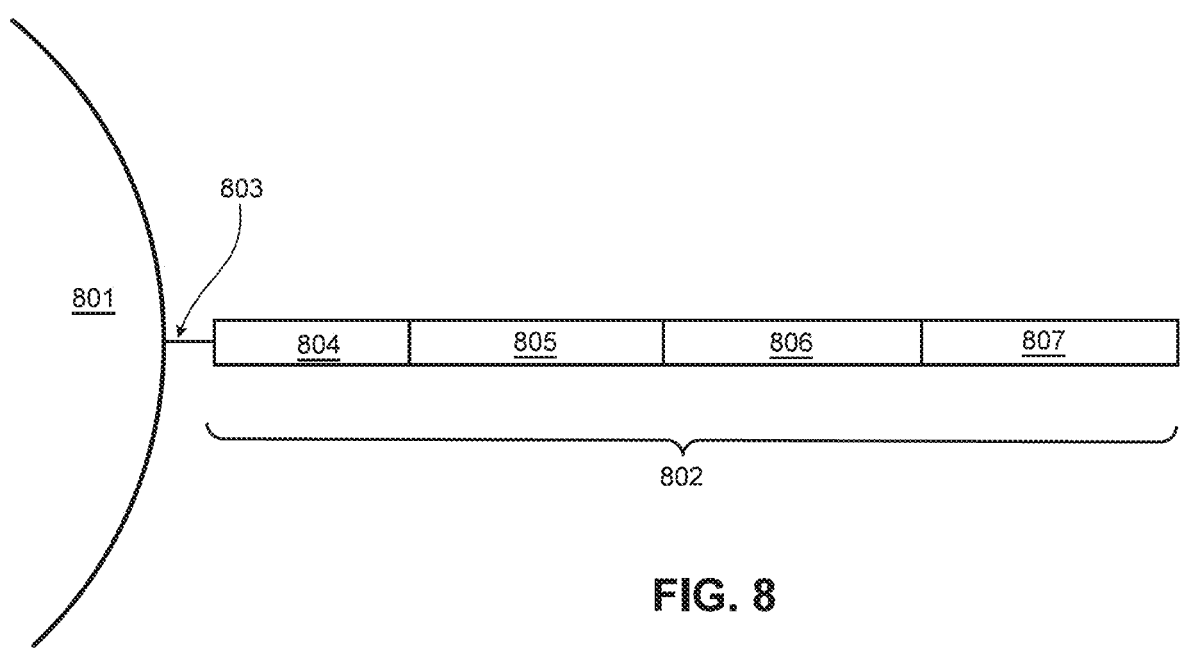
FIG. 8 is a schematic diagram showing an example of a barcoded capture probe, as described herein.

A "capture probe" refers to any molecule capable of capturing (directly or indirectly) and/or labelling an analyte (e.g., an analyte of interest) in a biological sample. In some embodiments, the capture probe is a nucleic acid or a polypeptide. In some embodiments, the capture probe includes a barcode (e.g., a spatial barcode and/or a unique molecular identifier (UMI)) and a capture domain. In some instances, the capture probe can include functional sequences that are useful for subsequent processing. As exemplified in FIG. 8, a capture probe 802 can be reversibly attached to a substrate 801 via a linker 803. The capture probe can include one or more functional sequences 804, which can include a sequencer specific flow cell attachment sequence, e.g., a P5 or P7 sequence, as well as functional sequence 806, which can include sequencing primer sequences, e.g., a R1 primer binding site, a R2 primer binding site. In some embodiments, sequence 804 is a P7 sequence and sequence 806 is a R2 primer binding site. A capture probe can additionally include a spatial barcode and/or unique molecular identifier 805 and a capture domain 807. The different sequences of the capture probe need not be in the sequential manner as depicted in this example, however the capture domain 807 should be placed in a location on the barcode wherein analyte capture and extension of the capture domain to create a copy of the analyte can occur. Additional features of capture probes are described in WO 2020/176788 and/or U.S. Patent Application Publication No. 2020/0277663, each of which is incorporated by reference in its entirety. Generation of capture probes can be achieved by any appropriate method, including those described in WO 2020/176788 and/or U.S. Patent Application Publication No. 2020/0277663, each of which is incorporated by reference in its entirety.

In some embodiments, more than one analyte type from a biological sample can be detected (e.g., simultaneously or sequentially) using any appropriate multiplexing technique, such as those described in WO 2020/176788 and/or U.S. Patent Application Publication No. 2020/0277663, each of which is incorporated by reference in its entirety.

In some embodiments, detection of one or more analytes (e.g., protein analytes) can be performed using one or more analyte capture agents. As used herein, an "analyte capture agent" refers to an agent that interacts with an analyte (e.g., an analyte in a sample) and with a capture probe (e.g., a capture probe attached to a substrate) to identify the analyte. In some embodiments, the analyte capture agent includes an analyte binding moiety and a capture agent barcode domain. Additional description of analyte capture agents can be found in WO 2020/176788 and/or U.S. Patent Application Publication No. 2020/0277663, each of which is incorporated by reference in its entirety.

There are at least two general methods to associate a spatial barcode with one or more neighboring cells, such that the spatial barcode identifies the one or more cells, and/or contents of the one or more cells, as associated with a particular spatial location. One general method is to promote analytes out of a cell and towards a spatially-barcoded array (e.g., including spatially-barcoded capture probes). Another general method is to cleave spatially-barcoded capture probes from an array and promote the spatially-barcoded capture probes towards and/or into or onto the biological sample.

In some cases, capture probes may be configured to prime, replicate, and consequently yield optionally barcoded extension products from a template (e.g., a DNA or RNA template), or derivatives thereof (see, e.g., WO 2020/176788 and/or U.S. Patent Application Publication No. 2020/0277663 regarding extended capture probes, the references of which are incorporated by reference in their entireties.). For example, in some cases, the capture probes may include mRNA specific priming sequences, e.g., poly-T primer segments that allow priming and replication of mRNA in a reverse transcription reaction or other targeted priming sequences. Alternatively or additionally, random RNA priming may be carried out using random N-mer primer segments of the barcoded oligonucleotides. Reverse transcriptases (RTs) can use an RNA template and a primer complementary to the 3' end of the RNA template to direct the synthesis of the first strand complementary DNA (cDNA). Additional variants of spatial analysis methods, including in some embodiments, an imaging step, are described in WO 2020/176788 and/or U.S. Patent Application Publication No. 2020/0277663, each of which is incorporated by reference in its entirety. Analysis of captured analytes, for example, including sample removal, extension of capture probes, sequencing (e.g., of a cleaved extended capture probe and/or a cDNA molecule complementary to an extended capture probe), sequencing on the array (e.g., using in situ hybridization approaches), temporal analysis, and/or proximity capture, is described in WO 2020/176788 and/or U.S. Patent Application Publication No. 2020/0277663. Some quality control measures are described in WO 2020/176788 and/or U.S. Patent Application Publication No. 2020/0277663, each of which is incorporated by reference in its entirety.

Typically, for spatial array-based analytical methods, a substrate functions as a support for direct or indirect attachment of capture probes to features of the array. A "feature" on an array acts as a locational support or repository for various molecular entities used in sample analysis. In some embodiments, some or all of the features in an array are functionalized for analyte capture. Exemplary substrates are described in WO 2020/176788 and/or U.S. Patent Application Publication No. 2020/0277663, each of which is incorporated by reference in its entirety. Exemplary features and geometric attributes of an array can be found in WO 2020/176788 and/or U.S. Patent Application Publication No. 2020/0277663, each of which is incorporated by reference in its entirety.

Generally, analytes can be captured when contacting a biological sample with a substrate including capture probes (e.g., substrate with capture probes embedded, spotted, printed on the substrate or a substrate with features (e.g., beads, wells) comprising capture probes). As used herein, "contact," "contacted," and/or "contacting," a biological sample with a substrate refers to any contact (e.g., direct or indirect) such that capture probes can interact (e.g., bind covalently or non-covalently (e.g., hybridize)) with analytes from the biological sample. Capture can be achieved actively (e.g., using electrophoresis) or passively (e.g., using diffusion). Analyte capture is further described in WO 2020/176788 and/or U.S. Patent Application Publication No. 2020/0277663, each of which is incorporated by reference in its entirety.

In some cases, a spatial analysis can be performed by attaching and/or introducing a molecule (e.g., a peptide, a lipid, or a nucleic acid molecule) having a barcode (e.g., a spatial barcode) to a biological sample (e.g., to a cell in a biological sample). In some embodiments, a plurality of molecules (e.g., a plurality of nucleic acid molecules) having a plurality of barcodes (e.g., a plurality of spatial barcodes) are introduced to a biological sample (e.g., to a plurality of cells in a biological sample) for use in spatial analysis. In some embodiments, after attaching and/or introducing a molecule having a barcode to a biological sample, the biological sample can be separated into single cells or cell groups for analysis. Some such methods of spatial analysis are described in WO 2020/176788 and/or U.S. Patent Application Publication No. 2020/0277663, each of which is incorporated by reference in its entirety.

Some exemplary spatial analysis workflows are described in WO 2020/176788 and/or U.S. Patent Application Publication No. 2020/0277663, each of which is incorporated by reference in its entirety.

In some embodiments, a spatial analysis can be performed using dedicated hardware and/or software, such as any of the systems described in WO 2020/176788 and/or U.S. Patent Application Publication No. 2020/0277663, each of which is incorporated by reference in its entirety.

II. Methods and Compositions for Enhancing the Specificity of Target Analyte Capture In some embodiments, provided herein are methods and materials for enhancing the specificity of binding of an antigen-binding moiety or a probe oligonucleotide to a target analyte in a biological sample by blocking the premature interactions between the antigen-binding moiety and/or probe oligonucleotide and a capture domain of a capture probe on a substrate. In instances without a blocking step, the capture binding domain (i.e., associated with the antigen-binding moiety or as a component of one of the probe oligonucleotides for RNA templated ligation) is capable of hybridizing to the capture domain of a probe affixed on a substrate instead of its target analyte thereby decreasing the sensitivity of an assay and creating background non-specific binding. For example, when using an antigen-binding moiety, the oligonucleotide of the moiety which comprises a capture domain complementary to the capture domain on the probe affixed to a substrate, if unblocked, can hybridize to the capture domain of the probe on a substrate surface before the antigen-binding moiety associates with its target analyte. In another example, for RNA-templated ligation an oligonucleotide probe used in RNA-templated ligation comprising a capture domain complementary to the capture domain on the probe affixed to a substrate can hybridize to the capture probe that is located on a substrate surface before (1) hybridization to an analyte of interest, (2) ligation of the oligonucleotides, or (3) both.

This disclosure describes solutions to these unwanted capture domain interactions by describing reversible methods that temporally block premature or unwanted hybridization of the capture binding domain of the analyte capture molecule and the capture probe on the surface of a substrate. The methods herein utilize one or more blocking probes to hybridize to a capture binding domain and temporarily block premature or unwanted hybridization. In some instances, the methods herein include steps of blocking a capture probe on a substrate. In some instances, the capture probe is blocked by any one of the blocking probes disclosed herein. In some instances, the capture probe is blocked at the capture domain. As used herein, a "blocking probe" is a molecule that affixes (e.g., hybridizes) to a capture binding domain and temporarily blocks premature or unwanted hybridization. A blocking probe can be a nucleic acid. In some instances, the blocking probe is a DNA molecule. In some instances, the blocking probe is an RNA molecule. In some instances, the blocking probe is a hybrid DNA-RNA molecule. The blocking probe can be synthetic or natural and as described herein, it can include one or more non-naturally occurring nucleotides. In some instances, the blocking probe includes full or partial (e.g., at least 70%, at least 75%, at least 80%, at least 85%, at least 90%, at least 91%, at least 92%, at least 93%, at least 94%, at least 95%, at least 96%, at least 97%, at least 98%, or at least 99%) complementarity to the capture binding domain. In some instances, the blocking probe is at least 2, at least 3, at least 4, at least 5, at least 6, at least 7, at least 8, at least 9, at least 10, at least about 15, at least about 20, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, or at least about 100 nucleotides in length. As such, the methods disclosed herein increase the efficiency of target analyte hybridization compared to methods that do not temporally block the capture binding domain. Further, the efficiency of downstream analyses (e.g., amplification and sequencing) using the methods disclosed herein is increased compared to methods that do not temporally block the capture binding domain because fewer false positive sequences are identified and sequenced. The methods disclosed herein are applicable to methods of detecting proteins or nucleic acids. For example, with respect to protein analyte detection, provided herein are methods for enhancing the specificity of binding of an analyte-binding moiety to a target analyte in a biological sample, where the antigen-binding moiety is attached to an oligonucleotide having at least an analyte-binding-moiety barcode and a capture binding domain that is complementary to a capture probe, and where the capture binding domain is blocked from hybridizing to a capture binding domain using either caged nucleotides or by a sequence complementary to the capture binding domain. In some instances, the sequence complementary to the capture binding domain is on the same strand as the capture binding domain and folds to create a hairpin structure (see, e.g., FIGS. 5A and 5B). In some instances, the hairpin structure blocks access to the capture binding domain. With respect to nucleic acid analyte detection, also provided herein are methods for enhancing the specificity of binding of a probe oligonucleotide to a target analyte in a biological sample, where the probe oligonucleotide includes at least a sequence that specifically binds to a target analyte and a capture binding domain that is complementary to a capture probe, where the capture binding domain is blocked from hybridizing to a capture domain of the capture probe using either caged nucleotides or by a sequence complementary to the capture binding domain. By blocking the interaction of the capture binding domain with the capture domain of the capture probe on a substrate, the methods provided herein enable greater specificity in binding an antigen-binding moiety or a probe oligonucleotide to its target analyte and increase resolution of a spatial array by reducing background noise (e.g., non-specific binding). In addition, the disclosure provides methods for releasing the block, thereby providing temporal and spatial control over the interaction between an antigen-binding moiety and/or a probe oligonucleotide with a capture domain of a capture probe on a substrate at the time point when such binding occurs during a workflow.

This disclosure features methods wherein the specificity of binding of an oligonucleotide to a target analyte is increased by about 5%, by about 10%, by about 15%, by about 20%, by about 25%, by about 30%, by about 35%, by about 40%, by about 45%, by about 50%, by about 55%, by about 60%, by about 65%, by about 70%, by about 75%, by about 80%, by about 85%, by about 90%, by about 95%. In some embodiments, the methods increased specificity of binding of an oligonucleotide to a target analyte by about 1.5-fold, by about 2.0-fold, by about 2.5-fold, by about 3.0-fold, by about 3.5-fold, by about 4.0-fold, by about 4.5-fold, by about 5.0-fold, by about 6-fold, by about 7-fold, by about 8-fold, by about 9-fold, by about 10-fold, or more compared to a setting in which the capture binding domain is not blocked.

This disclosure features methods wherein the specificity of binding of a capture binding domain to a capture domain of a capture probe is increased by about 5%, by about 10%, by about 15%, by about 20%, by about 25%, by about 30%, by about 35%, by about 40%, by about 45%, by about 50%, by about 55%, by about 60%, by about 65%, by about 70%, by about 75%, by about 80%, by about 85%, by about 90%, by about 95%. In some embodiments, the methods increased specificity of binding of a capture binding domain to a capture domain of a capture probe by about 1.5-fold, by about 2.0-fold, by about 2.5-fold, by about 3.0-fold, by about 3.5-fold, by about 4.0-fold, by about 4.5-fold, by about 5.0-fold, by about 6-fold, by about 7-fold, by about 8-fold, by about 9-fold, by about 10-fold, or more compared to a setting in which the capture binding domain is not blocked.

(a) Blocking Probes and the Capture Binding Domain

In some instances, disclosed are blocking probes that hybridize to a capture binding domain. In some instances, the blocking probes are independent nucleotides from the capture binding domain. In some instances, the blocking probes and capture binding domain are on a contiguous nucleotide sequence and form a hairpin upon interaction.

Figure 4A:
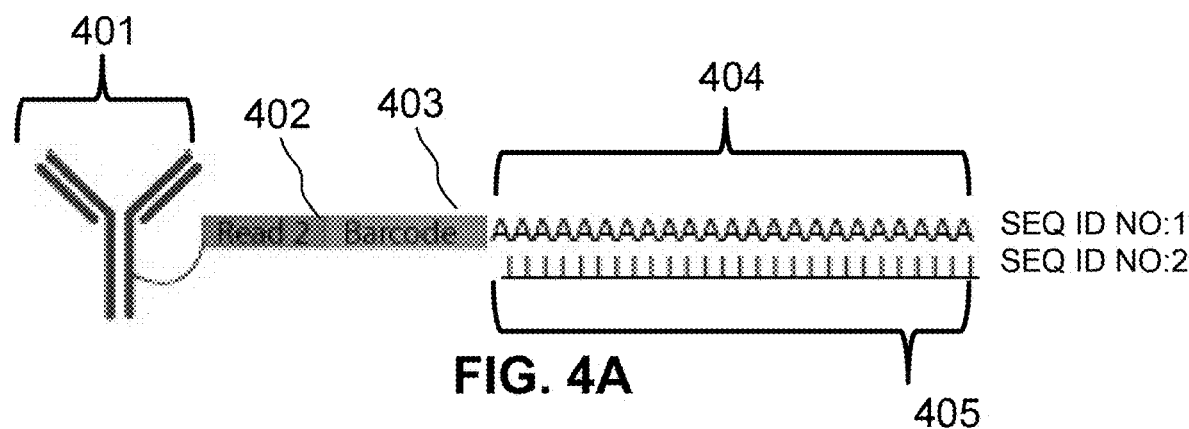
FIG. 4A is an exemplary schematic showing an analyte binding moiety comprising an oligonucleotide having a capture binding domain (indicated by a poly(A) sequence) that is hybridized to a blocking domain (indicated by a poly(T) sequence).

In some embodiments, the capture binding domain can include a sequence that is at least partially complementary to a sequence of a capture domain of a capture probe (e.g., any of the exemplary capture domains described herein). FIG. 4A shows an exemplary capture binding domain attached to an analyte-binding moiety used to detect a protein in a biological sample. As show in FIG. 4A, an analyte-binding moiety 401 includes an oligonucleotide that includes a primer (e.g., a read2) sequence 402, an analyte-binding-moiety barcode 403, a capture binding domain having a first sequence (i.e., a capture binding domain) 404 (e.g., an exemplary poly A), and a blocking probe or second sequence 405 (e.g., poly T or poly U), where the blocking sequence blocks the capture binding domain from hybridizing to a capture domain on a capture probe. In some instances, the blocking sequence 405 is called a blocking probe as disclosed herein. In some instances, the blocking probe is a poly T sequence as exemplified in FIG. 4A.

Figure 4B:
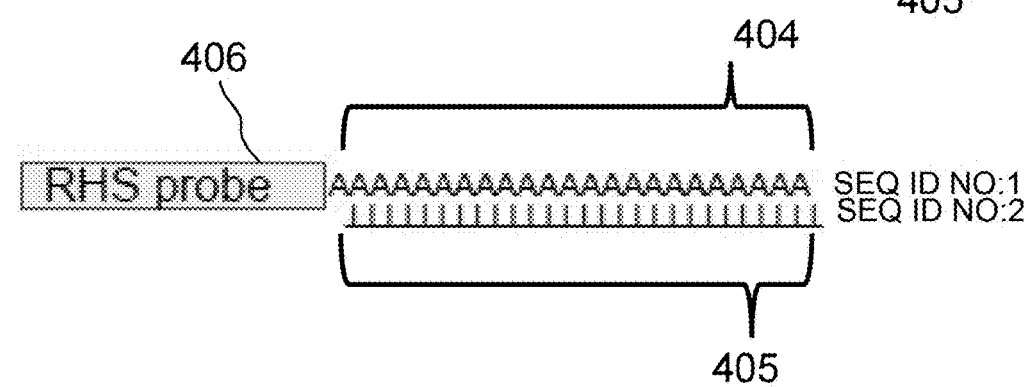
FIG. 4B is an exemplary schematic showing an oligonucleotide probe (RHS) from an RNA-templated ligation reaction. The probe includes a capture binding domain (indicated by a poly(A) sequence) hybridized to a blocking domain (indicated by a poly(T) sequence).

FIG. 4B shows an exemplary capture binding domain attached to a probe oligonucleotide (e.g., a right hand (e.g., an RHS) probe). As shown in FIG. 4B, the methods include a probe oligonucleotide 406 (e.g., a second probe oligonucleotide that can be used in a RNA templated ligation as described below) that includes a first sequence (i.e., a capture binding domain) 404 (e.g., exemplary poly A) and a blocking sequence 405 (e.g., a poly T or a poly U), where the blocking sequence blocks the capture binding domain from hybridizing to a capture domain on a capture probe. In some instances, the blocking sequence 405 is called a blocking probe or second sequence as disclosed herein. In some instances, the blocking probe is a poly T sequence.

In some instances, as shown in FIGS. 4A and 4B, the blocking probe sequence is not on a contiguous sequence with the capture binding domain. In other words, in some instances, the capture binding domain (also herein called a first sequence) and the blocking sequence are independent polynucleotides. In some instances, it will be apparent to one skilled in the art that the terms "capture binding domain" and "first sequence" are used interchangeably in this disclosure.

In a non-limiting example, the first sequence can be a poly(A) sequence when the capture domain sequence of the capture probe on the substrate is a poly(T) sequence. In some embodiments, the capture binding domain includes a capture binding domain substantially complementary to the capture domain of the capture probe. By substantially complementary, it is meant that the first sequence of the capture binding domain is at least 70%, at least 75%, at least 80%, at least 85%, at least 90%, at least 91%, at least 92%, at least 93%, at least 94%, at least 95%, at least 96%, at least 97%, at least 98%, at least 99%, or 100% complementary to a sequence in the capture domain of the capture probe. In another example, the first sequence of the capture binding domain can be a random sequence (e.g., random hexamer) that is at least partially complementary to a capture domain sequence of the capture probe that is also a random sequence. In yet another example, a capture binding domain can be a mixture of a homopolymeric sequence (e.g., a poly(T) sequence) and a random sequence (e.g., random hexamer) when a capture domain sequence of the capture probe is also a sequence that includes a homopolymeric sequence (e.g., a poly(A) sequence) and a random sequence. In some embodiments, the capture binding domain includes ribonucleotides, deoxyribonucleotides, and/or synthetic nucleotides that are capable of participating in Watson-Crick type or analogous base pair interactions. In some embodiments, the first sequence of the capture binding domain sequence includes at least 10 nucleotides, at least 11 nucleotides, at least 12 nucleotides, at least 13 nucleotides, at least 14 nucleotides, at least 15 nucleotides, at least 16 nucleotides, at least 17 nucleotides, at least 18 nucleotides, at least 19 nucleotides, at least 20 nucleotides, at least 21 nucleotides, at least 22 nucleotides, at least 23 nucleotides, or at least 24 nucleotides. In some embodiments, the first sequence of the capture binding domain includes at least 25 nucleotides, at least 30 nucleotides, or at least 35 nucleotides.

In some embodiments, the capture binding domain (i.e., the first sequence) and the blocking probe (i.e., the second sequence) of the capture binding domain are located on the same contiguous nucleic acid sequence. Where the capture binding domain and the blocking probe are located on the same contiguous nucleic acid sequence, the second sequence (e.g., a blocking probe) is located 3' of the first sequence. Where the first sequence and the second sequence (e.g., a blocking probe) of the capture binding domain are located on the same contiguous nucleic acid sequence, the second sequence (e.g., the blocking probe) is located 5' of the first sequence. As used herein, the terms second sequence and blocking probe are used interchangeably.

In some instances, the second sequence (e.g., the blocking probe) of the capture binding domain includes a nucleic acid sequence. In some instances, the second sequence is also called a blocking probe or blocking domain, and each term is used interchangeably. In some instances, the blocking domain is a DNA oligonucleotide. In some instances, the blocking domain is an RNA oligonucleotide. In some embodiments, a blocking probe of the capture binding domain includes a sequence that is complementary or substantially complementary to a first sequence of the capture binding domain. In some embodiments, the blocking probe prevents the first sequence of the capture binding domain from binding the capture domain of the capture probe when present. In some embodiments, the blocking probe is removed prior to binding the first sequence of the capture binding domain (e.g., present in a ligated probe) to a capture domain on a capture probe. In some embodiments, a blocking probe of the capture binding domain includes a poly-uridine sequence, a poly-thymidine sequence, or both. In some instances, the blocking probe (or the second sequence) is part of a hairpin structure that specifically binds to a capture binding domain and prevents the capture binding domain from hybridizing to a capture domain of a capture probe. See e.g., FIGS. 5A and 5B.

In some embodiments, the second sequence (e.g., the blocking probe) of the capture binding domain includes a sequence configured to hybridize to the first sequence of the capture binding domain. When the blocking probe is hybridized to the first sequence, the first sequence is blocked from hybridizing with a capture domain of a capture probe. In some embodiments, the blocking probe includes a sequence that is complementary to the first sequence. In some embodiments, the blocking probe includes a sequence that is substantially complementary to the first sequence. In some embodiments, the blocking probe includes a sequence that is at least 70%, at least 75%, at least 80%, at least 85%, at least 90%, at least 91%, at least 92%, at least 93%, at least 94%, at least 95%, at least 96%, at least 97%, at least 98%, at least 99%, or 100% complementary to the first sequence of the capture binding domain.

In some embodiments, the blocking probe of the capture binding domain includes a homopolymeric sequence that is substantially complementary to the first sequence of the capture binding domain. In some embodiments, the blocking probe is configured to hybridize to a poly(A), poly(T), or a poly-rU sequence. In some embodiments, the blocking probe includes a poly(A), poly(T), or a poly(U) sequence. In some embodiments, the first sequence includes a homopolymeric sequence. In some embodiments, the first sequence includes a poly(A), poly(U), or a poly(T) sequence.

Figure 5A:
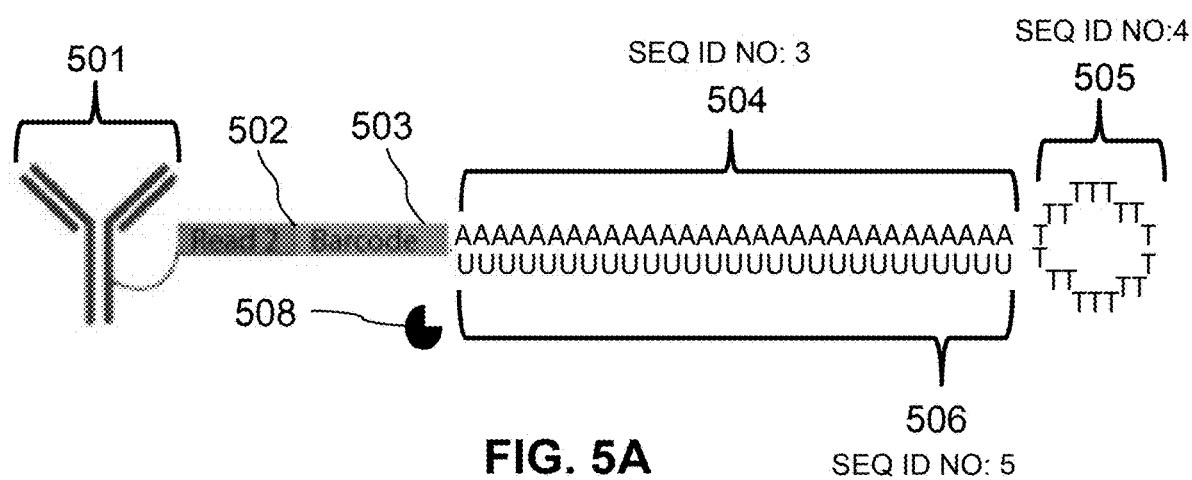
FIG. 5A is an exemplary schematic showing an analyte binding moiety that includes an oligonucleotide comprising a hairpin sequence disposed between a blocking domain (indicated by a poly(U) sequence) and a capture binding domain (indicated by a poly(A) sequence). As shown, the blocking domain hybridizes to the capture binding domain.
Figure 5B:
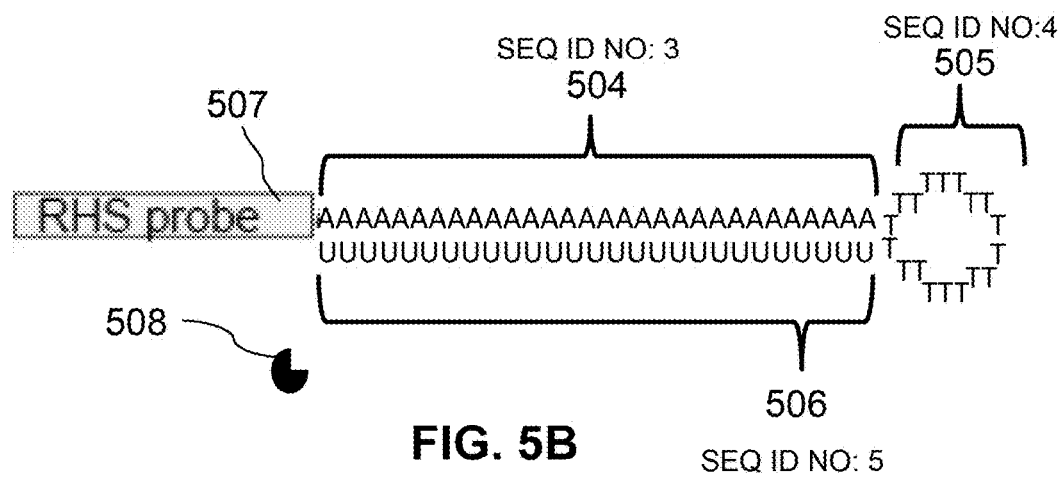
FIG. 5B is an exemplary schematic showing an oligonucleotide probe (RHS) from an RNA-templated ligation reaction. The probe includes an oligonucleotide comprising a hairpin sequence disposed between a blocking domain (indicated by a poly(U) sequence) and a capture binding domain (indicated by a poly(A) sequence). As shown, the blocking domain hybridizes to the capture binding domain.

In some embodiments, the capture binding domain further includes a hairpin sequence (as shown in FIGS. 5A and 5B). FIG. 5A shows an exemplary capture binding domain attached to an analyte-binding moiety used to detect a protein in a biological sample. As show in FIG. 5A, an analyte-binding moiety 501 includes an oligonucleotide that includes a primer (e.g., a read2) sequence 502, an analyte-binding-moiety barcode 503, a capture binding domain having a first sequence 504 (e.g., an exemplary poly A), a blocking probe 505 and a third sequence 506, wherein the second and/or third sequence can be poly T or poly U or a combination thereof, where the blocking probe creates a hairpin type structure and the third sequence blocks the first sequence from hybridizing to a capture domain on a capture probe. In some instances, the third sequence 506 is called a blocking. Further, 508 exemplifies a nuclease capable of digesting the blocking sequencing. In this example, 508 could be an endonuclease or mixture of nucleases capable of digesting uracils, such as UDG or a uracil specific excision mix such as USER (NEB).

FIG. 5B shows an exemplary capture binding domain attached to a probe oligonucleotide (e.g., a right hand (e.g., an RHS) probe). As shown in FIG. 5B, the methods include a probe oligonucleotide 507 (e.g., a second probe oligonucleotide that can be used in a RNA templated ligation as described below) that includes a first sequence 504 (e.g., exemplary poly A), a blocking probe 505 and a third sequence 506 wherein the second and/or third sequence can be poly T or a poly U or a combination thereof, where the blocking probe creates a hairpin type structure and the third sequence blocks the first sequence from hybridizing to a capture domain on a capture probe. In some instances, the third sequence 506 is called a blocking probe. In this example. In this example, 508 could be an endonuclease or mixture of nucleases capable of digesting uracils, such as UDG or a uracil specific excision mix such as USER (NEB).

Figure 6A:
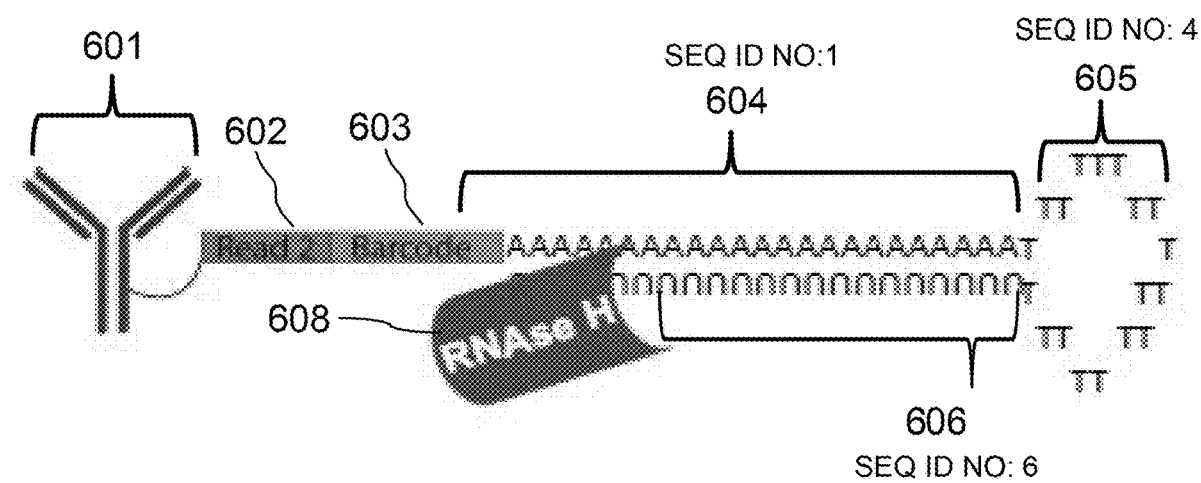
FIGS. 6A and 6B are exemplary schematics showing a blocking domain released by RNAse H.
Figure 6B:
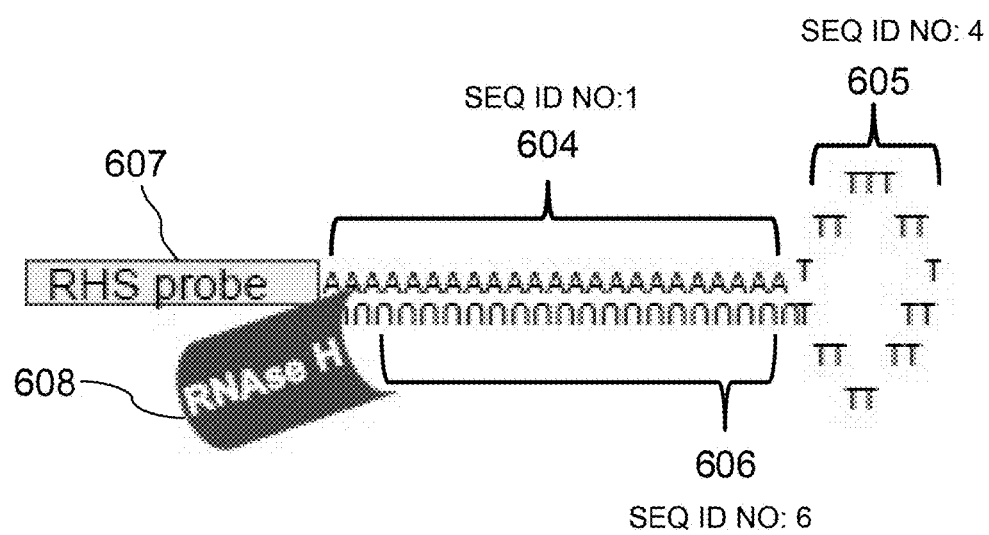

Another embodiment of a hairpin blocker scenario is exemplified in FIGS. 6A and 6B. As exemplified in FIG. 6A, an analyte-binding moiety 601 includes an oligonucleotide that includes a primer (e.g., a read2) sequence 602, an analyte-binding-moiety barcode 603, a capture binding domain having a first sequence (i.e., a capture binding domain) 604 (e.g., an exemplary poly A), a second hairpin sequence 605 and a third sequence 606, where the third sequence (i.e., a blocking probe) blocks the first sequence from hybridizing to a capture domain on a capture probe. In this example, 608 exemplifies an RNase H nuclease capable of digesting the uracil blocking sequencing from the DNA:RNA hybrid that is formed by blocking of the first sequence with a uracil containing third sequence.

As exemplified in FIG. 6B, the methods include a probe oligonucleotide 607 (e.g., a second probe oligonucleotide that can be used in a RNA templated ligation as described below) that includes a first sequence 604 (e.g., exemplary poly A), a second hairpin sequence 605 and a third sequence 606 where the third sequence blocks the first sequence from hybridizing to a capture domain on a capture probe. In this example, 608 exemplifies an RNase H nuclease capable of digesting the uracil blocking sequencing from the DNA:RNA hybrid that is formed by blocking of the first sequence with a uracil containing third sequence.

In some embodiments, the hairpin sequence is located 5' of the blocking probe in the capture binding domain. In some embodiments, the hairpin sequence is located 5' of the first sequence in the capture binding domain. In some embodiments, the capture binding domain includes from 5' to 3' a first sequence substantially complementary to the capture domain of a capture probe, a hairpin sequence, and a blocking probe substantially complementary to the first sequence. Alternatively, the capture binding domain includes from 3' to 5' a first sequence substantially complementary to the capture domain of a capture probe, a hairpin sequence, and a blocking probe substantially complementary to the first sequence.

In some embodiments, the hairpin sequence includes a sequence of about three nucleotides, about four nucleotides, about five nucleotides, about six nucleotides, about seven nucleotides, about eight nucleotides, about nine nucleotides or about 10 or more nucleotides. In some instances, the hairpin is at least about 15 nucleotides, at least about 20 nucleotides, at least about 25 nucleotides, at least about 30 nucleotides, or more nucleotides.

In some embodiments, the hairpin sequence includes DNA, RNA, DNA-RNA hybrid, or includes modified nucleotides. In some instances, the hairpin is a poly(U) sequence. In some instances, the RNA hairpin sequence is digested by USER and/or RNAse H using methods disclosed herein. In some instances, the poly(U) hairpin sequence is digested by USER and/or RNAse H using methods disclosed herein. In some instances, the hairpin is a poly(T) sequence. It is appreciated that the sequence of the hairpin (whether it includes DNA, RNA, DNA-RNA hybrid, or includes modified nucleotides) can be nearly any nucleotide sequence so long as it forms a hairpin, and in some instances, so long as it is digested by USER and/or RNAse H.

In some embodiments, methods provided herein require that the second sequence (e.g., the blocking probe) of the capture binding domain that is hybridized to the first sequence of the capture binding domain is released from the first sequence. In some embodiments, releasing the blocking probe (or second sequence) from the first sequence is performed under conditions where the blocking probe de-hybridizes from the first sequence.

In some embodiments, releasing the blocking probe from the first sequence includes cleaving the hairpin sequence. In some embodiments, the hairpin sequence includes a cleavable linker. For example, the cleavable linker can be a photocleavable linker, UV-cleavable linker, or an enzyme-cleavable linker. In some embodiments, the enzyme that cleaves that enzymatic-cleavable domain is an endonuclease. In some embodiments, the hairpin sequence includes a target sequence for a restriction endonuclease.

In some embodiments, releasing the blocking probe (or the second sequence) of the capture binding domain that is hybridized to the first sequence of the capture binding domain includes contacting the blocking probe with a restriction endonuclease. In some embodiments, releasing the blocking probe from the first sequence includes contacting the blocking probe with an endoribonuclease. In some embodiments, when the blocking probe is an RNA sequence (e.g., a sequence comprising uracils) the endoribonuclease is one or more of RNase H, RNase A, RNase C, or RNase I. In some embodiments, wherein the endoribonuclease is RNase H. In some embodiments, the RNase H includes RNase H1, RNase H2, or RNase H1 and RNase H2.

In some embodiments, the hairpin sequence includes a homopolymeric sequence. In some embodiments, the hairpin sequence includes a poly(T) or poly(U) sequence. For example, the hairpin sequence includes a poly(U) sequence. In some embodiments, provided herein are methods for releasing the blocking probe by contacting the hairpin sequence with a Uracil-Specific Excision Reagent (USER) enzyme.

In some embodiments, releasing the blocking probe from the first sequence includes denaturing the blocking probe under conditions where the blocking probe de-hybridizes from the first sequence. In some embodiments, denaturing comprises using chemical denaturation or physical denaturation. For example, wherein physical denaturation (e.g., temperature) is used to release the blocking probe. In some embodiments, denaturing includes temperature modulation. For example, a first sequence and a blocking probe have predetermined annealing temperatures based on the composition (A, G, C, or T) within the known sequences. In some embodiments, the temperature is modulate up to 5° C., up to 10° C., up to 15° C., up to 20° C., up to 25° C., up to 30° C., or up to 35° C. above the predetermined annealing temperature. In some embodiments, the temperature is modulated at 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35° C. above the predetermined annealing temperature. In some embodiments, once the temperature is modulated to a temperature above the predetermined annealing temperature, the temperature is cooled down to the predetermined annealing temperature at a ramp rate of about 0.1° C./second to about 1.0° C./second (e.g., about 0.1° C./second to about 0.9° C./second, about 0.1° C./second to about 0.8° C./second, about 0.1° C./second to about 0.7° C./second, about 0.1° C./second to about 0.6° C./second, about 0.1° C./second to about 0.5° C./second, about 0.1° C./second to about 0.4° C./second, about 0.1° C./second to about 0.3° C./second, about 0.1° C./second to about 0.2° C./second, about 0.2° C./second to about 1.0° C./second, about 0.2° C./second to about 0.9° C./second, about 0.2° C./second to about 0.8° C./second, about 0.2° C./second to about 0.7° C./second, about 0.2° C./second to about 0.6° C./second, about 0.2° C./second to about 0.5° C./second, about 0.2° C./second to about 0.4° C./second, about 0.2° C./second to about 0.3° C./second, about 0.3 to about 1.0° C./second, about 0.3° C./second to about 0.9° C./second, about 0.3° C./second to about 0.8° C./second, about 0.3° C./second to about 0.7° C./second, about 0.3° C./second to about 0.6° C./second, about 0.3° C./second to about 0.5° C./second, about 0.3° C./second to about 0.4° C./second, about 0.4° C./second to about 1.0° C./second, about 0.4° C./second to about 0.9° C./second, about 0.4° C./second to about 0.8° C./second, about 0.4° C./second to about 0.7° C./second, about 0.4° C./second to about 0.6° C./second, about 0.4° C./second to about 0.5° C./second, about 0.5°

C./second to about 1.0° C./second, about 0.5° C./second to about 0.9° C./second, about 0.5° C./second to about 0.8° C./second, about 0.5° C./second to about 0.7° C./second, about 0.5° C./second to about 0.6° C./second, about 0.6° C./second to about 1.0° C./second, about 0.6° C./second to about 0.9° C./second, about 0.6° C./second to about 0.8° C./second, about 0.6° C./second to about 0.7° C./second, about 0.7° C./second to about 1.0° C./second, about 0.7° C./second to about 0.9° C./second, about 0.7° C./second to about 0.8° C./second, about 0.8° C./second to about 1.0° C./second, about 0.8° C./second to about 0.9° C./second, or about 0.9° C./second to about 1.0° C./second). In some embodiments, denaturing includes temperature cycling. In some embodiments, denaturing includes alternating between denaturing conditions (e.g., a denaturing temperature) and non-denaturing conditions (e.g., annealing temperature).

It is appreciated that, notwithstanding any particular function in an embodiment, the hairpin sequence can be any sequence configuration, so long as a hairpin is formed. Thus, in some instances, it could be, for example, a degenerate sequence, a random sequence, or otherwise (comprising any sequence of polynucleotides).

In some embodiments, the hairpin sequence further includes a sequence that is capable of binding to a capture domain of a capture probe. For example, releasing the hairpin sequence from the capture binding domain can require that the hairpin sequence is cleaved, where the portion of the hairpin sequence that is left following cleavage includes a sequence that is capable of binding to a capture domain of a capture probe. In some embodiments, all or a portion of the hairpin sequence is substantially complementary to a capture domain of a capture probe. In some embodiments, the sequence that is substantially complementary to a capture domain of a capture probe is located on the free 5' or free 3' end following cleavage of the hairpin sequence. In some embodiments, the cleavage of the hairpin results in a single stranded sequence that is capable of binding to a capture domain of a capture probe on a spatial array. While the release of a hairpin sequence may enable hybridization to a capture domain of a capture probe, it is contemplated that release of the hairpin would not significantly affect the capture of the target analyte by an analyte-binding moiety or a probe oligonucleotide (e.g., a second probe oligonucleotide).

(b) Capture Binding Domains Having a Plurality of Caged Nucleotides

In some instances, the one or more blocking methods disclosed herein include a plurality of caged nucleotides. In some embodiments, provided herein are methods where a capture binding domain includes a plurality of caged nucleotides. The caged nucleotides prevent the capture binding domain from interacting with the capture domain of the capture probe. The caged nucleotides include caged moieties that block Watson-Crick hydrogen bonding, thereby preventing interaction until activation, for example, through photolysis of the caged moiety that releases the caged moiety and restores the caged nucleotides ability to engage in Watson-Crick base pairing with a complement nucleotide.

Figure 7A:
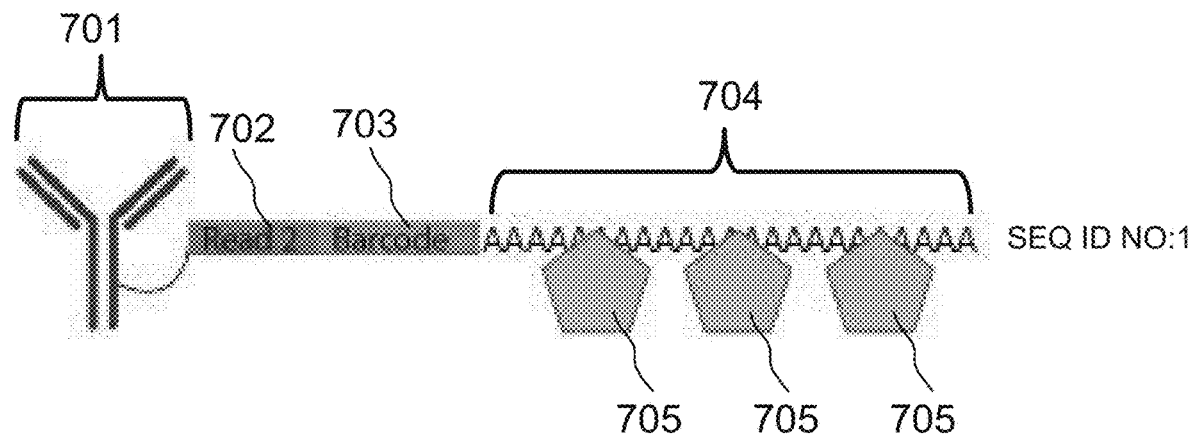
FIG. 7A is an exemplary schematic showing an analyte binding moiety that includes an oligonucleotide comprising a capture binding domain that is blocked using caged nucleotides (indicated by pentagons).
Figure 7B:
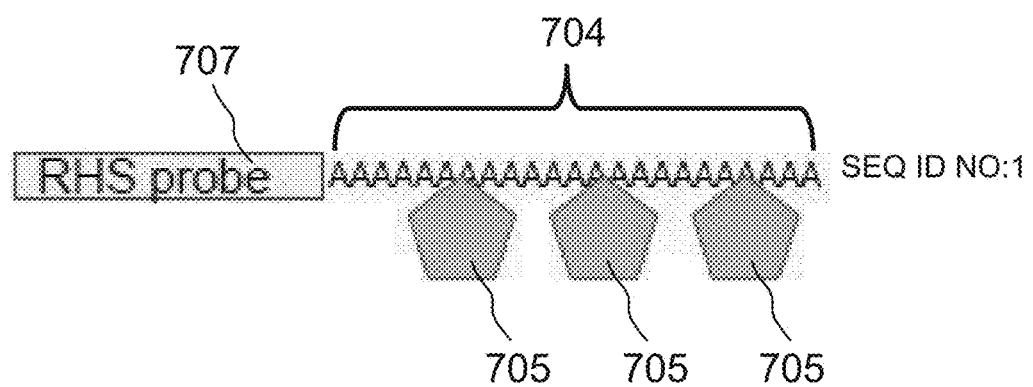
FIG. 7B is an exemplary schematic showing an oligonucleotide probe (RHS) from an RNA-templated ligation reaction. The probe comprises a capture binding domain that is blocked using caged nucleotides.

FIGS. 7A-7B are demonstrative of blocking a capture binding domain with caged nucleotides. As exemplified in FIG. 7A, an analyte-binding moiety 701 includes an oligonucleotide that includes a primer (e.g., a read2) sequence 702, an analyte-binding-moiety barcode 703 and a capture binding domain having a sequence 704 (e.g., an exemplary polyA). Caged nucleotides 705 block the sequence 704, thereby blocking the interaction between the capture binding domain and the capture domain of the capture probe. The same mechanism is depicted in FIG. 7B, except for a probe oligonucleotide 707 (e.g., a second probe oligonucleotide that can be used in a RNA templated ligation as described below) that includes a first sequence 704 (e.g., exemplary poly A) blocked with caged nucleotides 705, thereby blocking the interaction between the capture binding domain and the capture domain of the capture probe.

Figure 7C:
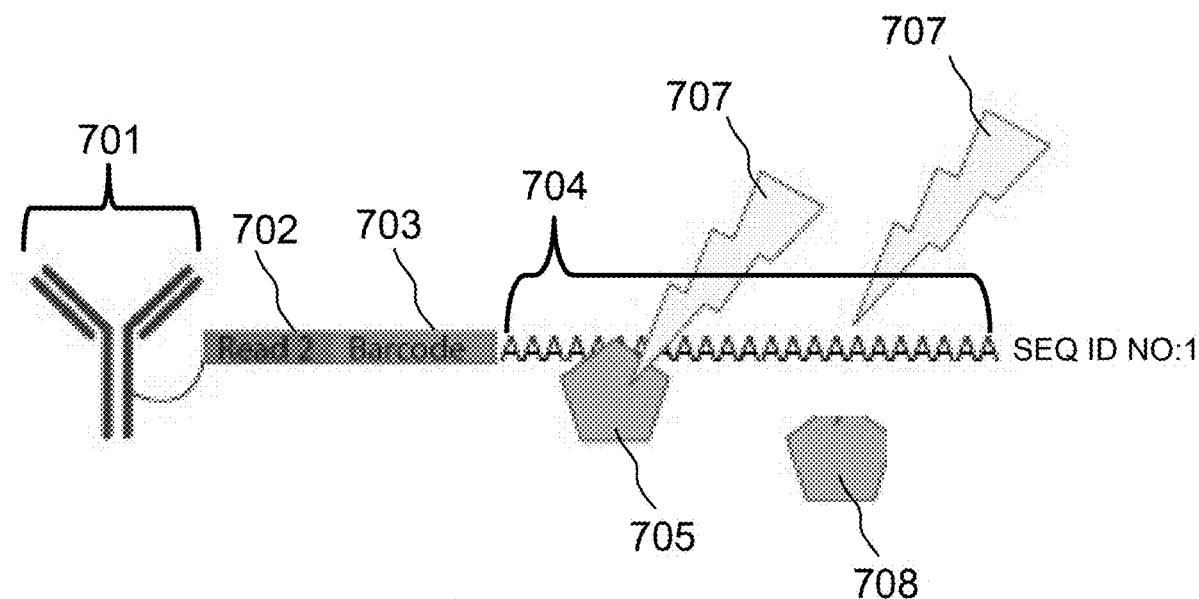
FIG. 7C is an exemplary schematic of an analyte binding moiety that includes a capture binding domain wherein the caged nucleotide are undergoing photolysis activation using light pulses.
Figure 7D:
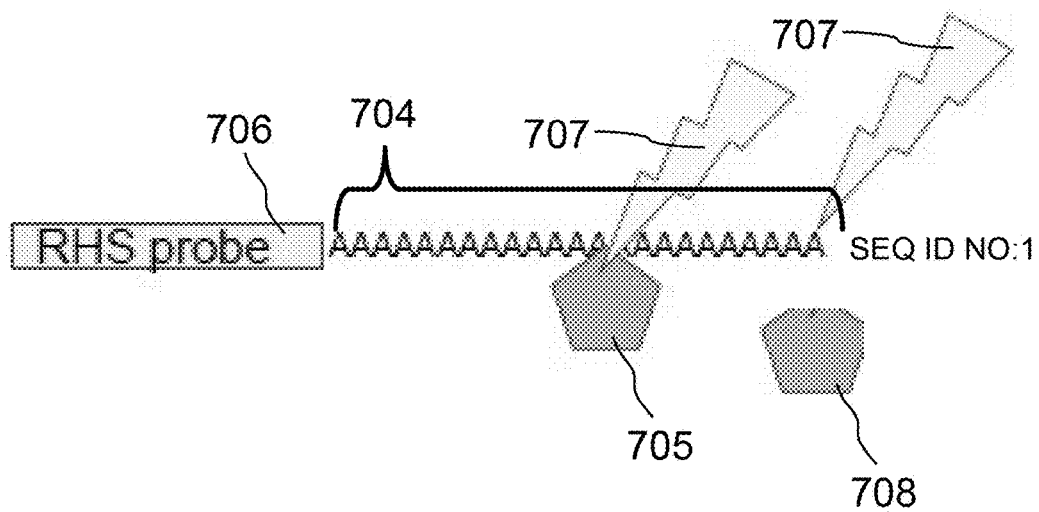
FIG. 7D is an exemplary schematic showing an RHS probe that includes a capture binding domain wherein the caged nucleotides are undergoing photolysis activation using light pulses.

FIGS. 7C-7D demonstrate the release of the caged nucleotides 705 via, in this example, the application of light for photolysis and release of the caged nucleotides 705 from the capture binding domain 704, thereby allowing the capture binding domain to hybridize to the capture domain of the capture probe.

In some embodiments, the capture binding domain includes a plurality of caged nucleotides, wherein a caged nucleotide of the plurality of caged nucleotides includes a caged moiety that is capable of preventing interaction between the capture binding domain and the capture domain of the capture probe. Non-limiting examples of caged nucleotides, also known as light-sensitive oligonucleotides, are described in Liu et al., *Acc. Chem. Res.*, 47(1): 45-55 (2014), which is incorporated by reference in its entirety. In some embodiments, the caged nucleotides include a caged moiety selected from the group of 6-nitropiperonyloxymethy (NPOM), 1-(ortho-nitrophenyl)-ethyl (NPE), 2-(ortho-nitrophenyl)propyl (NPP), diethylaminocoumarin (DEACM), and nitrodibenzofuran (NDBF).

In some embodiments, a caged nucleotide includes a non-naturally-occurring nucleotide selected from the group consisting of 6-nitropiperonyloxymethy (NPOM)-caged adenosine, 6-nitropiperonyloxymethy (NPOM)-caged guanosine, 6-nitropiperonyloxymethy (NPOM)-caged uridine, and 6-nitropiperonyloxymethy (NPOM)-caged thymidine. For example, the capture binding domain includes one or more caged nucleotides where the cage nucleotides include one or more 6-nitropiperonyloxymethy (NPOM)-caged guanosine. In another example, the capture binding domain includes one or more caged nucleotides where the cage nucleotides include one or more nitropiperonyloxymethy (NPOM)-caged uridine. In yet another example, the capture binding domain includes one or more caged nucleotides where the caged nucleotide includes one or more 6-nitropiperonyloxymethy (NPOM)-caged thymidine.

In some embodiments, the capture binding domain includes a combination of at least two or more of any of the caged nucleotides described herein. For example, the capture binding domain can include one or more 6-nitropiperonyloxymethy (NPOM)-caged guanosine and one or more nitropiperonyloxymethy (NPOM)-caged uridine. It is appreciated that a capture binding domain can include any combination of any of the caged nucleotides described herein.

In some embodiments, the capture binding domain includes one caged nucleotide, two caged nucleotides, three caged nucleotides, four caged nucleotides, five caged nucleotides, six caged nucleotides, seven caged nucleotides, eight caged nucleotides, nine caged nucleotides, or ten or more caged nucleotides.

In some embodiments, the capture binding domain includes a caged nucleotide at the 3' end. In some embodiments, the capture binding domain includes two caged nucleotides at the 3' end. In some embodiments, the capture binding domain includes at least three caged nucleotides at the 3' end.

In some embodiments, the capture binding domain includes a caged nucleotide at the 5' end. In some embodiments, the capture binding domain includes two caged nucleotides at the 5' end. In some embodiments, the capture binding domain includes at least three caged nucleotides at the 5' end.

In some embodiments, the capture binding domain includes a caged nucleotide at every odd position starting at the 3' end of the capture binding domain. In some embodiments, the capture binding domain includes a caged nucleotide at every odd position starting at the 5' end of the capture binding domain. In some embodiments, the capture binding domain includes a caged nucleotide at every even position starting at the 3' end of the capture binding domain. In some embodiments, the capture binding domain includes a caged nucleotide at every even position starting at the 5' end of the capture binding domain.

In some embodiments, the capture binding domain includes a sequence including at least 10%, at least, 20%, or at least 30% caged nucleotides. In some instances, the percentage of caged nucleotides in the capture binding domain is about 40%, about 50%, about 60%, about 70%, about 80% or higher. In some embodiments, the capture binding domain includes a sequence where every nucleotide is a caged nucleotide. It is understood that the limit of caged nucleotides is based on the sequence of the capture binding domain and on steric limitations of creating caged nucleotides in proximity to one another. Thus, in some instances, particular nucleotides (e.g., guanines) are replaced with caged nucleotides. In some instances, all guanines in a capture binding domain are replaced with caged nucleotides. In some instances, a fraction (e.g., about 10%, about 20%, about 30%, about 40%, about 50%, about 60%, about 70%, about 80%, about 90%, or about 95%) of guanines in a capture binding domain are replaced with caged nucleotides. In some instances, particular nucleotides (e.g., uridines or thymines) are replaced with caged nucleotides. In some instances, all uridines or thymines in a capture binding domain are replaced with caged nucleotides. In some instances, a fraction (e.g., about 10%, about 20%, about 30%, about 40%, about 50%, about 60%, about 70%, about 80%, about 90%, or about 95%) of uridines or thymines in a capture binding domain are replaced with caged nucleotides. Caged nucleotides are disclosed in Govan et al., *Nucleic Acids Research* (2013) 41; 22, 10518-10528, which is incorporated by reference in its entirety.

In some embodiments, the capture binding domain includes caged nucleotides that are evenly distributed throughout the capture binding domain. For example, a capture binding domain can include a sequence that includes at least 10% caged nucleotides where the caged nucleotides are evenly distributed throughout the capture binding domain. In some embodiments, the capture binding domain includes a sequence that is at least 10% caged nucleotides and where the 10% caged nucleotides are positioned at the 3' of the capture binding domain. In some embodiments, the capture binding domain includes a sequence that is at least 10% caged nucleotides and where the 10% caged nucleotides are positioned at the 5' end of the capture binding domain. In some embodiments, the caged nucleotides are included at every third, at every fourth, at every fifth, at every sixth nucleotide, or a combination thereof, of the capture binding domain sequence.

In some embodiments, provided herein are methods for releasing the caged moiety from the caged nucleotide. In some embodiments, releasing the caged moiety from the caged nucleotide includes activating the caged moiety. In some embodiments, releasing the caged moiety from the caged nucleotide restores the caged nucleotides ability to hybridize to a complementary nucleotide through Watson-Crick hydrogen bonding. For example, restoring the caged nucleotides ability to hybridize with a complementary nucleotide enables/restores the capture binding domain's ability to interact with the capture domain. Upon releasing the caged moiety from the caged nucleotide, the caged nucleotide is no longer "caged" in that the caged moiety is no longer linked (e.g., either covalently or non-covalently) to the caged nucleotide. As used herein, the term "caged nucleotide" can refer to a nucleotide that is linked to a caged moiety or a nucleotide that was linked to a caged moiety but is no longer linked as a result of activation of the caged moiety.

In some embodiments, provided herein are methods for activating the caged moiety thereby releasing the caged moiety from the caged nucleotide. In some embodiments, activating the caged moiety includes photolysis of the caged moiety from the nucleotide. As used herein, "photolysis" can refer to the process of removing or separating a caged moiety from a caged nucleotide using light. In some embodiments, activating (e.g., photolysis) the caged moiety includes exposing the caged moiety to light pulses (e.g., two or more, three or more, four or more, or five or more pulses of light) that in total are sufficient to release the caged moiety from the caged nucleotide. In some embodiments, activating the caged moiety includes exposing the caged moiety to a light pulse (e.g., a single light pulse) that is sufficient to release the caged moiety from the caged nucleotide. In some embodiments, activating the caged moiety includes exposing the caged moiety to a plurality of pulses (e.g., one, or two or more pulses of light) where the light is at a wavelength of about less than about 360 nm. In some embodiments, the source of the light that is at a wavelength of about less than 360 nm is a UV light. The UV light can originate from a fluorescence microscope, a UV laser or a UV flashlamp, or any source of UV light known in the art.

In some embodiments, once the caged moiety is released from the capture binding domain, the oligonucleotide, probe oligonucleotide, or ligation product that includes the capture binding domain, is able to hybridize to the capture domain of the capture probe. Finally, to identify the location of the analyte or determine the interaction between two or more analyte-binding moieties, all or part of the sequence of the oligonucleotide, probe oligonucleotide, or ligation product, or a complement thereof, can be determined.

(c) Methods of Enhancing Detection of Protein Analytes (i) Analyte-Binding Moieties In some embodiments, provided herein are methods for enhancing the specificity of binding of an antigen-binding moiety to a target analyte in a biological sample where the method includes blocking the antigen-binding moiety from prematurely hybridizing with a capture probe affixed to a substrate. The antigen-binding moiety includes an oligonucleotide having at least an analyte-binding-moiety barcode and a capture binding domain where the capture binding domain can hybridize to a capture domain of a capture probe. In the method provided herein, the capture binding domain of the oligonucleotide is blocked and prevented from hybridizing to the capture domain of the capture probe on the substrate. Releasing the block from the capture binding domain enables the capture binding domain to specifically bind the capture domain of the capture probe on the substrate at the appropriate time in the workflow.

FIG. 1 exemplifies an analyte binding moiety. Briefly, an analyte binding moiety 102 including an analyte binding domain 104 which can bind to a target analyte 106. The analyte binding moiety further includes an oligonucleotide 108 with comprises an analyte binding moiety barcode and a capture binding domain which can hybridize to a capture domain of a capture probe.

Figure 2:
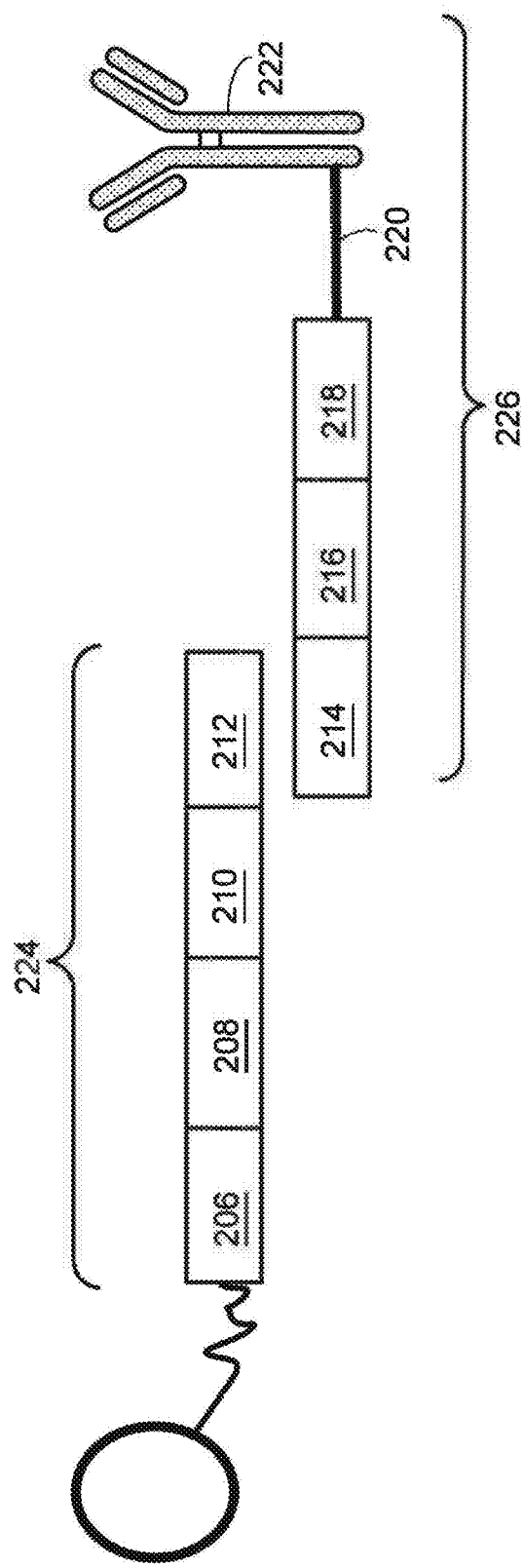
FIG. 2 is a schematic diagram depicting an exemplary interaction between a feature-immobilized capture probe 224 and an analyte capture agent 226.

FIG. 2 is a schematic diagram depicting an exemplary interaction between a feature-immobilized capture probe 224 and an analyte capture agent 226. The feature-immobilized capture probe 224 can include a spatial barcode 208 as well as one or more functional sequences 206 and 210, as described elsewhere herein. The capture probe can also include a capture domain 212 that is capable of binding to an analyte capture agent 226. The analyte capture agent 226 can include a functional sequence 218, capture agent barcode domain 216, and an analyte capture sequence 214 that is capable of binding to the capture domain 212 of the capture probe 224. The analyte capture agent can also include a linker 220 that allows the capture agent barcode domain 216 to couple to the analyte binding moiety 222.

Figure 3A:
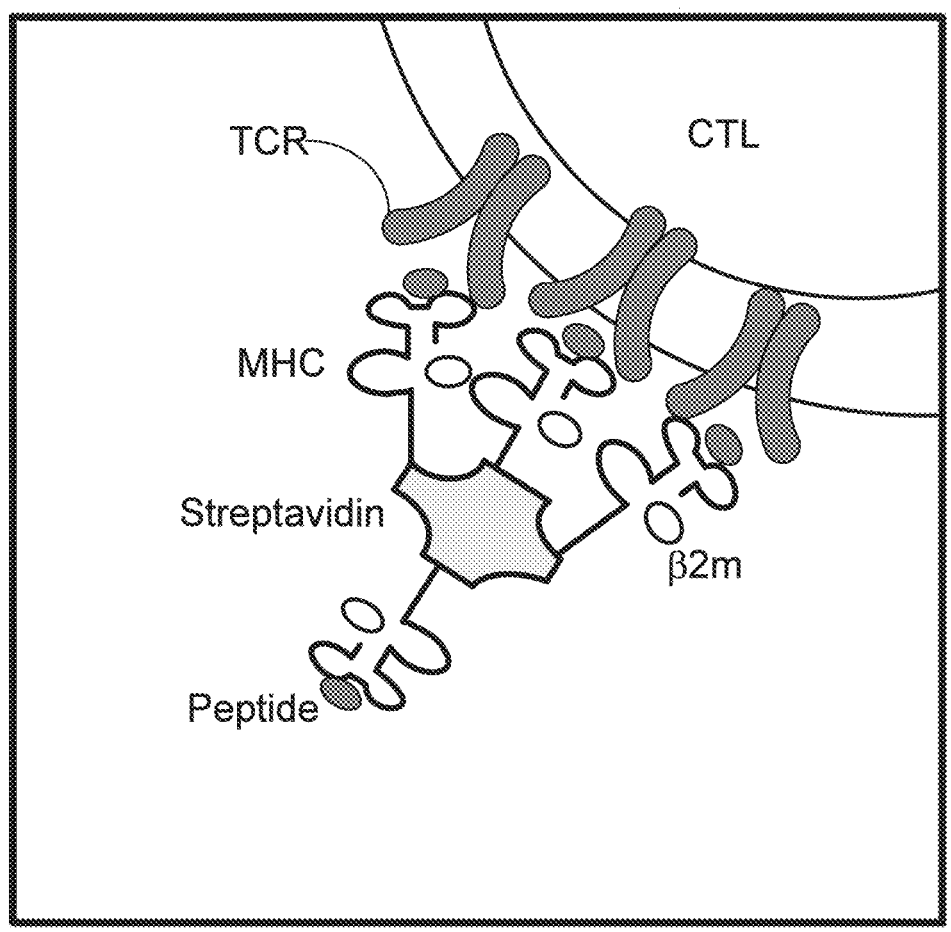
FIGS. 3A, 3B, and 3C are schematics illustrating how streptavidin cell tags can be utilized in an array-based system to produce a spatially-barcoded cells or cellular contents.
Figure 3B:
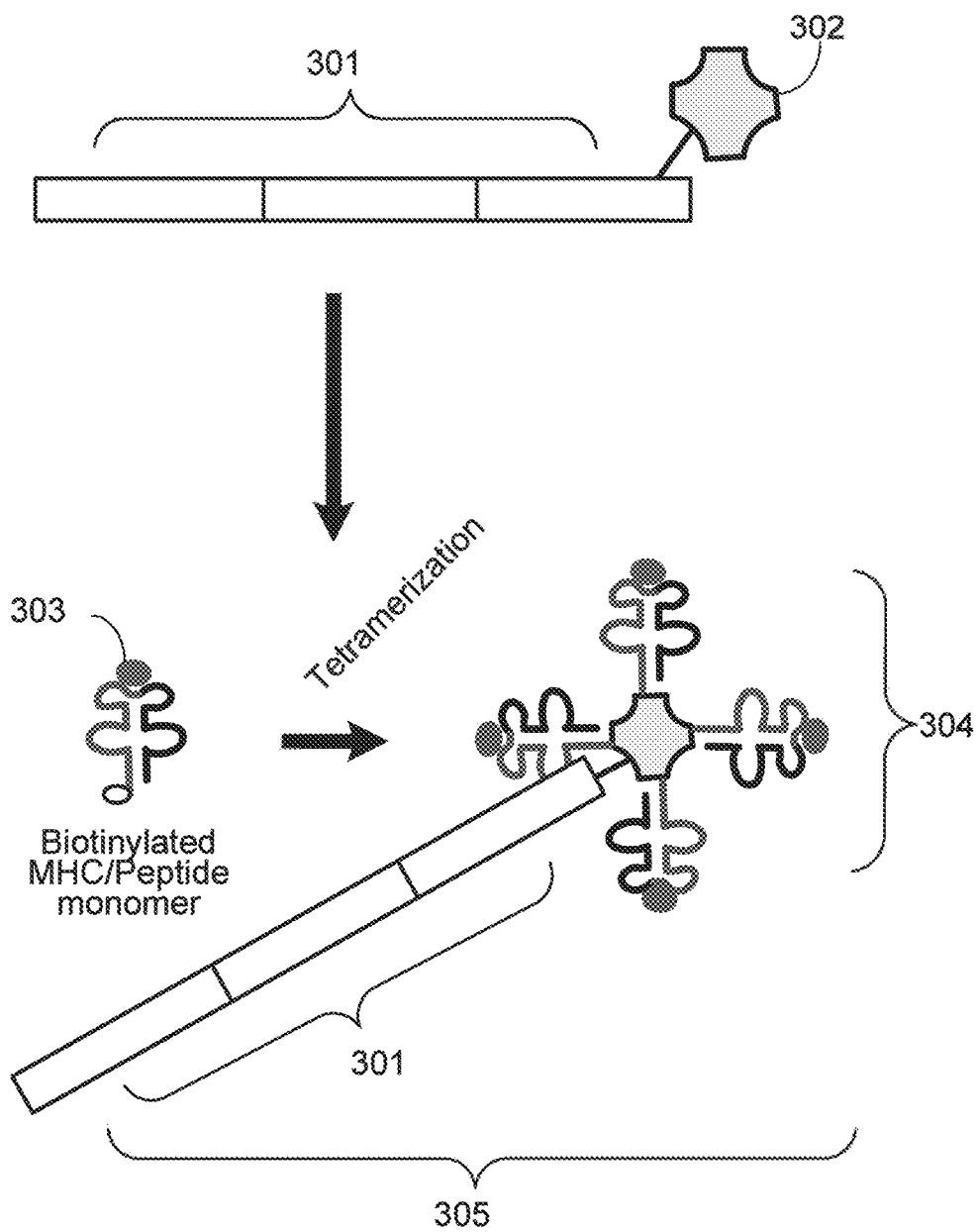
Figure 3C:
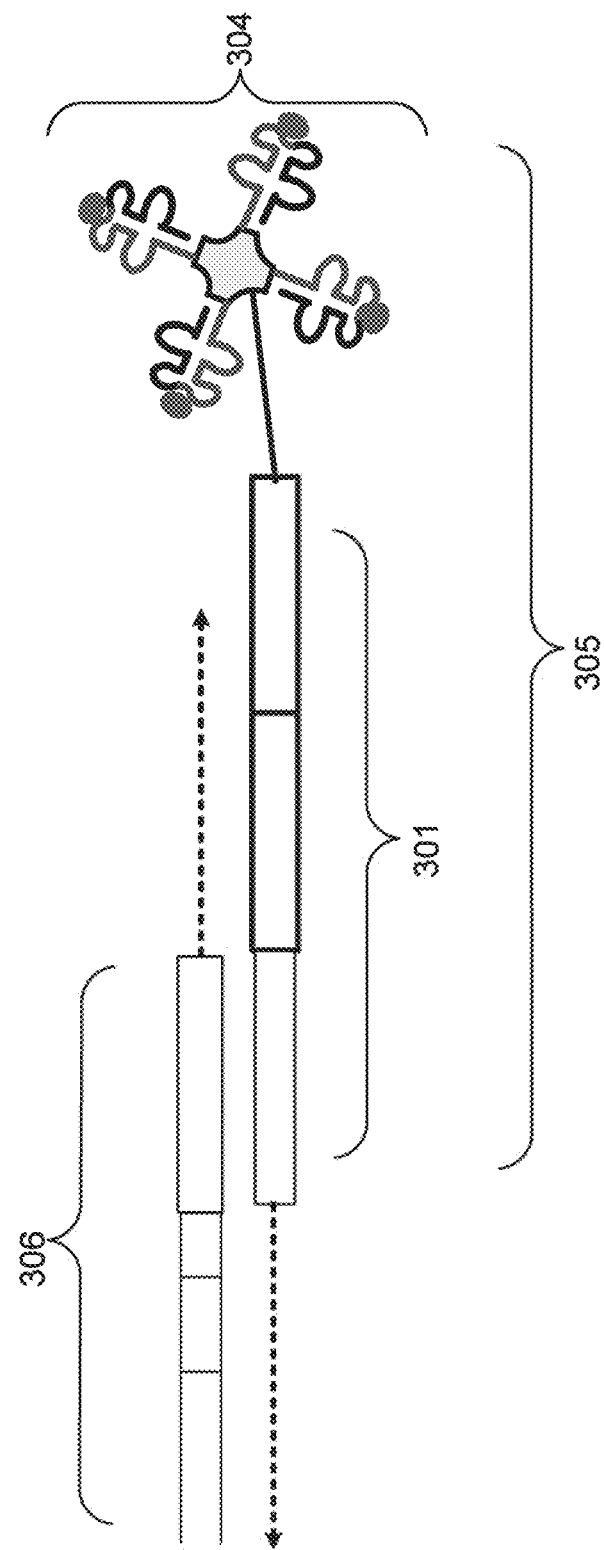

FIGS. 3A, 3B, and 3C are schematics illustrating how streptavidin cell tags can be utilized in an array-based system to produce a spatially-barcoded cell or cellular contents. For example, as shown in FIG. 3A, peptide-bound major histocompatibility complex (MHC) can be individually associated with biotin (β2m) and bound to a streptavidin moiety such that the streptavidin moiety comprises multiple pMHC moieties. Each of these moieties can bind to a TCR such that the streptavidin binds to a target T-cell via multiple MCH/TCR binding interactions. Multiple interactions synergize and can substantially improve binding affinity. Such improved affinity can improve labelling of T-cells and also reduce the likelihood that labels will dissociate from T-cell surfaces. As shown in FIG. 3B, a capture agent barcode domain 301 can be modified with streptavidin 302 and contacted with multiple molecules of biotinylated MHC 303 such that the biotinylated MHC 303 molecules are coupled with the streptavidin conjugated capture agent barcode domain 301. The result is a barcoded MHC multimer complex 305. As shown in FIG. 3B, the capture agent barcode domain sequence 301 can identify the MHC as its associated label and also includes optional functional sequences such as sequences for hybridization with other oligonucleotides. As shown in FIG. 3C, one example oligonucleotide is capture probe 306 that comprises a complementary sequence (e.g., rGrGrG corresponding to C C C), a barcode sequence and other functional sequences, such as, for example, a UMI, an adapter sequence (e.g., comprising a sequencing primer sequence (e.g., R1 or a partial R1 ("pR1"), R2), a flow cell attachment sequence (e.g., P5 or P7 or partial sequences thereof)), etc. In some cases, capture probe 306 may at first be associated with a feature (e.g., a gel bead) and released from the feature. In other embodiments, capture probe 306 can hybridize with a capture agent barcode domain 301 of the MHC-oligonucleotide complex 305. The hybridized oligonucleotides (Spacer C C C and Spacer rGrGrG) can then be extended in primer extension reactions such that constructs comprising sequences that correspond to each of the two spatial barcode sequences (the spatial barcode associated with the capture probe, and the barcode associated with the MHC-oligonucleotide complex) are generated. In some cases, one or both of these corresponding sequences may be a complement of the original sequence in capture probe 306 or capture agent barcode domain 301. In other embodiments, the capture probe and the capture agent barcode domain are ligated together. The resulting constructs can be optionally further processed (e.g., to add any additional sequences and/or for clean-up) and subjected to sequencing. As described elsewhere herein, a sequence derived from the capture probe 306 spatial barcode sequence may be used to identify a feature and the sequence derived from spatial barcode sequence on the capture agent barcode domain 301 may be used to identify the particular peptide MHC complex 304 bound on the surface of the cell (e.g., when using MHC-peptide libraries for screening immune cells or immune cell populations).

In one feature of the disclosure, the method for enhancing the specificity of binding of an analyte-binding moiety to a target analyte includes (a) contacting the biological sample with a substrate, wherein the substrate includes a plurality of capture probes affixed to the substrate, wherein the capture probe includes a spatial barcode and the capture domain; (b) binding an analyte-binding moiety to a target analyte in the biological sample, wherein the analyte-binding moiety is associated with an oligonucleotide including a capture binding domain that hybridizes to a capture domain of a capture probe, wherein the capture binding domain is blocked and prevented from hybridizing to the capture domain of the capture probe affixed to the substrate; (c) releasing the block from the capture binding domain, thereby allowing the capture binding domain to bind to the capture domain of the capture probe on the substrate, thereby enhancing the specificity of binding of an analyte-binding moiety to a target analyte in a biological sample.

In another feature of the disclosure, the method for enhancing the specificity of binding of an analyte-binding moiety to a target analyte includes (a) contacting the biological sample with a substrate, wherein the substrate includes a plurality of capture probes affixed to the substrate, wherein the capture probe includes a spatial barcode and the capture domain; (b) binding an analyte-binding moiety to a target analyte in the biological sample, wherein the analyte-binding moiety is associated with an oligonucleotide including a capture binding domain that hybridizes to a capture domain of a capture probe, wherein the capture binding domain includes caged nucleotides, where a caged nucleotide of the plurality of caged nucleotides includes a caged moiety that blocks the capture binding domain from hybridizing to the capture domain of the capture probe affixed to the substrate; (c) releasing (e.g., through activation or photolysis) the caged moiety from the caged nucleotides of the plurality of caged nucleotides from the capture binding domain, and allowing the capture binding domain to bind to the capture domain of the capture probe on the substrate, thereby enhancing the specificity of binding of an analyte-binding moiety to a target analyte in a biological sample.

In another feature of the disclosure, the method for enhancing the specificity of binding of an analyte-binding moiety to a target analyte includes (a) contacting the biological sample with a substrate, wherein the substrate includes a plurality of capture probes affixed to the substrate, wherein the capture probes include a spatial barcode and the capture domain; (b) binding an analyte-binding moiety to a target analyte in the biological sample, wherein the analyte-binding moiety is associated with an oligonucleotide including a capture binding domain that hybridizes to a capture domain of a capture probe, wherein the capture binding domain includes a first sequence that hybridizes to the capture domain of the capture probe and a second sequence (e.g., a blocking probe) that hybridizes to the first sequence, wherein the second sequence (e.g., the blocking probe) blocks the first sequence from hybridizing to the capture domain of the capture probe affixed to the substrate; (c) releasing the second sequence (e.g., the blocking probe) from the first sequence of the capture binding domain and allowing the first sequence of the capture binding domain to bind to the capture domain of the capture probe on the substrate, thereby enhancing the specificity of binding of an analyte-binding moiety to a target analyte in a biological sample.

Also provided herein are methods for determining (i) all or a part of the sequence of the oligonucleotide specifically bound to the capture domain, or a complement thereof, and (ii) all or a part of the sequence of the spatial barcode, or a complement thereof, and using the determined sequence of (i) and (ii) to identify a location of the target analyte in the biological sample.

In some embodiments, the oligonucleotide associated with the analyte-binding moiety includes a capture binding domain that hybridizes to a capture domain of a capture probe, where the capture binding domain includes a plurality of caged nucleotides, and where a caged nucleotide (e.g., any of the exemplary caged nucleotides described herein) of the plurality of caged nucleotides prevents hybridization between the capture binding domain and the capture domain of the capture probe.

In some embodiments, the oligonucleotide associated with the analyte-binding moiety includes an analyte-binding-moiety barcode (e.g., any of the exemplary an analyte-binding-moiety barcodes described herein). For example, the oligonucleotide associated with the analyte-binding moiety includes an analyte-binding-moiety barcode that identifies the particular analyte-binding moiety. In some embodiments where the method includes two or more analyte binding moieties that each bind to a different analyte, each analyte binding moiety is associated with an oligonucleotide that includes an analyte-binding-moiety barcode that enables differentiation between the two analyte-binding moieties. In some embodiments, the method identifying the location of the analyte in the biological sample includes determining all or part of the sequence of the oligonucleotide that is bound to the capture domain of the capture probe and includes an analyte-binding-moiety barcode.

In some embodiments, the oligonucleotide is a sequence of about 10 nucleotides to about 100 nucleotides (e.g., a sequence of about 10 nucleotides to about 90 nucleotides, about 10 nucleotides to about 80 nucleotides, about 10 nucleotides to about 70 nucleotides, about 10 nucleotides to about 60 nucleotides, about 10 nucleotides to about 50 nucleotides, about 10 nucleotides to about 40 nucleotides, about 10 nucleotides to about 30 nucleotides, about 10 nucleotides to about 20 nucleotides, about 20 nucleotides to about 90 nucleotides, about 20 nucleotides to about 80 nucleotides, about 20 nucleotides to about 70 nucleotides, about 20 nucleotides to about 60 nucleotides, about 20 nucleotides to about 50 nucleotides, about 20 nucleotides to about 40 nucleotides, about 20 nucleotides to about 30 nucleotides, about 30 nucleotides to about 90 nucleotides, about 30 nucleotides to about 80 nucleotides, about 30 nucleotides to about 70 nucleotides, about 30 nucleotides to about 60 nucleotides, about 30 nucleotides to about 50 nucleotides, about 30 nucleotides to about 40 nucleotides, about 40 nucleotides to about 90 nucleotides, about 40 nucleotides to about 80 nucleotides, about 40 nucleotides to about 70 nucleotides, about 40 nucleotides to about 60 nucleotides, about 40 nucleotides to about 50 nucleotides, about 50 nucleotides to about 90 nucleotides, about 50 nucleotides to about 80 nucleotides, about 50 nucleotides to about 60 nucleotides, about 70 nucleotides, about 50 nucleotides to about 60 nucleotides, about 60 nucleotides to about 90 nucleotides, about 60 nucleotides to about 80 nucleotides, about 60 nucleotides to about 70 nucleotides, about 70 nucleotides to about 90 nucleotides, about 70 nucleotides to about 80 nucleotides, or about 80 nucleotides to about 90 nucleotides).

In some embodiments, the analyte-binding moiety is a protein. In some embodiments, the protein is an antibody. For example, the antibody can be a monoclonal antibody, recombinant antibody, synthetic antibody, a single domain antibody, a single-chain variable fragment (scFv), and or an antigen-binding fragment (Fab).

In some embodiments, the analyte-binding moiety is associated with the oligonucleotide via a linker. In some embodiments, the linker is a cleavable linker. For example, the cleavable linker can be a photocleavable linker, UV-cleavable linker, or an enzyme-cleavable linker. In some embodiments, the cleavable linker is an enzyme cleavable linker. In some embodiments, the method also includes releasing the oligonucleotide from the analyte-binding moiety where the analyte-binding moiety is exposed to an enzyme that cleaves that cleavable linker thereby releasing the oligonucleotide. In some embodiments, releasing the oligonucleotide occurs prior to, contemporaneously with, or after releasing the block on the capture binding domain. In some embodiments, the oligonucleotide when associated with an analyte-binding moiety includes a free 3' end. In some embodiments, the oligonucleotide when associated with an analyte-binding moiety includes a free 5' end. In some embodiments, the analyte-binding moiety is as described herein.

In some embodiments, the analyte-binding moiety is a non-protein. For example, the analyte-binding moiety is an aptamer. In some embodiments, the analyte-binding moiety is a DNA aptamer. In some embodiments, the DNA aptamer is a single-stranded DNA molecule. In some embodiments, the analyte-binding moiety is an RNA aptamer. In some embodiments, the aptamer is synthetic. In some embodiments, the RNA aptamer is a single-stranded RNA molecule. In some embodiments, the aptamer binds to a specific target, including but not limited to, proteins, peptides, carbohydrates, small molecules, and toxins. In some embodiments, an aptamer as disclosed herein binds into its target specifically by folding into tertiary structures.

(ii) Proximity Ligation Including a Blocking Domain

In some embodiments, provided herein are methods for enhancing the specificity of binding of a first analyte-binding moiety to a first target analyte and a second analyte binding moiety to a second target analyte in a biological sample where the method includes binding a first analyte binding moiety including a first oligonucleotide to a first target analyte and a second analyte binding moiety including a second oligonucleotide to a second target analyte and generating a ligation product based on proximity ligation of the first oligonucleotide to the second nucleotide. One of the oligonucleotides that is included in the ligation product includes a capture binding domain that is blocked and prevented from hybridizing to a capture domain of a capture probe. Releasing the block from the capture binding enables the ligation product to specifically bind via the capture binding domain to the capture domain of the capture probe on the substrate. In some embodiments, the ligation product generated from the ligation of (i) a first oligonucleotide bound to a first analyte-binding moiety to (ii) a second oligonucleotide bound to a second analyte-binding moiety based on the proximity of the first and second analyte-binding moieties is used to determine a location of at least one analyte in a biological sample. In some embodiments, because the capture binding domain is prevented from hybridizing with the capture domain of the capture probe, inadvertent capturing of the analyte-binding moiety can be minimized, thereby reducing background signal on the substrate.

In another feature of the disclosure, the method for enhancing the specificity of binding of a first analyte-binding moiety to a first target analyte and a second analyte binding moiety to a second target analyte in a biological sample includes: (a) contacting the biological sample with a substrate, wherein the substrate includes a plurality of capture probes affixed to the substrate, wherein the capture probe includes a spatial barcode and a capture domain; (b) binding a first analyte-binding moiety to a first target analyte in the biological sample, wherein the first analyte-binding moiety is associated with a first oligonucleotide including: (i) a first barcode that identifies the first analyte-binding moiety; and (ii) a first bridge sequence; (c) binding a second analyte-binding moiety to a second target analyte in the biological sample, wherein the second analyte-binding moiety is bound to a second oligonucleotide including: (i) a capture binding domain that binds to a capture domain on a capture probe, (ii) a second barcode that identifies the second analyte-binding moiety; and (iii) a second bridge sequence; wherein the capture binding domain is blocked and prevented from hybridizing to the capture domain of the capture probe affixed to the substrate; (d) contacting the biological sample with a third oligonucleotide; (e) hybridizing the third oligonucleotide to the first bridge sequence of the first oligonucleotide and the second bridge sequence of the second oligonucleotide; (f) ligating the first oligonucleotide and the second oligonucleotide, thereby creating a ligated probe; (g) releasing the block from the capture binding domain, thereby allowing the capture binding domain of the second oligonucleotide to bind to the capture domain of the capture probe on the substrate; thereby enhancing the specificity of binding of a first analyte-binding moiety to a first target analyte and a second analyte binding moiety to a second target analyte in a biological sample.

In another feature of the disclosure, the method for enhancing the specificity of binding of a first analyte-binding moiety to a first target analyte and a second analyte binding moiety to a second target analyte in a biological sample includes: (a) contacting the biological sample with a substrate, wherein the substrate includes a plurality of capture probes affixed to the substrate, wherein the capture probe includes a spatial barcode and a capture domain; (b) binding a first analyte-binding moiety to a first target analyte in the biological sample, wherein the first analyte-binding moiety is associated with a first oligonucleotide including: (i) a first barcode that identifies the first analyte-binding moiety; and (ii) a first bridge sequence; (c) binding a second analyte-binding moiety to a second target analyte in the biological sample, wherein the second analyte-binding moiety is bound to a second oligonucleotide including: (i) a capture binding domain that binds to a capture domain on a capture probe, (ii) a second barcode that identifies the second analyte-binding moiety; and (iii) a second bridge sequence; wherein the capture binding domain includes a plurality of caged nucleotides, where a caged nucleotide of the plurality of caged nucleotides includes a caged moiety that blocks hybridization between the capture binding domain and the capture domain of the capture probe affixed to the substrate; (d) contacting the biological sample with a third oligonucleotide; (e) hybridizing the third oligonucleotide to the first bridge sequence of the first oligonucleotide and the second bridge sequence of the second oligonucleotide; (f) ligating the first oligonucleotide and the second oligonucleotide, thereby creating a ligated probe; (g) releasing through activation using photolysis the caged moiety from the caged nucleotides from the capture binding domain, thereby allowing the capture binding domain of the second oligonucleotide to bind to the capture domain of the capture probe on the substrate; thereby enhancing the specificity of binding of a first analyte-binding moiety to a first target analyte and a second analyte binding moiety to a second target analyte in a biological sample.

In another feature of the disclosure, the method for enhancing the specificity of binding of a first analyte-binding moiety to a first target analyte and a second analyte binding moiety to a second target analyte in a biological sample includes: (a) contacting the biological sample with a substrate, wherein the substrate includes a plurality of capture probes affixed to the substrate, wherein the capture probe includes a spatial barcode and a capture domain; (b) binding a first analyte-binding moiety to a first target analyte in the biological sample, wherein the first analyte-binding moiety is associated with a first oligonucleotide including: (i) a first barcode that identifies the first analyte-binding moiety; and (ii) a first bridge sequence; (c) binding a second analyte-binding moiety to a second target analyte in the biological sample, wherein the second analyte-binding moiety is bound to a second oligonucleotide including: (i) a capture binding domain that binds to a capture domain on a capture probe, (ii) a second barcode that identifies second analyte-binding moiety; and (iii) a second bridge sequence; wherein the capture binding domain includes a first sequence that hybridizes to the capture domain of the capture probe and a second sequence (e.g., a blocking probe) that hybridizes to the first sequence, wherein the se blocking probe blocks the first sequence from hybridizing to the capture domain of the capture probe affixed to the substrate; (d) contacting the biological sample with a third oligonucleotide; (e) hybridizing the third oligonucleotide to the first bridge sequence of the first oligonucleotide and the second bridge sequence of the second oligonucleotide; (f) ligating the first oligonucleotide and the second oligonucleotide, thereby creating a ligated probe; (g) releasing the blocking probe of the capture binding domain from the first sequence of the capture binding domain and allowing the capture binding domain of the second oligonucleotide to bind to the capture domain of the capture probe on the substrate; thereby enhancing the specificity of binding of a first analyte-binding moiety to a first target analyte and a second analyte binding moiety to a second target analyte in a biological sample.

Also provided herein are methods for determining (i) all or a part of the sequence of the ligation product specifically bound to the capture domain, or a complement thereof, and (ii) all or a part of the sequence of the spatial barcode, or a complement thereof, and using the determined sequence of (i) and (ii) to identify a location of the first target analyte and/or second target analyte in the biological sample.

(iii) Components of Proximity Ligation (A) First Analyte-Binding Domain and Second Analyte-Binding Domain In some embodiments, the first analyte-binding moiety is a first protein. In some embodiments, the first analyte-binding moiety is a first antibody. For example, the first antibody can include, without limitation, a monoclonal antibody, recombinant antibody, synthetic antibody, a single domain antibody, a single-chain variable fragment (scFv), and or an antigen-binding fragment (Fab). In some embodiments, the first analyte-binding moiety binds to a cell surface analyte (e.g., any of the exemplary cell surface analytes described herein). In some embodiments, binding of the analyte is performed metabolically. In some embodiments, binding of the analyte is performed enzymatically. In some embodiments, a first analyte-binding moiety is an analyte capture agent (e.g., any of the exemplary analyte capture agents described herein).

In some embodiments, the first analyte-binding moiety is a non-protein. For example, the first analyte-binding moiety is an aptamer. In some embodiments, the first analyte-binding moiety is a DNA aptamer. In some embodiments, the DNA aptamer is a single-stranded DNA molecule. In some embodiments, the first analyte-binding moiety is an RNA aptamer. In some embodiments, the aptamer is synthetic. In some embodiments, the RNA aptamer is a single-stranded RNA molecule. In some embodiments, the aptamer binds to a specific target, including but not limited to, proteins, peptides, carbohydrates, small molecules, and toxins. In some embodiments, an aptamer as disclosed herein binds into its target specifically by folding into tertiary structures.

In some embodiments, the first analyte-binding moiety binds to an analyte present inside a cell (e.g., any of the exemplary analytes present inside a cell). For example, analytes can be derived from cytosol, from cell nuclei, from mitochondria, from microsomes, and more generally, from any other compartment, organelle, or portion of a cell. In some embodiments, the first analyte-binding moiety binds to an analyte present on the surface of or outside a cell. Analytes present on the surface of or outside a cell can include without limitation, a receptor, an antigen, a surface protein, a transmembrane protein, a cluster of differentiation protein, a protein channel, a protein pump, a carrier protein, a phospholipid, a glycoprotein, a glycolipid, a cell-cell interaction protein complex, an antigen-presenting complex, a major histocompatibility complex, an engineered T-cell receptor, a T-cell receptor, a B-cell receptor, a chimeric antigen receptor, an extracellular matrix protein, a posttranslational modification (e.g., phosphorylation, glycosylation, ubiquitination, nitrosylation, methylation, acetylation or lipidation) state of a cell surface protein, a gap junction, and an adherens junction. In some embodiments, the first analyte-binding moiety is capable of binding to cell surface analytes that are post-translationally modified.

In some embodiments, the first analyte-binding moiety binds cell surface analytes that are post-translationally modified. In such embodiments, the first analyte-binding moiety can be specific for one or more cell surface analytes based on a given state of post-translational modification (e.g., phosphorylation, glycosylation, ubiquitination, nitrosylation, methylation, acetylation or lipidation), such that a cell surface analyte profile can include post-translational modification information of one or more analytes.

In some embodiments, the second analyte-binding moiety is a second protein. In some embodiments, the second analyte-binding moiety is a second antibody. For example, the second antibody can include, without limitation, a monoclonal antibody, recombinant antibody, synthetic antibody, a single domain antibody, a single-chain variable fragment (scFv), and or an antigen-binding fragment (Fab). In some embodiments, the second analyte-binding moiety binds to a cell surface analyte (e.g., any of the exemplary cell surface analytes described herein). In some embodiments, the second analyte-binding moiety binds to an analyte present inside a cell (e.g., any of the exemplary analytes present inside a cell). In some embodiments, the second analyte-binding moiety binds a non-protein. For example, the second analyte-binding moiety can bind to a nucleic acid. In some embodiments, the second analyte-binding moiety binds cell surface analytes that are post-translationally modified. In such embodiments, the second analyte-binding moiety can be specific for one or more cell surface analytes based on a given state of post-translational modification (e.g., phosphorylation, glycosylation, ubiquitination, nitrosylation, methylation, acetylation or lipidation), such that a cell surface analyte profile can include post-translational modification information of one or more analytes. In some embodiments, a second analyte-binding moiety is an analyte capture agent (e.g., any of the exemplary analyte capture agents described herein).

In some embodiments, the second analyte-binding moiety is a non-protein. For example, the second analyte-binding moiety is an aptamer. In some embodiments, the second analyte-binding moiety is a DNA aptamer. In some embodiments, the DNA aptamer is a single-stranded DNA molecule. In some embodiments, the second analyte-binding moiety is an RNA aptamer. In some embodiments, the aptamer is synthetic. In some embodiments, the RNA aptamer is a single-stranded RNA molecule. In some embodiments, the aptamer binds to a specific target, including but not limited to, proteins, peptides, carbohydrates, small molecules, and toxins. In some embodiments, an aptamer as disclosed herein binds into its target specifically by folding into tertiary structures.

In some embodiments, the second analyte-binding moiety binds to an analyte present inside a cell (e.g., any of the exemplary analytes present inside a cell). For example, analytes can be derived from cytosol, from cell nuclei, from mitochondria, from microsomes, and more generally, from any other compartment, organelle, or portion of a cell. In some embodiments, the second analyte-binding moiety binds to an analyte present on the surface of or outside a cell. Analytes present on the surface of or outside a cell can include without limitation, a receptor, an antigen, a surface protein, a transmembrane protein, a cluster of differentiation protein, a protein channel, a protein pump, a carrier protein, a phospholipid, a glycoprotein, a glycolipid, a cell-cell interaction protein complex, an antigen-presenting complex, a major histocompatibility complex, an engineered T-cell receptor, a T-cell receptor, a B-cell receptor, a chimeric antigen receptor, an extracellular matrix protein, a posttranslational modification (e.g., phosphorylation, glycosylation, ubiquitination, nitrosylation, methylation, acetylation or lipidation) state of a cell surface protein, a gap junction, and an adherens junction. In some embodiments, the second analyte-binding moiety is capable of binding to cell surface analytes that are post-translationally modified.

In some embodiments, the first analyte-binding moiety and the second analyte-binding moiety each bind to the same analyte. For example, the first analyte-binding moiety binds to a first polypeptide and the second analyte-binding moiety also binds to the first polypeptide. In some embodiments, the first analyte-binding moiety and/or second analyte-binding moiety each bind to a different analyte. For example, in some embodiments, the first analyte-binding moiety binds to a first polypeptide and the second analyte-binding moiety binds to a second polypeptide. In some embodiments, the first analyte-binding moiety binds to a first polypeptide and the second analyte-binding moiety binds to a post-translational modification of the first polypeptide. In some embodiments, the first analyte-binding moiety binds to a first polypeptide and the second analyte-binding moiety binds to a post-translational modification of a second polypeptide. In some embodiments, the first analyte-binding moiety binds to a first post-translational modification and the second analyte-binding moiety binds to a second polypeptide. In some embodiments, the first analyte-binding moiety binds to a first post-translational modification and the second analyte-binding moiety binds to a second post-translational modification of a second polypeptide.

In some embodiments, the first and/or second analyte includes, but is not limited to, lipids, carbohydrates, peptides, proteins, glycoproteins (N-linked or O-linked), lipoproteins, phosphoproteins, specific phosphorylated or acetylated variants of proteins, amidation variants of proteins, hydroxylation variants of proteins, methylation variants of proteins, ubiquitylation variants of proteins, sulfation variants of proteins, viral coat proteins, extracellular and intracellular proteins, antibodies, and antigen binding fragments.

In some embodiments, the first analyte and the second analyte interact with each other in the biological sample. In some embodiments, the first analyte and the second analyte interact with each other via a protein-protein interaction. In a non-limiting example, the first analyte can be a receptor polypeptide and a second analyte can be a ligand polypeptide.

(B) First Oligonucleotide

In some embodiments, a first oligonucleotide is bound (e.g., conjugated or otherwise attached) to a first analyte-binding moiety. For example, the first oligonucleotide can be covalently linked to the first analyte-binding moiety. In some embodiments, the first oligonucleotide is bound to the first analyte-binding moiety via its 5' end. In some embodiments, the first oligonucleotide includes a free 3' end. In some embodiments the first oligonucleotide is bound to the first analyte-binding moiety via its 3' end. In some embodiments, the first oligonucleotide includes a phosphate at its free 5' end.

In some embodiments, the oligonucleotide is bound to the first analyte-binding moiety via a first linker. For example, the first oligonucleotide is bound to the first analyte-binding moiety via a first linker. In some embodiments, the first linker is a first cleavable linker (e.g., any of the exemplary cleavable linkers described herein). In some embodiment, the first linker is a linker with photo-sensitive chemical bonds (e.g., photo-cleavable linkers). In some embodiments, the first linker is a cleavable linker that can undergo induced dissociation.

In some embodiments, a first oligonucleotide is bound to a first analyte-binding domain via a 5' end.

In some embodiments, a first oligonucleotide includes from 5' to 3': a functional sequence (e.g., any of the exemplary functional sequences described herein), a first barcode (e.g., a first analyte-binding-moiety barcode), and a first bridge sequence. In some embodiments, the functional sequence of the first oligonucleotide includes a primer sequence. The primer sequence can be used to bind a primer that can be used to amplify (i) at least part of the first oligonucleotide and (ii) at least part of any additional oligonucleotides (e.g., the first oligonucleotide) ligated to the first oligonucleotide. In some embodiments, a first oligonucleotide includes from 5' to 3': a functional sequence (e.g., any of the exemplary functional sequences described herein) and a first bridge sequence. In some embodiments, a first oligonucleotide includes from 5' to 3': a first barcode sequence (e.g., a first analyte-binding-moiety barcode), and a first bridge sequence. In some embodiments, a first oligonucleotide includes from 5' to 3': a functional sequence (e.g., any of the exemplary functional sequences described herein) and a first barcode sequence (e.g., a first analyte-binding-moiety barcode). In some embodiments, a first oligonucleotide includes from 5' to 3': a functional sequence (e.g., any of the exemplary functional sequences described herein), a first barcode sequence (e.g., a first analyte-binding-moiety barcode), and a first bridge sequence. In some embodiments, a second oligonucleotide includes from 5' to 3': a second barcode (e.g., a second analyte-binding-moiety barcode) and a functional sequence (e.g., any of the exemplary functional sequences described herein). In some embodiments, a second oligonucleotide includes from 5' to 3': a second barcode (e.g., a second analyte-binding-moiety barcode) and a capture binding domain. In some embodiments, a second oligonucleotide includes from 5' to 3': a second barcode (e.g., a second analyte-binding-moiety barcode) and a capture binding domain, where the capture binding domain includes a first sequence that binds to a capture domain of a capture probe and a second sequence (e.g., a blocking probe) that hybridizes to the first sequence to block the first sequence from hybridizing to the capture domain of the capture probe.

In some embodiments, a first oligonucleotide is bound to first analyte-binding domain via a 3' end. In some embodiments, a first oligonucleotide includes from 3' to 5': a capture binding domain sequence, a first barcode (e.g., a first analyte-binding-moiety barcode), and a first bridge sequence. In some embodiments, a first oligonucleotide includes from 3' to 5': a capture binding domain sequence and a first bridge sequence. In some embodiments, a first oligonucleotide includes from 3' to 5': a first barcode sequence (e.g., a first analyte-binding-moiety barcode) and a first bridge sequence. In some embodiments, a first oligonucleotide includes from 3' to 5': a capture binding domain sequence and a first barcode sequence (e.g., a first analyte-binding-moiety barcode). In some embodiments of any of the first oligonucleotides that include a capture binding domain, the capture binding domain includes a first sequence that binds to a capture domain of a capture probe and a second sequence (e.g., a blocking probe) that hybridizes to the first sequence to block the first sequence from hybridizing to the capture domain of the capture probe.

In some embodiments, a first barcode (e.g., a first analyte-binding-moiety barcode) is used to identify the first analyte-binding moiety to which it is bound. The first barcode can be any of the exemplary barcodes described herein. In some embodiments, the first oligonucleotide is a first capture agent barcode domain. In some embodiments, the first barcode sequence includes a first analyte-binding-moiety barcode (e.g., any of the exemplary analyte-binding-moiety barcodes described herein). In some embodiments, the first barcode sequence includes a first analyte-binding-moiety barcode and a capture binding domain (e.g., a capture binding domain that includes a first sequence that binds to a capture domain of a capture probe and as blocking probe that hybridizes to the first sequence to block the first sequence from hybridizing to the capture domain of the capture probe).

(C) Second Oligonucleotide

In some embodiments, a second oligonucleotide is bound (e.g., conjugated or otherwise attached) to a second analyte-binding moiety. For example, the second oligonucleotide can be covalently linked to the second analyte-binding moiety. In some embodiments, the second oligonucleotide is bound to the second analyte-binding moiety via its 5' end. In some embodiments, the second oligonucleotide includes a free 3' end. In some embodiments the second oligonucleotide is bound to the second analyte-binding moiety via its 3' end. In some embodiments, the second oligonucleotide includes a free 5' end.

In some embodiments, the oligonucleotide is bound to the second analyte-binding moiety via a second linker (e.g., any of the exemplary linkers described herein). For example, the second oligonucleotide is bound to the second analyte-binding moiety via a second linker. In some embodiments, the second linker is a second cleavable linker (e.g., any of the exemplary cleavable linkers described herein). In some embodiment, the second linker is a linker with photosensitive chemical bonds (e.g., photo-cleavable linkers). In some embodiments, the second linker is a cleavable linker that can undergo induced dissociation.

In some embodiments, a second oligonucleotide is bound (e.g., attached via any of the methods described herein) to a second analyte-binding domain via a 3' end. In some embodiments, a second oligonucleotide includes from 3' to 5': a capture binding domain, a second barcode (e.g., a second analyte-binding-moiety barcode), and a second bridge sequence. In some embodiments, a second oligonucleotide includes from 3' to 5': a capture binding domain and a second bridge sequence. In some embodiments, a second oligonucleotide includes from 3' to 5': a second barcode and a second bridge sequence. In some embodiments of any of the second oligonucleotides bound to a second analyte-binding domain where the second oligonucleotide includes a capture binding domain, the capture binding domain includes a first sequence that binds to a capture domain of a capture probe and a second sequence (e.g, a blocking probe) that hybridizes to the first sequence to block the first sequence from hybridizing to the capture domain of the capture probe. In some embodiments of any of the second oligonucleotides bound to a second analyte-binding domain where the second oligonucleotide includes a capture binding domain, the capture binding domains includes caged nucleotides (e.g., any of the caged nucleotides described herein).

In some embodiments, a second oligonucleotide is bound (e.g., attached via any of the methods described herein) to a second analyte-binding domain via a 5' end. In some embodiments, a second oligonucleotide includes from 5' to 3': a second barcode (e.g., a second analyte-binding-moiety barcode) and a capture binding domain. In some embodiments, a second oligonucleotide includes from 5' to 3': a functional sequence and a capture binding domain. In some embodiments, a second oligonucleotide includes from 5' to 3': a second barcode (e.g., a second analyte-binding-moiety barcode) and a capture binding domain that includes a plurality of caged nucleotides. In some embodiments, a second oligonucleotide includes from 5' to 3': a functional sequence and a capture binding domain that includes a plurality of caged nucleotides. In some embodiments, the functional sequence is a primer sequence. The primer sequence can be used to bind a primer that can be used to amplify (i) at least part of the second oligonucleotide. In some embodiments of any of the second oligonucleotides bound to a second analyte-binding domain where the second oligonucleotide includes a capture binding domain, the capture binding domain includes a first sequence that binds to a capture domain of a capture probe and a second sequence (e.g, a blocking probe) that hybridizes to the first sequence to block the first sequence from hybridizing to the capture domain of the capture probe. In some embodiments of any of the second oligonucleotides bound to a second analyte-binding domain where the second oligonucleotide includes a capture binding domain, the capture binding domains includes caged nucleotides (e.g., any of the caged nucleotides described herein).

In some embodiments, a second barcode (e.g., a second analyte-binding-moiety barcode) is used to identify the second analyte-binding moiety to which it is bound. The second barcode can be any of the exemplary barcodes described herein.

In some embodiments, the second oligonucleotide is a second capture agent barcode domain. In some embodiments, the second capture agent barcode domain includes a second analyte-binding-moiety barcode (e.g., any of the exemplary analyte-binding-moiety barcodes described herein). In some embodiments, the second capture agent barcode domain includes a second analyte-binding-moiety barcode and a second capture binding domain.

In some embodiments, a first oligonucleotide is bound to a first analyte-binding domain via a 5' end and a second oligonucleotide is bound (e.g., attached via any of the method described herein) to a second analyte-binding domain via a 3' end. In some embodiments, a first oligonucleotide includes from 5' to 3': a functional sequence (e.g., any of the exemplary functional sequences described herein), a first barcode (e.g., a first analyte-binding-moiety barcode), and a first bridge sequence, and a second oligonucleotide includes from 3' to 5': a capture binding domain (e.g., including a first sequence that binds to a capture domain of a capture probe and a second sequence (e.g., a blocking probe) that binds to the first sequence, a second barcode (e.g., a second analyte-binding-moiety barcode), and a second bridge sequence. In some embodiments, a first oligonucleotide includes from 5' to 3': a functional sequence (e.g., any of the exemplary functional sequences described herein), a first barcode (e.g., a first analyte-binding-moiety barcode), and a first bridge sequence, and a second oligonucleotide includes from 3' to 5': a capture binding domain that includes a plurality of caged nucleotides, a second barcode (e.g., a second analyte-binding-moiety barcode), and a second bridge sequence.

In some embodiments of any of the methods of determining a location of at least one analyte in a biological sample, a first oligonucleotide is bound (e.g., attached via any of the methods described herein) to a first analyte-binding domain via a 5' end and a second oligonucleotide is bound (e.g., attached via any of the method described herein) to a second analyte-binding domain via a 5' end. In some embodiments, a first oligonucleotide includes from 5' to 3': a functional sequence (e.g., any of the exemplary functional sequences described herein) and a first barcode (e.g., a first analyte-binding-moiety barcode), and a second oligonucleotide includes from 5' to 3': a second barcode (e.g., a second analyte-binding-moiety barcode) and a capture binding domain. In some embodiments, a first oligonucleotide includes from 5' to 3': a functional sequence (e.g., any of the exemplary functional sequences described herein) and a first barcode (e.g., a first analyte-binding-moiety barcode), and a second oligonucleotide includes from 5' to 3': a second barcode (e.g., a second analyte-binding-moiety barcode), and a capture binding domain that includes a plurality of caged nucleotides. In some embodiments of any of the second oligonucleotides bound to a second analyte-binding domain where the second oligonucleotide includes a capture binding domain, the capture binding domain includes a first sequence that binds to a capture domain of a capture probe and a second sequence (e.g., a blocking probe) that hybridizes to the first sequence to block the first sequence from hybridizing to the capture domain of the capture probe. In some embodiments of any of the second oligonucleotides bound to a second analyte-binding domain where the second oligonucleotide includes a capture binding domain, the capture binding domain includes caged nucleotides (e.g., any of the caged nucleotides described herein).

(D) Third Oligonucleotide

In some embodiments of any of the methods of determining a location of at least one analyte in a biological sample, a third oligonucleotide is hybridized to the first oligonucleotide and the second oligonucleotide via the first bridge sequence and the second bridge sequence, respectively. In some embodiments, a first portion of the third oligonucleotide is at least partially complementary to the first bridge sequence. In some embodiments, a second portion of the third oligonucleotide is at least partially complementary to the second bridge sequence. In some embodiments, the third oligonucleotide hybridizes to the first bridge sequence prior to hybridizing to the second bridge sequence. In some embodiments, the third oligonucleotide hybridizes to the second bridge sequence prior to hybridizing to the first bridge sequence. In some embodiments, the third oligonucleotide hybridizes simultaneously to the first bridge sequence and the second bridge sequence.

In some embodiments, a third oligonucleotide is hybridized to the first oligonucleotide and the second oligonucleotide via the first barcode and the second barcode, respectively. In some embodiments, a first sequence of the third oligonucleotide is at least partially complementary to the first barcode. In some embodiments, a second sequence of the third oligonucleotide is at least partially complementary to the second barcode. In some embodiments, the third oligonucleotide hybridizes to the first barcode prior to hybridizing to the second barcode. In some embodiments, the third oligonucleotide hybridizes to the second barcode prior to hybridizing to the first barcode. In some embodiments, the third oligonucleotide hybridizes simultaneously to the first barcode and the second barcode. In some embodiments, a third oligonucleotide includes from 5' to 3' a second portion that binds to a sequence of the second oligonucleotide (e.g., a second barcode) and a first portion that binds to a sequence of the first oligonucleotide (e.g., a first barcode). In some embodiments, a third oligonucleotide includes from 5' to 3' a first sequence that binds to a sequence of the first oligonucleotide (e.g., a first barcode) and a second sequence that binds to a sequence of the second oligonucleotide (e.g., a second barcode).

In some embodiments, the third oligonucleotide includes a sequence of about 10 nucleotides to about 100 nucleotides (e.g., a sequence of about 10 nucleotides to about 90 nucleotides, about 10 nucleotides to about 80 nucleotides, about 10 nucleotides to about 70 nucleotides, about 10 nucleotides to about 60 nucleotides, about 10 nucleotides to about 50 nucleotides, about 10 nucleotides to about 40 nucleotides, about 10 nucleotides to about 30 nucleotides, about 10 nucleotides to about 20 nucleotides, about 20 nucleotides to about 90 nucleotides, about 20 nucleotides to about 80 nucleotides, about 20 nucleotides to about 70 nucleotides, about 20 nucleotides to about 60 nucleotides, about 20 nucleotides to about 50 nucleotides, about 20 nucleotides to about 40 nucleotides, about 20 nucleotides to about 30 nucleotides, about 30 nucleotides to about 90 nucleotides, about 30 nucleotides to about 80 nucleotides, about 30 nucleotides to about 70 nucleotides, about 30 nucleotides to about 60 nucleotides, about 30 nucleotides to about 50 nucleotides, about 30 nucleotides to about 40 nucleotides, about 40 nucleotides to about 90 nucleotides, about 40 nucleotides to about 80 nucleotides, about 40 nucleotides to about 70 nucleotides, about 40 nucleotides to about 60 nucleotides, about 40 nucleotides to about 50 nucleotides, about 50 nucleotides to about 90 nucleotides, about 50 nucleotides to about 80 nucleotides, about 50 nucleotides to about 70 nucleotides, about 50 nucleotides to about 60 nucleotides, about 60 nucleotides to about 90 nucleotides, about 60 nucleotides to about 80 nucleotides, about 60 nucleotides to about 70 nucleotides, about 70 nucleotides to about 90 nucleotides, about 70 nucleotides to about 80 nucleotides, or about 80 nucleotides to about 90 nucleotides).

In some embodiments, the third oligonucleotide hybridized to both the first bridge sequence and second bridge sequence enables ligation of the first oligonucleotide and the second oligonucleotide. In some embodiments, a ligase is used. In some aspects, the ligase includes a DNA ligase. In some aspects, the ligase includes RNA ligase. In some aspects, the ligase includes one or more of a T4 RNA ligase (Rnl2), a SplintR® ligase, a single stranded DNA ligase, or a T4 DNA ligase. In some aspects, the ligase is a T4 RNA ligase 2 (Rnl2) ligase.

In some embodiments, the ligation of the first oligonucleotide and the second oligonucleotide includes enzymatic or chemical ligation. In some embodiments, the ligation of the first oligonucleotide and the second oligonucleotide includes enzymatic ligation. In some embodiments, the ligation reaction utilizes ligase (e.g., any of the exemplary ligases described herein). For example, the ligase is a SplintR® ligase.

In some aspects, the methods include "sticky-end" or "blunt-end" ligations. Additionally, single-stranded ligation can be used to perform proximity ligation on a single-stranded nucleic acid molecule.

In some embodiments, the ligase creates a ligation product (e.g., a full length oligonucleotide) that includes both the first oligonucleotide and the second oligonucleotide. In some embodiments, a third oligonucleotide hybridizes to a first oligonucleotide and a second oligonucleotide when the first analyte-binding domain and the second analyte-binding domain are about 400 nm distance (e.g., about 300 nm, about 200 nm, about 150 nm, about 100 nm, about 50 nm, about 25 nm, about 10 nm, or about 5 nm) from each other.

In some embodiments, when the third oligonucleotide is hybridized to the first bridge sequence and the second bridge sequence, the first oligonucleotide and the second oligonucleotide are directly adjacent in a manner that enables ligation in the presence of a ligase enzyme. In some embodiments, when the first oligonucleotide and the second nucleotide are directly adjacent to each other, a ligation reaction occurs between a free 3' of the first oligonucleotide and a 5' of the second oligonucleotide that includes a phosphorylated end. In some embodiments, when the first oligonucleotide and the second oligonucleotide are directly adjacent to each other, a ligation reaction occurs directly between a free 3' end of the second oligonucleotide and a phosphorylated 5' end of the first oligonucleotide. In some embodiments, when the third oligonucleotide is hybridized to the first bridge sequence and the second bridge sequence, the first oligonucleotide and the second oligonucleotide are not directly adjacent. For example, when the third oligonucleotide is hybridized to the first bridge sequence and the second bridge sequence, the first oligonucleotide and the second oligonucleotide requires additional nucleotides to hybridize to the third oligonucleotide in between the first and second oligonucleotides in order for a ligation product to be generated. In some embodiments, additional nucleotide sequences can be added between the first oligonucleotide and the second oligonucleotide by DNA polymerases (e.g., any of the exemplary DNA polymerases described herein).

In some embodiments, the third oligonucleotide is designed so that a portion of the nucleic acid sequence of the third oligonucleotide does not hybridize to either the first bridge sequence or the second bridge sequence. This portion of the third oligonucleotide can be located between the first sequence that is complementary to the first bridge sequence and the second sequence that is complementary to the second bridge sequence. In some embodiments, the third oligonucleotide is designed so that a portion of the nucleic acid sequence of the third oligonucleotide does not hybridize to either the first barcode or the second barcode. This portion of the third oligonucleotide can be located between the first sequence that is complementary to the first barcode and the second sequence that is complementary to the second barcode. In some embodiments, the portion of the of the nucleic acid sequence of the third oligonucleotide that does not hybridize to the first or second bridge sequence forms a secondary structure (e.g., stem-loop, hairpins, or other structure typically formed by single stranded DNA).

(E) Bridge Sequence (in the First and Second Oligonucleotides)

In some embodiments, the first oligonucleotide and/or the second oligonucleotides include a bridge sequence. In some embodiments, the first oligonucleotide includes a bridge sequence. In some embodiments, the second oligonucleotide includes a bridge sequence. As used herein, a "bridge sequence" refers to a sequence that is at least partially complementary to a third oligonucleotide and functions to bring the a first sequence and a second sequence in sufficient proximity that the first and second sequences can be ligated together. In some aspects, the bridge sequence of the first oligonucleotide has at least 80%, at least 85%, at least 90%, at least 91%, at least 92%, at least 93%, at least 94%, at least 95%, at least 96%, at least 97%, at least 98%, or at least 99% sequence identity to a sequence that is 100% complimentary to the third oligonucleotide sequence. In some aspects, the bridge sequence of the second oligonucleotide has at least 80%, at least 85%, at least 90%, at least 91%, at least 92%, at least 93%, at least 94%, at least 95%, at least 96%, at least 97%, at least 98%, or at least 99% sequence identity to a sequence that is 100% complimentary to the third oligonucleotide sequence. In some embodiments, a bridge sequence (e.g., a first bridge sequence and/or a second bridge sequence) is about 5 nucleotides to about 50 nucleotides (e.g., about 5 nucleotides to about 45 nucleotides, about 5 nucleotides to about 40 nucleotides, about 5 nucleotides to about 35 nucleotides, about 5 nucleotides to about 30 nucleotides, about 5 nucleotides to about 25 nucleotides, about 5 nucleotides to about 20 nucleotides, about 5 nucleotides to about 15 nucleotides, about 5 nucleotides to about 10 nucleotides, about 10 nucleotides to about 45 nucleotides, about 10 nucleotides to about 40 nucleotides, about 10 nucleotides to about 35 nucleotides, about 10 nucleotides to about 30 nucleotides, about 10 nucleotides to about 25 nucleotides, about 10 nucleotides to about 20 nucleotides, about 10 nucleotides to about 15 nucleotides, about 15 nucleotides to about 45 nucleotides, about 15 nucleotides to about 40 nucleotides, about 15 nucleotides to about 35 nucleotides, about 15 nucleotides to about 30 nucleotides, about 15 nucleotides to about 25 nucleotides, about 15 nucleotides to about 20 nucleotides, about 20 nucleotides to about 45 nucleotides, about 20 nucleotides to about 40 nucleotides, about 20 nucleotides to about 35 nucleotides, about 20 nucleotides to about 30 nucleotides, about 20 nucleotides to about 25 nucleotides, about 25 nucleotides to about 45 nucleotides, about 25 nucleotides to about 40 nucleotides, about 25 nucleotides to about 35 nucleotides, about 25 nucleotides to about 30 nucleotides, about 30 nucleotides to about 45 nucleotides, about 30 nucleotides to about 40 nucleotides, about 30 nucleotides to about 35 nucleotides, about 35 nucleotides to about 45 nucleotides, about 35 nucleotides to about 40 nucleotides, or about 40 nucleotides to about 45 nucleotides). In some embodiments, a bridge sequence is a functional sequence (e.g., any of the exemplary functional sequence described herein).

(d) Methods of Enhancing Detection of Nucleic Acid Analytes (i) Spatially Detecting Nucleic Acid Analytes Using Blocking Probes Disclosed herein are methods of detecting the location and/or the abundance of a nucleic acid analyte. Also disclosed are methods of blocking capture binding domains on an analyte before it is detected by a capture probe on a substrate. For example, in some instances, the methods include placing a biological sample (i.e., any biological sample disclosed herein) on a substrate that has a plurality of capture probes. In some instances, blocking probes are added to the sample and blocking probes interact with a capture binding domain in a nucleic acid analyte (e.g., a poly(A) sequence of an mRNA), thereby blocking the nucleic acid analytes from binding prematurely or binding to other molecules in an untimely and unwanted manner in a biological sample. Thus, the methods disclosed herein allow for nucleic acid analytes, such as mRNA, to be captured with increased efficiency and/or less background. In some instances, blocking is reversible using methods disclosed herein. In some instances, the blocking probe is released from the analyte prior to contacting the analyte with the capture probes.

(ii) RNA Templated Ligation Using Blocking Probes

RNA templated ligation (RTL) is a process that includes multiple oligonucleotides (e.g., oligonucleotide probes) that hybridize to adjacent complementary nucleic acid analyte sequences. Upon hybridization, the two oligonucleotides are ligated to one another, creating a ligation product that can be used as a proxy for the target nucleic acid analyte, but only in the event that both oligonucleotides hybridize to their respective complementary sequences. In some instances, at least one of the oligonucleotides includes a capture binding domain and a blocking domain. The blocking domain prevents the premature interaction of the capture binding domain with a capture domain on a capture probe on an array described herein. In some instances, the blocking domain is released prior to contacting the ligation product with the array that includes the capture probes. In some instances, also prior to hybridization of the capture binding domain to the capture domain of a capture probe, an endonuclease digests the blocking domain that is hybridized to the ligation product. This step frees the newly formed ligation product to hybridize to the capture probe once the blocking domain is removed from the capture binding domain. In this way, RTL that includes a blocking domain and/or caged nucleotides provides a method to perform targeted RNA capture with increased efficiency.

Targeted RNA capture allows for the examination of a subset of RNA analytes from the entire transcriptome, in its broadest application. One limitation of targeted RNA capture is the ability to accurately detect genetic variants within a subset of RNA analytes. Current limitations are driven by probe design requirements (e.g., a first probe oligonucleotide and/or a second probe oligonucleotide need to incorporate the genetic variation into the probe sequence in order to detect the variation on the complement strand (e.g., the RNA analyte)). Provided herein are methods for identifying a location of an analyte in a biological sample based on (i) probe oligonucleotides that include a blocking domain and/ or caged nucleotides that prevent premature interaction of the capture binding domain with the capture domain of the capture probe, (ii) blocking the interaction of the capture binding domain with a capture probe, and (iii) releasing the blocking domain and/or caged nucleotides thereby allowing the capture binding domain to interact with the capture domain on the capture probe at the appropriate time to enhance the capture of the ligation product by the capture probe and/or decrease background binding. The methods provided herein prevent premature interaction between capture binding domains and capture domain, thereby increasing the resolution of the RNA template ligation technology.

In some embodiments, the subset of analytes includes an individual target RNA. In some instances, the presence of the ligation product that is created as a result of the RTL methods described herein indicates that the individual target RNA is present. In some instances, the absence of the ligation product that is created as a result of the RTL methods described herein indicates that the individual target RNA is present. In some instances, an absence of the ligation product is because one of the oligonucleotide probes did not hybridize to the analyte. In some instances, an absence of the ligation product is because at least one or both of the oligonucleotide probes did not hybridize to the analyte.

In some embodiments, the subset of analytes detected using methods disclosed herein includes two or more (e.g., 2, 3, 4, 5, 6, 7, 8, 9, 10, or more) targeted RNAs. In some embodiments, the subset of analytes includes one or more mRNAs transcribed by a single gene. In some embodiments, the subset of analytes includes one or more mRNAs transcribed by more than one targeted gene. In some embodiments, the subset of analytes includes one or more mRNA splice variants of one or more targeted genes. In some embodiments, the subset of analytes includes non-polyadenylated RNAs in a biological sample. In some embodiments, the subset of analytes includes detection of mRNAs having one or more single nucleotide polymorphisms (SNPs) in a biological sample.

In some embodiments, the subset of analytes includes mRNAs that mediate expression of a set of genes of interest. For example, in some instances, the subset of analytes detected using the RTL methods disclosed herein include analytes that are translated into transcription factors that control one or more cellular pathways. In some embodiments, the subset of analytes includes mRNAs that share identical or substantially similar sequences, which mRNAs are translated into polypeptides having similar functional groups or protein domains. In some embodiments, the subset of analytes includes mRNAs that do not share identical or substantially similar sequences, which mRNAs are translated into proteins that do not share similar functional groups or protein domains. In some embodiments, the subset of analytes includes mRNAs that are translated into proteins that function in the same or similar biological pathways. In some embodiments, the biological pathways are associated with a pathologic disease. For example, targeted RNA capture can detect genes that are overexpressed or underexpressed in a cancer sample. In some embodiments, the targeted RNA capture can detect diseases, cancers, or monitor the efficacy of disease or cancer treatments or therapies based on gene expression profiles. In some embodiments, targeted RNA capture can be used to identify rare and undiagnosed genetic diseases by gene expression patterns of, for example, rare mRNAs.

In some embodiments, the subset of analytes includes 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, about 55, about 60, about 65, about 70, about 75, about 80, about 85, about 90, about 95, about 100, about 110, about 120, about 130, about 140, about 150, about 160, about 170, about 180, about 190, about 200, about 225, about 250, about 275, about 300, about 325, about 350, about 375, about 400, about 425, about 450, about 475, about 500, about 600, about 700, about 800, about 900, about 1000, or more analytes.

In some embodiments, the subset of analytes detected by targeted RNA capture methods provided herein includes a large proportion of the transcriptome of one or more cells. For example, the subset of analytes detected by targeted RNA capture methods provided herein can include at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or more of the mRNAs present in the transcriptome of one or more cells.

Methods disclosed herein can be performed on any type of sample. In some embodiments, the sample is a fresh tissue. In some embodiments, the sample is a frozen sample. In some embodiments, the sample was previously frozen. In some embodiments, the sample is a formalin-fixed, paraffin embedded (FFPE) sample. FFPE samples generally are heavily cross-linked and fragmented, and therefore this type of sample allows for limited RNA recovery using conventional detection techniques. In certain embodiments, methods of targeted RNA capture provided herein are less affected by RNA degradation associated with FFPE fixation than other methods (e.g., methods that take advantage of oligo-dT capture and reverse transcription of mRNA). In certain embodiments, methods provided herein enable sensitive measurement of specific genes of interest that otherwise might be missed with a whole transcriptomic approach.

In some embodiments, a biological sample (e.g. tissue section) can be fixed with methanol, stained with hematoxylin and eosin, and imaged. In some embodiments, fixing, staining, and imaging occurs before one or more oligonucleotide probes are hybridized to the sample. Some embodiments of any of the workflows described herein can further include a destaining step (e.g., a hematoxylin and eosin destaining step), after imaging of the sample and prior to permeabilizing the sample. For example, destaining can be performed by performing one or more (e.g., one, two, three, four, or five) washing steps (e.g., one or more (e.g., one, two, three, four, or five) washing steps performed using a buffer including HCl). The images can be used to map spatial gene expression patterns back to the biological sample. A permeabilization enzyme can be used to permeabilize the biological sample directly on the slide.

In another feature of the disclosure, provided herein is a method for enhancing the specificity of binding of an oligonucleotide to a target analyte in a biological sample, where the method includes: (a) contacting the biological sample with a substrate, wherein the substrate includes a plurality of capture probes affixed to the substrate, wherein the capture probe includes a spatial barcode and the capture domain; (b) binding a first probe oligonucleotide and a second probe oligonucleotide to a target analyte in the biological sample, wherein: the first probe oligonucleotide and the second probe oligonucleotide are substantially complementary to adjacent sequences of the analyte, the second probe oligonucleotide includes a capture binding domain that binds to a capture domain of a capture probe, wherein the capture binding domain is blocked and prevented from hybridizing to the capture domain of the capture probe affixed to the substrate; (c) ligating the first probe oligonucleotide and the second probe oligonucleotide, thereby creating a ligated probe that is substantially complementary to the analyte; (d) releasing: the ligated probe from the analyte, and the block from the capture binding domain, thereby allowing the capture binding domain to bind to the capture domain of the capture probe on the substrate, thereby enhancing the specificity of binding of a polynucleotide to a target analyte in a biological sample.

In another feature of the disclosure, provided herein is a method for enhancing the specificity of binding of an oligonucleotide to a target analyte in a biological sample, where the method includes: (a) contacting the biological sample with a substrate, wherein the substrate includes a plurality of capture probes affixed to the substrate, wherein the capture probe includes a spatial barcode and the capture domain (b) binding a first probe oligonucleotide and a second probe oligonucleotide to a target analyte in the biological sample, wherein: the first probe oligonucleotide and the second probe oligonucleotide are substantially complementary to adjacent sequences of the analyte, the second probe oligonucleotide includes a capture binding domain that binds to a capture domain of a capture probe, wherein the capture binding domain includes a plurality of caged nucleotides, where a caged nucleotide of the plurality of caged nucleotides includes a caged moiety that blocks hybridization between the capture binding domain and the capture domain of the capture probe affixed to the substrate; (c) ligating the first probe oligonucleotide and the second probe oligonucleotide, thereby creating a ligated probe that is substantially complementary to the analyte; (d) releasing: the ligated probe from the analyte, and the caged moiety from each of the caged nucleotides from the capture binding domain through activation using photolysis, thereby allowing the capture binding domain of the second oligonucleotide to specifically bind to the capture domain of the capture probe on the substrate; thereby enhancing the specificity of binding of a first analyte-binding moiety to a first target analyte and a second analyte binding moiety to a second target analyte in a biological sample.

In another feature of the disclosure, provided herein is a method for enhancing the specificity of binding of a oligonucleotide to a target analyte in a biological sample, where the method includes: (a) contacting the biological sample with a substrate, wherein the substrate includes a plurality of capture probes affixed to the substrate, wherein the capture probe includes a spatial barcode and the capture domain (b) binding a first probe oligonucleotide and a second probe oligonucleotide to a target analyte in the biological sample, wherein: the first probe oligonucleotide and the second probe oligonucleotide are substantially complementary to adjacent sequences of the analyte, the second probe oligonucleotide includes a capture binding domain that binds to a capture domain of a capture probe, wherein the capture binding domain includes a first sequence (i.e., a capture binding domain) that hybridizes to the capture domain of the capture probe and a second sequence (e.g., a blocking probe) that hybridizes to the first sequence, wherein the blocking probe blocks the first sequence from hybridizing to the capture domain of the capture probe affixed to the substrate; (c) ligating the first probe oligonucleotide and the second probe oligonucleotide, thereby creating a ligated probe that is substantially complementary to the analyte; (d) releasing: the ligated probe from the analyte, and the blocking probe of the capture binding domain from the first sequence of the capture binding domain and allowing the capture binding domain to specifically bind to the capture domain of the capture probe on the substrate, thereby enhancing the specificity.

Also provided herein are methods for determining (i) all or a part of the sequence of the ligated probe specifically bound to the capture domain, or a complement thereof, and (ii) all or a part of the sequence of the spatial barcode, or a complement thereof, and using the determined sequence of (i) and (ii) to identify a location of a target analyte in the biological sample.

In some embodiments, the RTL methods that allow for targeted RNA capture as provided herein include a first probe oligonucleotide and a second probe oligonucleotide. The first and second probe oligonucleotides each include sequences that are substantially complementary to the sequence of an analyte of interest. By substantially complementary, it is meant that the first and/or second probe oligonucleotide is at least 70%, at least 75%, at least 80%, at least 85%, at least 90%, at least 91%, at least 92%, at least 93%, at least 94%, at least 95%, at least 96%, at least 97%, at least 98%, at least 99%, or 100% complementary to a sequence in an analyte. In some instances, the first probe oligonucleotide and the second probe oligonucleotide hybridize to adjacent sequences on an analyte. Methods provided herein may be applied to hybridization of two or more probe oligonucleotides to a single nucleic acid molecule. In some embodiments, each target analyte includes a first target region and a second target region. In some instances, the methods include providing a plurality of first probe oligonucleotides and a plurality of second probe oligonucleotides. In some instances, a first probe oligonucleotide hybridizes to a first target region of the nucleic acid. In some instances, a second probe oligonucleotide hybridizes to a second target region of the nucleic acid.

In some embodiments, the first and/or second probe oligonucleotide as disclosed herein includes one of at least two ribonucleic acid bases at the 3' end; a functional sequence; a phosphorylated nucleotide at the 5' end; and/or a capture binding domain. In some embodiments, the first and/or second probe as disclosed herein includes one of at least two ribonucleic acid bases at the 3' end; a functional sequence; a phosphorylated nucleotide at the 5' end; and/or a capture binding domain that includes a plurality of caged nucleotides. In some embodiments, the first and/or second probe as disclosed herein includes one of at least two ribonucleic acid bases at the 3' end; a functional sequence; a phosphorylated nucleotide at the 5' end; and a capture binding domain. In some embodiments, the capture binding domain includes a first sequence that binds to a capture domain of a capture probe and a second sequence (e.g., a blocking probe) that hybridizes to the first sequence to prevent interaction of the first sequence with the capture domain of the capture probe. In some embodiments, the functional sequence is a primer sequence. The capture binding domain is a sequence that is complementary to a particular capture domain present in a capture probe. The first sequence of the capture binding domain includes a sequence that is substantially complementary to a portion of the capture domain. In some embodiments, the capture binding domain includes a poly(A) sequence. In some embodiments, the capture binding domain includes a poly-uridine sequence, a poly-thymidine sequence, or both. In some embodiments, the capture binding domain includes a random sequence (e.g., a random hexamer or octamer). In some embodiments, the capture binding domain is complementary to a capture domain in a capture probe that detects a particular target(s) of interest. In some embodiments, the capture binding domain includes a poly-uridine sequence and/or a poly-thymidine sequence, and the blocking domain includes a poly-adenosine sequence. In some embodiments, the capture binding domain includes a random sequence (e.g., a random hexamer or octamer). In some embodiments, the capture binding domain is complementary to a capture domain in a capture probe that detects a particular target(s) of interest.

In some embodiments, the first probe oligonucleotide hybridizes to an analyte. In some embodiments, the second probe oligonucleotide hybridizes to an analyte. In some embodiments, both the first probe oligonucleotide and the second probe oligonucleotide hybridize to an analyte. Hybridization can occur at a target having a sequence that is 100% complementary to the probe oligonucleotide(s). In some embodiments, hybridization can occur at a target having a sequence that is at least (e.g. at least about) 80%, at least (e.g. at least about) 85%, at least (e.g. at least about) 90%, at least (e.g. at least about) 95%, at least (e.g. at least about) 96%, at least (e.g. at least about) 97%, at least (e.g. at least about) 98%, or at least (e.g. at least about) 99% complementary to the probe oligonucleotide(s).

After hybridization of the first and second probe oligonucleotides, in some embodiments, the first probe oligonucleotide is extended. After hybridization, in some embodiments, the second probe oligonucleotide is extended. In some instances, a polymerase (e.g., a DNA polymerase) extends the first and/or second oligonucleotide.

In some embodiments, methods disclosed herein include a wash step. In some instances, the wash step occurs after hybridizing the first and the second probe oligonucleotides. The wash step removes any unbound oligonucleotides and can be performed using any technique or solution disclosed herein or known in the art. In some embodiments, multiple wash steps are performed to remove unbound oligonucleotides.

In some instances, the first and second target regions of the first probe oligonucleotide and the second probe oligonucleotide are adjacent to one another. In some embodiments, the first and second probe oligonucleotides bind to complementary sequences on the same transcript. In some embodiments, the complementary sequences to which the first probe oligonucleotide and the second probe oligonucleotide bind are 1, 2, 3, 4, 5, 6, 7, 8, 9, 10, about 15, about 20, about 25, about 30, about 35, about 40, about 45, about 50, about 55, about 60, about 65, about 70, about 75, about 80, about 85, about 90, about 95, about 100, about 125, or about 150 nucleotides away from each other. Gaps between the probe oligonucleotides may first be filled prior to ligation, using, for example, dNTPs in combination with a polymerase such as Mu polymerase, DNA polymerase, RNA polymerase, reverse transcriptase, Taq polymerase, and/or any combinations, derivatives, and variants (e.g., engineered mutants) thereof. In some embodiments, when the first and second probe oligonucleotides are separated from each other by one or more nucleotides, deoxyribonucleotides are used to extend and ligate the first and second probe oligonucleotides.

In some instances, the first probe oligonucleotide and the second probe oligonucleotide hybridize to an analyte on the same transcript. In some instances, the first probe oligonucleotide and the second probe oligonucleotide hybridize to an analyte on the same exon. In some instances, the first probe oligonucleotide and the second probe oligonucleotide hybridize to an analyte on different exons. In some instances, the first probe oligonucleotide and the second probe oligonucleotide hybridize to an analyte that is the result of a translocation event (e.g., in the setting of cancer). The methods provided herein make it possible to identify alternative splicing events, translocation events, and mutations that change the hybridization rate of one or both probe oligonucleotides (e.g., single nucleotide polymorphisms, insertions, deletions, point mutations).

In some embodiments, after hybridization of probe oligonucleotides (e.g., first and the second probe oligonucleotides) to the analyte, the probe oligonucleotides (e.g., the first probe oligonucleotide and the second probe oligonucleotide) are ligated together, creating a single ligated probe that is complementary to the analyte. Ligation can be performed enzymatically or chemically, as described herein.

In some instances, the first and second probe oligonucleotides are hybridized to the first and second target regions of the analyte, and the probe oligonucleotides are subjected to a nucleic acid reaction to ligate them together. In some instances, the ligation is enzymatic. In some instances, the ligation reaction catalyzed by a ligase disclosed herein occurs in the following steps. In some instances, the ligase enzyme is pre-activated by charging with ATP. Addition of ATP to ligase enzyme causes formation of an intermediate AMP-enzyme species concomitant with hydrolysis of ATP to yield AMP. In some instances, the pre-activating step does not occur. In some instances, the next step includes methods where the charged AMP-enzyme intermediate binds to the dsDNA (or dsRNA, or RNA/DNA complex) and transfers the AMP moiety to the free 5' terminal phosphate, to form a high energy 5'-5' phosphate bond. In some instances, the third step includes methods wherein the enzyme provides the appropriate environment in which the 3' hydroxyl group of the second strand of DNA (or RNA) is able to attach the high energy 5'-5' phosphate bond, thereby forming a covalent phosphodiester bond as a product and releasing ligase enzyme and AMP. Free enzyme does not bind the intermediate high energy 5'-5' phosphate bond species to an appreciable amount. Thus, if the ligase prematurely releases from the duplex after formation of the high energy 5'-5' phosphate bond, the reaction will typically end and the intermediate will not proceed to the final ligated product.

In some instances, the probes may be subjected to an enzymatic ligation reaction, using a ligase (e.g., T4 RNA ligase (Rnl2), a splintR ligase, a single stranded DNA ligase, or a T4 DNA ligase). See, e.g., Zhang L., et al.; Archaeal RNA ligase from *Thermoccocus kodakarensis* for template dependent ligation RNA Biol. 2017; 14(1): 36-44, which is incorporated by reference in its entirety, for a description of KOD ligase. In some instances, the ligase is T4 RNA ligase (Rnl2). T4 DNA ligase is an enzyme belonging to the DNA ligase family of enzymes that catalyzes the formation of a covalent phosphodiester bond from a free 3' hydroxyl group on one DNA molecule and a free 5' phosphate group of a second, separate DNA molecule, thus covalently linking the two DNA strands together to form a single DNA strand. In some instances, the ligase is splintR ligase. SplintR Ligase, also known as PBCV-1 DNA Ligase or *Chlorella* virus DNA Ligase, efficiently catalyzes the ligation of adjacent, single-stranded DNA oligonucleotides splinted by a complementary RNA strand. In some instances, the ligase is a single-stranded DNA ligase.

In some embodiments, adenosine triphosphate (ATP) is added during the ligation reaction. DNA ligase-catalyzed sealing of nicked DNA substrates is first activated through ATP hydrolysis, resulting in covalent addition of an AMP group to the enzyme. After binding to a nicked site in a DNA duplex, the ligase transfers this AMP to the phosphorylated 5'-end at the nick, forming a 5'-5' pyrophosphate bond. Finally, the ligase catalyzes an attack on this pyrophosphate bond by the OH group at the 3'-end of the nick, thereby sealing it, whereafter ligase and AMP are released. If the ligase detaches from the substrate before the 3' attack, e.g. because of premature AMP reloading of the enzyme, then the 5' AMP is left at the 5'-end, blocking further ligation attempts. In some instances, ATP is added at a concentration of about 1 µM, about 10 µM, about 100 µM, about 1000 µM, or about 10000 µM during the ligation reaction.

In some instances, cofactors that aid in joining of the probe oligonucleotides are added during the ligation process. In some instances, the cofactors include magnesium ions (Mg2+). In some instances, the cofactors include manganese ions (Mn2+). In some instances, Mg2+ is added in the form of MgCl2. In some instances, Mn2+ is added in the form of MnCl2. In some instances, the concentration of MgCl2 is at about 1 mM, at about 10 mM, at about 100 mM, or at about 1000 mM. In some instances, the concentration of MnCl2 is at about 1 mM, at about 10 mM, at about 100 mM, or at about 1000 mM.

In some instances, the ligation reaction occurs at a pH in the range of about 6.5 to 9.0, of about 6.5 to 8.0, of about 7.5 to 8.0, of about 7.5, or of about 8.0.

Following the enzymatic ligation reaction, the first and second probe oligonucleotides may be considered ligated (e.g., thereby generating a ligated probe, ligated product or ligation product).

In some embodiments, the probe oligonucleotides (e.g., the first probe oligonucleotide and the second probe oligonucleotide) may each comprise a reactive moiety such that, upon hybridization to the target and exposure to appropriate ligation conditions, the probe oligonucleotides may ligate to one another. In some embodiments, probe oligonucleotide that includes a reactive moiety is a ligated chemically. For example, a probe oligonucleotide capable of hybridizing to a sequence 3' of a target sequence (e.g., a first target region) of a nucleic acid molecule may comprise a first reactive moiety, and a probe oligonucleotide capable of hybridizing to a sequence 5' of a target sequence (e.g., a second target region) of the nucleic acid molecule may comprise a second reactive moiety. When the first and second probe oligonucleotides are hybridized to the first and second target regions of the nucleic acid molecule, the first and second reactive moieties may be adjacent to one another. A reactive moiety of a probe may be selected from the non-limiting group consisting of azides, alkynes, nitrones (e.g., 1,3-nitrones), strained alkenes (e.g., trans-cycloalkenes such as cyclooctenes or oxanorbornadiene), tetrazines, tetrazoles, iodides, thioates (e.g., phorphorothioate), acids, amines, and phosphates. For example, the first reactive moiety of a first probe oligonucleotide may comprise an azide moiety, and a second reactive moiety of a second probe oligonucleotide may comprise an alkyne moiety. The first and second reactive moieties may react to form a linking moiety. A reaction between the first and second reactive moieties may be, for example, a cycloaddition reaction such as a strain-promoted azide-alkyne cycloaddition, a copper-catalyzed azide-alkyne cycloaddition, a strain-promoted alkyne-nitrone cycloaddition, a Diels-Alder reaction, a [3+2] cycloaddition, a [4+2] cycloaddition, or a [4+1] cycloaddition; a thiol-ene reaction; a nucleophilic substation reaction; or another reaction. In some cases, reaction between the first and second reactive moieties may yield a triazole moiety or an isoxazoline moiety. A reaction between the first and second reactive moieties may involve subjecting the reactive moieties to suitable conditions such as a suitable temperature, pH, or pressure and providing one or more reagents or catalysts for the reaction. For example, a reaction between the first and second reactive moieties may be catalyzed by a copper catalyst, a ruthenium catalyst, or a strained species such as a difluorooctyne, dibenzylcyclooctyne, or biarylazacyclooctynone. Reaction between a first reactive moiety of a first probe oligonucleotide hybridized to a first target region of the nucleic acid molecule and a second reactive moiety of a third probe oligonucleotide hybridized to a second target region of the nucleic acid molecule may link the first probe oligonucleotide and the second probe oligonucleotide to provide a ligated probe. Upon linking, the first and second probe oligonucleotides may be considered ligated. Accordingly, reaction of the first and second reactive moieties may comprise a chemical ligation reaction such as a copper-catalyzed 5' azide to 3' alkyne "click" chemistry reaction to form a triazole linkage between two probe oligonucleotides. In other non-limiting examples, an iodide moiety may be chemically ligated to a phosphorothioate moiety to form a phosphorothioate bond, an acid may be ligated to an amine to form an amide bond, and/or a phosphate and amine may be ligated to form a phosphoramidate bond.

In some embodiments, after ligation of the first and second probe oligonucleotides to create the ligated probe, the ligated probe is released from the analyte. In some embodiments, the ligated probe is released enzymatically. In some embodiments, an endoribonuclease is used to release the probe from the analyte. In some embodiments, the endoribonuclease is one or more of RNase H, RNase A, RNase C, or RNase I.

In some instances, the endoribonuclease is RNAse H. RNase H is an endoribonuclease that specifically hydrolyzes the phosphodiester bonds of RNA, when hybridized to DNA. The RNases H are a conserved family of ribonucleases which are present many different organisms. There are two primary classes of RNase H: RNase H1 and RNase H2. Retroviral RNase H enzymes are similar to the prokaryotic RNase H1. All of these enzymes share the characteristic that they are able to cleave the RNA component of an RNA:DNA heteroduplex. In some embodiments, the RNase H is RNase H1, RNase H2, or RNase H1, or RNase H2. In some embodiments, the RNase H includes but is not limited to RNase HII from *Pyrococcus furiosus*, RNase HIII from *Pyrococcus horikoshi*, RNase HI from *Thermococcus litoralis*, RNase HI from *Thermus thermophilus*, RNAse HI from *E. coli*, or RNase HII from *E. coli*.

In some embodiments, after creating a ligated probe from the probe oligonucleotides (e.g., a first probe oligonucleotide and second probe oligonucleotide), the biological sample is permeabilized. In some embodiments, permeabilization occurs using a protease. In some embodiments, the protease is an endopeptidase. Endopeptidases that can be used include but are not limited to trypsin, chymotrypsin, elastase, thermolysin, pepsin, clostripan, glutamyl endopeptidase (GluC), ArgC, peptidyl-asp endopeptidase (ApsN), endopeptidase LysC and endopeptidase LysN. In some embodiments, the endopeptidase is pepsin.

Detailed descriptions of targeted RNA capture using RNA-templated ligation (RTL) has been disclosed in U.S. application No. 62/952,736, the entirety of which is incorporated herein by reference.

In some embodiments, after creating a ligated probe from the probe oligonucleotides (e.g., a first probe oligonucleotide and second probe oligonucleotide), the biological sample is permeabilized. In some embodiments, permeabilization occurs using a protease (e.g., an endopeptidase disclosed herein).

In some embodiments, the ligated probe includes a capture binding domain, which can hybridize to a capture probe (e.g., a capture probe immobilized, directly or indirectly, on a substrate), and a blocking domain, which prevents interaction between the capture binding domain and a capture domain of a capture probe. Non-limiting examples of blocking domains are described herein.

In some embodiments, the ligated probe includes a capture binding domain, which can hybridize to a capture probe (e.g., a capture probe immobilized, directly or indirectly, on a substrate), where the capture binding domain includes a plurality of caged nucleotides, wherein a caged nucleotide of the plurality of caged nucleotides includes a caged moiety that is capable of preventing interaction between the capture binding domain and the capture domain of the capture probe. Non-limiting examples of caged nucleotides, including examples of caged moieties, are described herein.

In some embodiments, methods provided herein include contacting a biological sample with a substrate, wherein the capture probe is affixed to the substrate (e.g., immobilized to the substrate, directly or indirectly). In some embodiments, the capture probe includes a spatial barcode and the capture domain. In some embodiments, prior to hybridization, the block is released from the capture binding domain of the ligated probes. In another embodiments, prior to hybridization, the caged moieties are released from the capture binding domain. The ligated probe then binds to the capture domain of the capture probe. After hybridization of the ligated probe to the capture probe, the ligated probe is analyzed (e.g., the sequence is determined) using methods disclosed herein, including but not limited to extension of the probe, RT, addition of adaptors, and sequencing.

(e) Kits

In some embodiments, also provided herein are kits that include one or more reagents to detect one or more analytes described herein. In some instances, the kit includes a substrate comprising a plurality of capture probes comprising a spatial barcode and the capture domain. In some instances, the kit includes a plurality of an analyte binding moieties as described herein. In some instances, the analyte-binding moiety of the plurality is associated with an oligonucleotide comprising an analyte-binding-moiety barcode and the capture binding domain. In some instances, the kit includes a plurality of first probe oligonucleotides and second probe oligonucleotides as described herein. In some instances, the first probe oligonucleotide and a second probe oligonucleotide each comprises sequences that are substantially complementary to an analyte, and wherein the second probe oligonucleotide comprises a capture binding domain. In some instances, the kit further includes a plurality of blocking probes as described herein.

In some embodiments, reagents can include one or more antibodies (and/or antigen-binding antibody fragments), labeled hybridization probes, and primers. For example, in some embodiments, an antibody (and/or antigen-binding antibody fragment) can be used for visualizing one or more features of a tissue sample (e.g., by using immunofluorescence or immunohistochemistry). In some embodiments, an antibody (and/or antigen-binding antibody fragment) can be an analyte binding moiety, for example, as part of an analyte capture agent. Useful commercially available antibodies will be apparent to one skilled in the art.

In some embodiments, labeled hybridization probes can be used for in situ sequencing of one or more biomarkers and/or candidate biomarkers. In some embodiments, primers can be used for amplification (e.g., clonal amplification) of a captured oligonucleotide analyte.

In some embodiments, a kit can further include instructions for performing any of the methods or steps provided herein. In some embodiments, a kit can include a substrate with one or more capture probes comprising a spatial barcode and a capture domain that binds to a biological analyte from a tissue sample, and reagents to detect a biological analyte, wherein the biological analyte is any of the biomarkers of this disclosure. In some embodiments, the kit further includes but is not limited to one or more antibodies (and/or antigen-binding antibody fragments), labeled hybridization probes, primers, or any combination thereof for visualizing one or more features of a tissue sample.

What is claimed is:

1. A method for identifying the location of a nucleic acid analyte in a biological sample, the method comprising:
   (a) contacting the biological sample with a first substrate;
   (b) hybridizing a first probe and a second probe to the nucleic acid analyte, wherein the second probe comprises a capture binding domain that hybridizes to a capture domain of a capture probe, wherein the capture probe is affixed to the first substrate or wherein the capture probe is affixed to a second substrate, wherein the capture probe further comprises a spatial barcode, and wherein a portion of the capture binding domain is hybridized to a blocking probe;
   (c) ligating the first probe and the second probe, thereby creating a ligation product, wherein the ligation product comprises a sequence that is substantially complementary to the nucleic acid analyte;
   (d) releasing:
      (i) the ligation product from the nucleic acid analyte, and
      (ii) the blocking probe from the capture binding domain;
   (e) hybridizing the capture binding domain to the capture domain; and
   (f) determining (i) all or part of the sequence of the ligation product, or a complement thereof, and (ii) the sequence of the spatial barcode, or a complement thereof, and using the determined sequences of (i) and (ii) to identify a location of the nucleic acid analyte in the biological sample.

2. The method of claim 1, further comprising determining the abundance of the nucleic acid analyte in the biological sample.

3. The method of claim 1, wherein the first probe and the second probe are substantially complementary to adjacent sequences of the nucleic acid analyte.

4. The method of claim 1, wherein the first probe and the second probe are DNA probes.

5. The method of claim 1, wherein the ligating comprises ligating the first probe and the second probe using chemical ligation.

6. The method of claim 1, wherein the ligating is enzymatic ligation using a ligase, and wherein the ligase is one or more of a T4 RNA ligase (Rnl2), a *Chlorella* virus DNA Ligase, a single-stranded DNA ligase, or a T4 DNA ligase.

7. The method of claim 1, wherein the blocking probe comprises a sequence that is at least 80% complementary to the capture binding domain, and wherein the capture binding domain comprises a first sequence that is substantially complementary to the capture domain of the capture probe on the first or second substrate.

8. The method of claim 1, wherein the capture binding domain comprises a contiguous sequence comprising (i) a first sequence substantially complementary to the capture domain and (ii) a second sequence substantially complementary to the blocking probe.

9. The method of claim 1, wherein the releasing the blocking probe from the capture binding domain comprises contacting the blocking probe with an endoribonuclease selected from RNase H, RNase A, RNase C, or RNase I.

10. The method of claim 1, wherein the nucleic acid analyte is RNA.

11. The method of claim 1, wherein the first substrate comprises a plurality of capture probes, and wherein each capture probe of the plurality of capture probes comprises the capture domain.

12. The method of claim 1, wherein the capture probe is on the second substrate, wherein the second substrate comprises a plurality of capture probes, and wherein each capture probe of the plurality of capture probes comprises the capture domain.

13. The method of claim 12, further comprising aligning the first substrate with the second substrate such that at least a portion of the biological sample is aligned with at least a portion of the plurality of capture probes.

14. A method for enhancing the binding of a ligation product to a capture domain, the method comprising:
   (a) contacting a biological sample with a first substrate;
   (b) hybridizing a first probe and a second probe to a nucleic acid analyte in the biological sample, wherein the second probe comprises a capture binding domain that hybridizes to a capture domain of a capture probe, wherein the capture probe is affixed to the first substrate or wherein the capture probe is affixed to a second substrate, wherein the capture probe further comprises a spatial barcode, and wherein a portion of the capture binding domain is hybridized to a blocking probe;
   (c) ligating the first probe and the second probe, thereby creating the ligation product, wherein the ligation product comprises a sequence that is substantially complementary to the nucleic acid analyte;
   (d) releasing:
      (i) the ligation product from the nucleic acid analyte, and
      (ii) the blocking probe from the capture binding domain; and
   (e) hybridizing the capture binding domain to the capture domain,
thereby enhancing the binding of the ligation product to the capture domain compared to methods that do not include the blocking probe.

15. The method of claim 14, further comprising determining the abundance of the nucleic acid analyte in the biological sample.

16. The method of claim 14, wherein the first probe and the second probe are substantially complementary to adjacent sequences of the nucleic acid analyte.

17. The method of claim 14, wherein the first probe and the second probe are DNA probes.

18. The method of claim 14, wherein the ligating comprises ligating the first probe and the second probe using enzymatic ligation or chemical ligation; wherein the enzymatic ligation is performed using a ligase and wherein the ligase is one or more of a T4 RNA ligase (Rnl2), a *Chlorella* virus DNA Ligase, a single-stranded DNA ligase, or a T4 DNA ligase.

19. The method of claim 14, wherein the blocking probe comprises a sequence that is at least 80% complementary to the capture binding domain, and wherein the capture binding domain comprises a first sequence that is substantially complementary to the capture domain.

20. The method of claim 14, wherein the capture binding domain comprises a contiguous sequence comprising (i) a first sequence substantially complementary to the capture domain and (ii) a second sequence substantially complementary to the blocking probe.

21. The method of claim 14, wherein the releasing the blocking probe from the capture binding domain comprises contacting the blocking probe with an endoribonuclease selected from RNase H, RNase A, RNase C, or RNase I.

22. The method of claim 14, wherein the nucleic acid analyte is RNA.

23. The method of claim 14, wherein the first substrate comprises a plurality of capture probes, and wherein each capture probe of the plurality of capture probes comprises the capture domain.

24. The method of claim 14, wherein the capture probe is on the second substrate, wherein the second substrate comprises a plurality of capture probes, and wherein each capture probe of the plurality of capture probes comprises the capture domain.

25. The method of claim 24, further comprising aligning the first substrate with the second substrate such that at least a portion of the biological sample is aligned with at least a portion of the plurality of capture probes.

\* \* \* \* \*

SEQUENCE LISTING

```
<160> NUMBER OF SEQ ID NOS: 6

<210> SEQ ID NO 1
<211> LENGTH: 23
<212> TYPE: DNA
<213> ORGANISM: Artificial
<220> FEATURE:
<223> OTHER INFORMATION: Capture probe sequence

<400> SEQUENCE: 1
aaaaaaaaaa aaaaaaaaaa aaa                                             23

<210> SEQ ID NO 2
<211> LENGTH: 23
<212> TYPE: DNA
<213> ORGANISM: Artificial
<220> FEATURE:
<223> OTHER INFORMATION: Capture probe blocking sequence

<400> SEQUENCE: 2
tttttttttt tttttttttt ttt                                             23
```

```
<210> SEQ ID NO 3
<211> LENGTH: 30
<212> TYPE: DNA
<213> ORGANISM: Artificial
<220> FEATURE:
<223> OTHER INFORMATION: Capture probe sequence

<400> SEQUENCE: 3
aaaaaaaaaa aaaaaaaaaa aaaaaaaaaa                                30

<210> SEQ ID NO 4
<211> LENGTH: 18
<212> TYPE: DNA
<213> ORGANISM: Artificial
<220> FEATURE:
<223> OTHER INFORMATION: hairpin sequence

<400> SEQUENCE: 4
tttttttttt tttttttt                                             18

<210> SEQ ID NO 5
<211> LENGTH: 30
<212> TYPE: RNA
<213> ORGANISM: Artificial
<220> FEATURE:
<223> OTHER INFORMATION: Capture probe blocking sequence

<400> SEQUENCE: 5
uuuuuuuuuu uuuuuuuuuu uuuuuuuuuu                                30

<210> SEQ ID NO 6
<211> LENGTH: 23
<212> TYPE: RNA
<213> ORGANISM: Artificial
<220> FEATURE:
<223> OTHER INFORMATION: Capture probe blocking sequence

<400> SEQUENCE: 6
uuuuuuuuuu uuuuuuuuuu uuu                                       23
```